(12) United States Patent
Morsy et al.

(10) Patent No.: US 6,630,346 B1
(45) Date of Patent: Oct. 7, 2003

(54) GENE THERAPY FOR OBESITY

(75) Inventors: Manal Morsy, Blue Bell, PA (US);
MingCheng Gu, Maple Glen, PA (US);
Jing Zhang Zhao, Chalfont, PA (US);
C. Thomas Caskey, Houston, TX (US);
Stephan Kochanek, Ulm (DE)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/202,684

(22) PCT Filed: Jun. 20, 1997

(86) PCT No.: PCT/US97/10371

§ 371 (c)(1),
(2), (4) Date: Apr. 1, 1999

(87) PCT Pub. No.: WO97/48806

PCT Pub. Date: Dec. 24, 1997

Related U.S. Application Data

(63) Continuation of application No. 08/878,737, filed on Jun. 19, 1997, now abandoned.
(60) Provisional application No. 60/026,753, filed on Sep. 26, 1996, and provisional application No. 60/020,813, filed on Jun. 20, 1996.

(51) Int. Cl.[7] .......................... C12N 5/00; C12N 15/00; C12N 15/63; C12P 21/06; C07H 21/02; C07H 21/04; A01N 43/04
(52) U.S. Cl. ................... 435/325; 435/69.1; 435/320.1; 435/455; 536/23.1; 536/23.5; 514/44
(58) Field of Search .................. 514/44, 2, 3; 424/93.1, 424/198.1; 435/320.1, 169.1, 325, 455; 536/23.1, 23.5

(56) References Cited

U.S. PATENT DOCUMENTS

| | | | |
|---|---|---|---|
| 5,830,462 A | 11/1998 | Crabtree et al. | 435/93.21 |
| 5,834,266 A | 11/1998 | Crabtree et al. | 435/172.3 |
| 5,869,337 A | 2/1999 | Crabtree et al. | 435/372.3 |
| 5,871,753 A | 2/1999 | Crabtree et al. | 424/280.1 |
| 5,919,676 A * | 7/1999 | Graham et al. | 435/172 |

FOREIGN PATENT DOCUMENTS

| WO | WO95/27071 | * 10/1995 | C12N/15/86 |
|---|---|---|---|
| WO | WO96/05309 | * 2/1996 | C12N/15/12 |

OTHER PUBLICATIONS

Touchette, Nat. Med. 2(1) 7–8, 1996, 1998.*
Burcin et al, PNAS 96:355–360, 1999.*
Amalfitano et al, 72(3):926–933, 1998.*
Anderson, WF, Nature 392:25–30, 1998.*
Descamps et al., Erythropoietin Gene Transfer and Expression in Adult Normal Mice: Use of an Adenovirus Vector, 1994, Human Gene Therapy, vol. 5, pp. 979–985.*
Morsy et al., An Adenoviral vector deleted for all viral coding sequences results in enhanced safety and extended expression of a leptin transgene, 1998, Proc. Natl. Acad. Sci. USA, vol. 95, pp. 7866–7871.*
Burcin, M. et al. "Adenovirus–mediated regulable target gene expression in vivo" Proc. Natl. Acad. Sci. USA, vol. 96, pp. 355–360, Jan. 1999.
Gronemeyer, H. et al., "Mechanisms of Antihorme Action" J. Steroid Biochem. Molec. Biol. vol. 41, No. 3–8, pp. 217–221, 1992.
Wang, Y. et al. "A regulatory system for use in gene transfer" Proc. Natl. Acad. Sci. USA, vol. 91, pp. 8180–8184, Aug. 1994.
Steinwaerder, D. et al. "Generation of Adenovirus Vectors Devoid of All Viral Genes by Recombination between Inverted Repeats" Journal of Virology, vol. 73, No. 11, Nov. 1999, pp. 9303–9313.
Fisher, K. et al. "Recombinant Adenovirus Deleted of All Viral Genes fo r Gene Therapy of Cystic Fibrosis" Virology 217, pp. 11–22, 1996.
Alemany, R. et al. "Complementation of helper–dependent adenoviral vectors: size effects and titer fluctuations" Journal of Virological Methods 68 (1997) pp. 147–159.

* cited by examiner

*Primary Examiner*—Jeffrey Fredman
*Assistant Examiner*—Sumesh Kaushal
(74) *Attorney, Agent, or Firm*—Anna L. Cocuzzo; Jack L. Tribble

(57) ABSTRACT

Gene therapy can treat obesity in mammals. An obesity regulating gene is delivered to a mammal. Preferably, the gene encodes leptin or a leptin receptor. The protein which is delivered and expressed in vivo is more effective than protein which is injected into the animal.

7 Claims, 43 Drawing Sheets

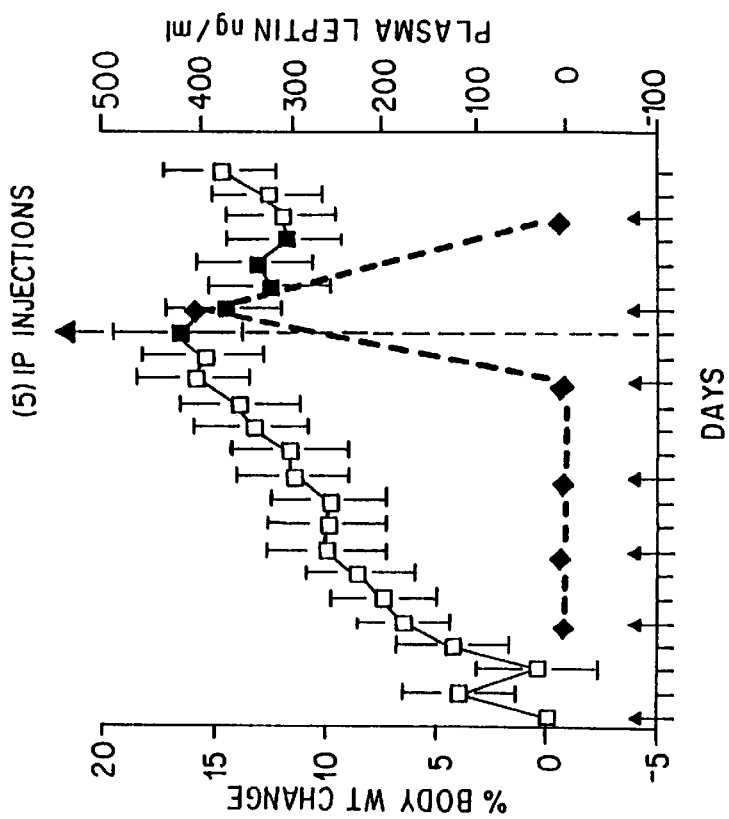
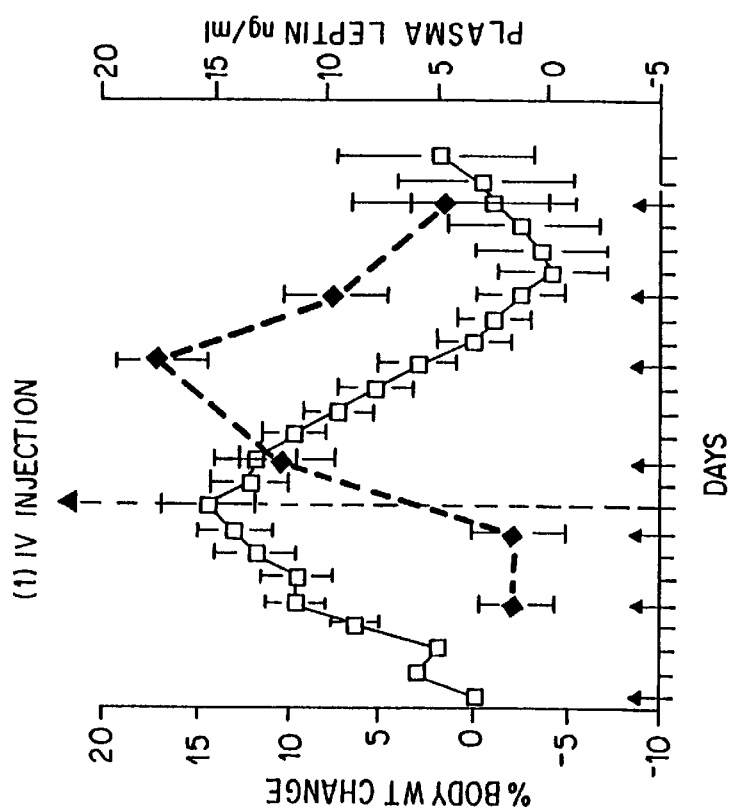
FIG.6B
FIG.6A

- ● HUMAN LEPTIN IN ob/ob TREATED WITH 1μg/gm RECOMBINANT PROTEIN DAILY FOR 5 DAYS
- ■ HUMAN LEPTIN IN ob/ob TREATED WITH A SINGLE INJECTION OF 2.75×10⁸ pfu OF VIRAL VECTOR
- ◇ LEAN INSULIN LEVELS
- □ INSULIN IN ADENO-TREATED ob/ob
- ○ INSULIN IN RECOM. LEPTIN TREATED ob/ob

```
                           SEQUENCE LISTING

<160> NUMBER OF SEQ ID NOS: 9

<210> SEQ ID NO 1
<211> LENGTH: 20
<212> TYPE: DNA
<213> ORGANISM: Artificial Sequence
<220> FEATURE:
<223> OTHER INFORMATION: PCR primer

<400> SEQUENCE: 1
atgcattggg gaaccctgtg                                              20

<210> SEQ ID NO 2
<211> LENGTH: 20
<212> TYPE: DNA
<213> ORGANISM: Artificial Sequence
<220> FEATURE:
<223> OTHER INFORMATION: PCR primer

<400> SEQUENCE: 2
tcagcaccca gggctgaggt                                              20

<210> SEQ ID NO 3
<211> LENGTH: 30
<212> TYPE: DNA
<213> ORGANISM: Artificial Sequence
<220> FEATURE:
<223> OTHER INFORMATION: Single-stranded oligodeoxynucleotide for
      generation of viral construct

<400> SEQUENCE: 3
ggcgcgcccc tagggccgg ccttaattaa                                    30

<210> SEQ ID NO 4
<211> LENGTH: 30
<212> TYPE: DNA
<213> ORGANISM: Artificial Sequence
<220> FEATURE:
<223> OTHER INFORMATION: Single-stranded oligodeoxynucleotide for
      generation of viral construct

<400> SEQUENCE: 4
ttaattaagg ccggcccta ggggcgcgcc                                    30
```

```
<210> SEQ ID NO 5
<211> LENGTH: 30
<212> TYPE: DNA
<213> ORGANISM: Artificial Sequence
<220> FEATURE:
<223> OTHER INFORMATION: Single-stranded oligodeoxynucleotide for
      generation of viral construct

<400> SEQUENCE: 5
atttaaatgc ccgcccgttt aaactacgta                                        30

<210> SEQ ID NO 6
<211> LENGTH: 30
<212> TYPE: DNA
<213> ORGANISM: Artificial Sequence
<220> FEATURE:
<223> OTHER INFORMATION: Single-stranded oligodeoxynucleotide for
      generation of viral construct

<400> SEQUENCE: 6
tacgtagttt aaacgggcgg gcatttaaat                                        30

<210> SEQ ID NO 7
<211> LENGTH: 39
<212> TYPE: DNA
<213> ORGANISM: Artificial Sequence
<220> FEATURE:
<223> OTHER INFORMATION: PCR primer

<400> SEQUENCE: 7
agctttgttt aaacatcatc aataatatac cttattttg                              39

<210> SEQ ID NO 8
<211> LENGTH: 35
<212> TYPE: DNA
<213> ORGANISM: Artificial Sequence
<220> FEATURE:
<223> OTHER INFORMATION: PCR primer

<400> SEQUENCE: 8
cgataagctt gatatcaaaa cgccaacttt gaccc                                  35

<210> SEQ ID NO 9
<211> LENGTH: 36
<212> TYPE: DNA
<213> ORGANISM: Artificial Sequence
<220> FEATURE:
<223> OTHER INFORMATION: PCR primer

<400> SEQUENCE: 9
cgataagctt gatatcactc cgccctaaaa cctacg                                 36
```

GENE THERAPY FOR OBESITY

CROSS-REFERENCE TO RELATED APPLICATIONS

This application is a National stage entry of PCT/US97/10371, filed Jun. 20, 1997, which is a con't of U.S. application Ser. No. 08/878,737, filed Jun. 19, 1997, now abandoned. Said application claims priority to Provisional Application Ser. No. 60/020,813, filed Jun. 20, 1996, and to Provisional Application Ser. No. 60/026,753, filed Sep. 26, 1996.

FIELD OF THE INVENTION

This invention relates to methods of gene therapy by vector-assisted delivery of a peptide hormone, and to transgenic non-human mammals so produced. This invention also related to gene therapy for obesity. This invention also relates to vectors useful in this gene therapy.

BACKGROUND OF THE INVENTION

There are numerous potentially therapeutic hormones which are peptides or proteins, including leptin, insulin, calcitonin, erythropoietin, (EPO), growth hormone, interferons, interleukin-2, hemophilia factors, vascular endothelial growth factors such as VEGF, granulocyte-macrophage colony stimulating factor, alpha 1 anti-trypsin, and others. Many have been purified, extensively studied, and even produced recombinantly and administered in a clinical setting. One problem with peptide and/or proteins as therapeutic agents, however, is that they cannot be made into conventional oral dosage forms, as contact with gastric juices will destroy the peptide. Instead, they have to be delivered by injection, intravenously, intranasally or other non-oral routes which are often not convenient for chronic usage, and may add to the expense of the drug therapy. In addition, protein injection is frequently of short duration of action and requires repetitive dosing.

Leptin is a protein expressed by the ob gene. Leptin is secreted by adipose tissue and appears to be both a satiety factor and a regulator of metabolism (Levin et al., 1996 *Proc. Natl Acad. Sci. USA* 93:1726–1730). Both the mouse gene and its human homologue have recently been identified and sequenced (Zhang et al., 1994 *Nature* (London) 372:425–431.)

Mice which are homozygous for the ob gene (ob\ob) are obese, perhaps due to leptin deficiency. When ob\ob mice are given daily injections of recombinant protein, their food intake was markedly inhibited and they experienced a reduction in body weight and fat. In lean (i.e. wild-type) mice, daily injections of leptin lead to modest decreases of food intake and body weight. The results for body fat have been confirmatory to the effect of leptin on fat metabolism. (Pelleymounter et al., 1995, *Science* 269:540–543; Halaas et al., 1995 *Science* 269: 543–546; and Campfield et al., 1995 *Science* 269:546–549).

Obesity in humans is a major disorder associated with mortality, and may result from a number of causes, and at least some may be due to an insufficient amount of leptin produced or resistance. Since leptin is a protein, and vulnerable to breakdown and inactivation by the gastrointestinal system, it cannot be delivered orally. It would be desirable to develop a therapy for leptin delivery for obese patients whose obesity is due, at least in part, to a paucity of leptin or resistance to the sustained peripheral levels.

BRIEF DESCRIPTION OF THE INVENTION

This invention relates to gene therapy wherein a viral vector is used to deliver a protein or peptide which is also a hormone. One aspect of this invention involves a method of treating a condition which is caused at least in part by an insufficient production of or resistance to a peptide or protein hormone in a mammal comprising administration of a viral vector comprising a gene encoding the peptide or protein hormone. It has been found, in accordance with this invention, that the amount of protein or peptide hormone needed to produce a biological result is much lower when the protein or peptide hormone is made by the mammal receiving the gene therapy, as compared to the amount needed to produce the same biological result when the peptide or protein hormone is delivered to the mammal by, e.g. muscular injection or intravenous administration. Further, the mammal which is expressing the gene which has been introduced by gene therapy does not develop antibodies to the peptide or protein hormone. In contrast, a mammal which receives the same peptide or protein hormone by injection or intravenous administration, may develop antibodies to the hormone.

Thus one aspect of this invention relates to a method of treating a condition caused, at least in part by an insufficient production of a peptide or protein hormone in a mammal comprising administration of a viral vector comprising a gene encoding the peptide or protein hormone wherein the gene encodes a hormone selected from the group consisting of: leptin, insulin, calcitonin, erythropoietin, growth hormone, interferons, interleukin-2, a hemophilia factor, a vascular endothelial growth factor, granulocyte-macrophage colony stimulating factor, and alpha 1 anti-trypsin.

This invention is also related to gene therapy for obesity. One aspect of this invention involves a method of treating obesity, lowering serum glucose levels or lowering serum insulin levels in a mammal in need of such therapy comprising delivering a gene encoding an obesity regulating gene to said mammal; and allowing sufficient time to pass for transcription and translation of the obesity regulating gene.

Some types of obesity are caused by an insufficient amount of leptin. Along with obesity the individual may also experience elevated serum glucose and/or insulin levels. Thus, another aspect of this invention is a method of treating obesity, elevated serum glucose levels, or elevated insulin levels comprising delivering a gene encoding leptin to a mammal wherein transcription and translation of the gene occurs in vivo. By "insufficient amount of leptin produced" it is envisioned that the mammal may produce functional leptin, but at lower levels than required; alternatively the animal may have a complete inability to produce leptin; or in yet another alternative, the animal produces a mutated form of leptin which either functions less efficiently than native leptin or does not function at all.

Non-human mammals, particularly rodents such as mice and rats which have received peptide or protein hormone transgenes and which express the peptide or protein hormone make up another aspect of this invention. Specifically, mice which have received the leptin gene transgenically and which express leptin, form another aspect of this invention. Mice may be ob/ob, Ob!? or homozygous wild-type for the ob gene prior to receipt of the leptin gene. Progeny of these mammals make up yet another aspect of this invention.

Yet another aspect of this invention are viral vectors for the delivery of peptide or protein hormone genes to be used in gene therapy. In one embodiment adenoviral vectors are provided, including those with deletions in all viral protein coding sequences, which are less immunogenic than previous vectors.

Still further aspects of this invention include mammalian cells transformed with vectors of this invention.

Another aspect of this invention is a method of determining whether a compound has the ability to modulate leptin activity in vivo comprising administering the compound to a transgenic animal of this invention and monitoring the animal's reaction to the compound. In this way, leptin agonists, antagonists and mimetics may be identified, or if a compound shows leptin modulating activity in in vitro assays, it can be determined if this activity is retained in vivo.

BRIEF DESCRIPTION OF THE FIGURES

FIG. 6A (left graph) is a graph showing the amount of human leptin found in the plasma of mice treated with adenovirus containing the leptin gene as described in Example 3. FIG. 6B (right graph) shows results for mice in the pilot study treated with five daily injections of recombinant human leptin.

FIG. 10 shows the body weight changes in oblob mice which were used as controls.

FIG. 11A is the pilot study mice. FIG. 11B shows mice in the expanded study which received control injections, and FIG. 11C shows mice in the expanded study which received leptin injections.

FIG. 14A shows mice which received adenovirus carrying human leptin gene, and FIG. 14B shows mice which received human leptin IP injections.

FIG. 15A shows serum levels of human or mouse leptin and weight for animals receiving leptin genes. FIG. 15B shows leptin levels and weight for animals receiving leptin injections, and notes the antibody response.

FIGS. 26 A–F show effects of HD-leptin and Ad-leptin in lean mice. In each graph: solid circle is HD-lepfin; circle with cross is Ad-leptin; open circle is AD-β-gal; and open triangle is dialysis buffer.

FIGS. 27 A–F show effects of HD-leptin and Ad-leptin in ob/ob mice. In each graph, solid circle is HD-leptin; circle with cross is Ad-leptin; open circle is AD-β-gal; open triangle is dialysis buffer; as asterisk is lean control values plotted for relative comparison.

Figure 1:
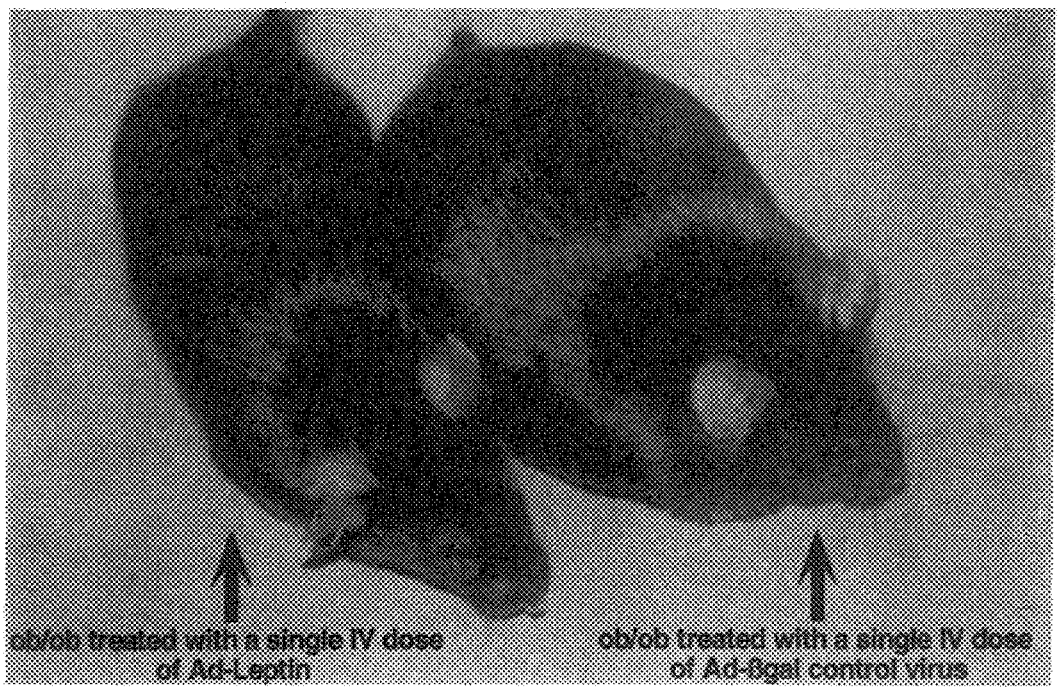
FIG. 1 is a photograph of two oblob mice. The mouse on the right is from a control group. The mouse on the left received gene therapy in accordance with the pilot study (Example 3) of this invention.

As used throughout the specification and claims, the following definitions apply:

"Native" a gene or protein is native if it naturally occurs in a given organism.

"Transgene": a gene which has been introduced into a mammal or its ancestor using a viral vector.

"Transgene construct" or "expression cassette" means a transgene and associated DNA, such as promoter(s) enhancer(s), and terminal sequences needed for control of transcription and translation of the transgene.

"Leptin gene": a gene from any mammal which encodes a native leptin, or a derivative thereof. A "derivative" is a modified leptin molecule which retains at least 80% of the biological activity of native leptin.

"Protein or peptide hormone" any hormone which is in the form of a protein or peptide, whether or not post-translationally modified. Examples include: leptin, insulin, calcitonin, EPO, growth hormone, interferon, IL-2, vascular endothelial growth factors such as VEGF, GMCSF and alpha 1 anti-trypsin.

"Obesity regulating gene": a gene whose gene product is involved in the regulation of obesity in a mammal, including genes encoding leptin, leptin receptors, neuropeptide Y. and the like.

"oblob" means the animal is deficient in leptin.

"lean" means the animal expresses normal levels of leptin and genotypically are homozygous normal for the leptin gene.

"Obl?" means the animal expresses leptin, but it is unknown if the animal is homozygous normal or a carrier of the leptin gene defect.

"bp" means base pair

"IV" or "iv" means intravenous injection.

"IP" means intraperitoneal injection.

"IM" means intramuscular injection.

"Ad" means adenovirus.

"Ad-leptin" means an adenovirus vector carrying a leptin transgene.

"HD" means helper-dependent virus system.

"HD-leptin" means a helper dependent virus carrying a leptin transgene.

"wild-type" or "wt" refers to the non-mutated form of a gene. With reference to the ob gene, a mouse with a wild-type phenotype is lean.

In the past, recombinant peptide hormones have been administered to mammals (including man) suffering from conditions caused at least in part by an insufficiency of the hormone. Examples include replacement of congenital (e.g. hemophilias) or acquired (e.g. erythropoetin) deficiencies. Enhanced expression of loci that might provide a therapeutic benefit (e.g. LDL receptor or apolipoprotein A-I) may best be accomplished by very long-term or permanent expression with tissue-specific and physiologic regulation. These conditions include diabetes, alpha 1-anti-trypsin deficiency, etc. However, one problem with such therapy is the inconvenience and associated expense of an injection or iv administration. Also, the recipient may develop antibodies to the administered hormone.

Recombinant leptin has been administered to animals who exhibiting an obese phenotype, and a daily injection has been shown to decrease body weight. There are numerous disadvantages to this method of treating obesity, however. Injections are not a particularly convenient method of treatment, particularly for long-term treatments. In addition, the half-life of leptin is short, so the duration of a single treatment was found to be only about 24 hours, after which the animals were observed to re-gain weight.

It has been found, in accordance with this invention, that a peptide or protein hormone which is expressed in vivo is more advantageous than administration of the recombinant form of that hormone; its effects last longer, and most surprisingly, is up to 20 fold more potent than recombinant peptide hormone administered by injection. Further, if the recipient mammal endogenously produces the hormone, no immune response with respect to the transgenic hormone is observed.

This invention utilizes the leptin gene delivered to ob/ob mice as a model for peptide hormones in general. Leptin was chosen because its nucleic acid and amino acid sequences were known, and its effects on obese ob/ob mice are visually apparent as well as biochemically apparent. Applicants are not aware of any reason why their findings for leptin are not generally applicable to all peptide or protein hormones, and intend for this invention to be construed broadly.

Gene Constructs

The sequences of leptin and leptin genes from various species are known (Zhang et al., 1994 *Nature* 372:425; Ogawa et al., 1995 *J. Clin. Invest.* 96:1647–1652; Murakami et al., 1995 *Biochem. Biophys. Res. Commun.* 209:944; and Considine et al., 1995 *J. Clin. Invest.* 95:2986; each of which is hereby incorporated by reference). If desired, genes encoding leptin derivatives may also be used. Since the amino acid and nucleotide sequence of leptin is known, it is well within the skill of one of the ordinary artisan to construct a nucleotide sequence which encodes a desired mutant form of leptin. These can be used to study structure and function relationships involved in leptin binding and signaling in the transgenic animal model.

The gene which encodes the leptin should also contain at least one element which allows for expression of the gene when introduced into the host cell environment. These sequences include, but are not limited to promoters, response elements, and enhancer elements.

In a preferred aspect of this invention, promoters are chosen which are regulatable; i.e. are inducible rather than constitutive. Particular examples of such promoters include: the Gene Switch™ mifepristone inducible gene regulation system commercially available from Gene Medicine; the "two component gene regulation system" commercially available from Ariad, regulatable tet, P-450, and constitutive promoters such as EF-1 alpha, SR-alpha, CMV, albumin and the like.

Vector

The heterologous leptin gene may be delivered to the organism using a vector or other delivery vehicle. DNA delivery vehicles can include viral vectors such as adenoviruses, adeno-associated viruses, helper dependent adenoviruses, and retroviral vectors. See, for example: Chu et al., 1994 *Gene Ther.* 1:292–299; Couture et al., 1994 *Hum. Gene Ther.* 5:667–277; and Eiverhand et al., 1995 *Gene Ther.* 2:336–343.. Non-viral vectors which are also suitable include DNA-lipid complexes, for example liposome-mediated or ligand/poly-L-Lysine conjugates, such as asialoglyco-protein-mediated delivery systems. See for example: Felgner et al., 1994 *J. Biol. Chem.* 269:2550–2561; Derossi et al., 1995, *Restor. Neurol. Neuros.* 8:7–10; and Abcallah et al., 1995 *Biol. Cell* 85:1–7.

If a viral vector is chosen as the delivery vehicle it may be one which is capable of integrating into the host genome, so that the gene can be expressed permanently, but this is not required. In cases where the vector does not integrate into the host genome, the expression of the gene may be transient rather than permanent.

One vector which is suitable for transient expression of the ob gene is an adenovirus which has a deletion in the El gene. Such vectors are known, as taught in the aforementioned WO 95/00655 and Mitani et al., 1995 publications. These viruses preferentially infect hepatocytes, where they persist for approximately 3–4 weeks after the initial infection. While in the hepatocytes, these viruses can express the heterologous gene.

The vector is administered to the host, generally by iv injection but may be intramuscular, intraperitoneal, oral, subcutaneous or other form of delivery. Suitable titers will depend on a number of factors, such as the particular vector chosen, the host, strength of promoter used and the severity of the disease being treated. For mice, an adenovirus vector is preferably administered as an injection at a dose range of from about $5.0 \times 10^6$ to about $10 \times 10^6$ plaque forming units (PFU) per gram body weight. Preferred dosages range from at least about $6-9 \times 10^6$ PFU/gm body weight, and more preferred is from at least about $6.7-8.6 \times 10^6$ PFU/gm body weight (equivalent to approximately at least $1 \times 10^7$ to $1-5 \times 10^8$ PFU for mice). Higher amounts are also useful, and up to $10^{12}$ particles may be used.

If the effect desired is a permanent one rather than a transient one, it is preferred that a helper dependent viral vector be utilized.

Adenoviral (Ad) vectors are currently among the most efficient gene transfer vehicles for both in vitro and in vivo delivery, but the utilization of first generation Ad for many gene therapy applications is limited due to the transient nature of transgene expression obtained by these vectors. Several factors have been shown to contribute to and modulate the duration of Ad-mediated gene expression as well as the immunogenicity of these vectors, including "leaky" viral protein expression and the transgene delivered. The development of Ad vectors, deleted in all viral protein coding sequences, offers the prospects of a potentially safer, less immunogenic vector with an insert capacity of up to approximately 37 kb. This vector requires supplementation of viral regulatory and structural proteins in trans for packaging and rescue, thus helper dependent (HD).

The development of Ad vectors, deleted in all viral protein coding sequences, has resulted in a less immunogenic vector with an insert capacity of up to approximately 37 kb. This class of vectors requires supplementation of viral regulatory and structural proteins in trans for packaging and rescue, and are thus termed "Helper Dependent"(HD). These are further described in Parks et al., 1996 *Proc. Natl. Acad Sci.* 93:13565–13570, and U.S. patent application Ser. No. 08/488,014, filed Jun. 7, 1995 both of which are hereby incorporated by reference.

Figure 25A:
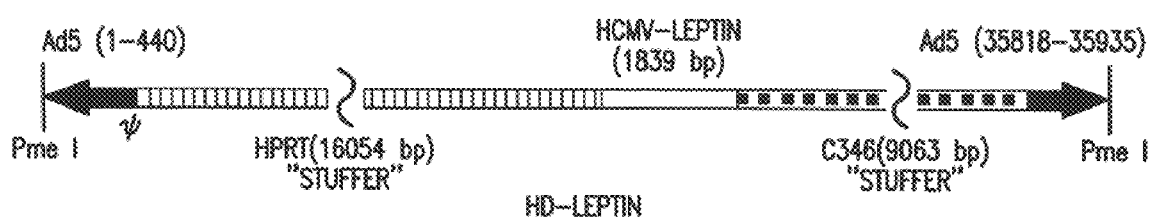
FIG. 25A illustrates the HD-Leptin vector. The DNA composite fragments of HD-leptin inserted into pBluescript IIKS are (left to right): the left end terminus of Ad5, composed of the inverted terminal repeat sequences and the packaging signal ψ (nucleotides (nt.) 1–440, solid arrow), the Pmel-EclX1 16054 bp fragment of HPRT (nt.1799–17853 of HUMHPRTB, shaded bar), the leptin expression cassette, composed of the HCMV promoter, the murine lepfin cDNA (500 bp) and the bovine growth hormone poly A tail (open bar), the HindIII 9063 bp fragment of C346 cosmid (nt. 12421–21484 of HUMDXS455A, shaded bar) and the right end terminus of Ad5, composed of the ITR sequence (nt. 35818–35935). The ITRs are flanked by unique Pmel restriction site used to liberate the vector from the plasmid backbone prior to the initial transfecfion into 293-cre4 cells for viral propagation and rescue.

In a preferred embodiment, the HD vector containing a leptin transgene construct (HD-leptin) comprises the Ad5 inverted terminal repeats (ITR) and packaging signal sequences, a leptin transgene construct, and "stuffer" DNA. Stuffer DNA is human genomic DNA sequences or other non-transcribed DNA sequences used to increase the vector insert size to at least approximately 28 kb. In one embodiment of this invention, the stuffer DNA is a segment of the human hypoxanthine-guanine phosphoribosyltransferase (HPRT) gene. In a particular embodiment of this invention, pSTK 120, the stuffer DNA is intronic HPRT which also contains a matrix association region (MAR). The MAR has been shown to confer DNA attachment to the nuclear matrix. A genome of this size is preferred, as the virus is more stable and productive. An HD-leptin vector is illustrated in FIG. 25A.

A specific embodiment of this invention is vector pSTK120 comprises a first segment of adenovirus a first segment of stuffer DNA, a transgene DNA, construct a second segment of stuffer DNA, and a second segment of adenovirus DNA. The adenovirus DNA is preferably adenovirus type 5 DNA sequences, and together comprise adenovirus inverted terminal repeats (ITRs) that comprise the viral origin of replication and packaging signals. The non-viral DNA can contain up to 38 kb. An important aspect of the vector is that no adenoviral proteins are expressed in the host cell. The first segment of adenovirus type 5 DNA preferably comprises at least about nucleotides 1–440, although more may be present. The second segment of adenovirus type 5 DNA preferably comprises at least about nucleotides 35818–35935.

For propagation of HD-leptin, a helper virus system containing a modified El deleted vector with lox sites flanking the packaging signals (Ad LC8cluc) and a 293 cell line expressing Cre recombinase such as 293-Cre4 is preferred. Such systems are generally known and are described in: Parks et al., 1996, supra; and Edwards et al., 1990 *Genomics* 6:593–608, and U.S. patent applications Ser. No. 08/250,885 (filed May 31, 1994); 08/473,168 (filed Jun. 24, 1995); and 08/719,217 each of which is hereby incorporated by reference.

Hosts

Animals which transiently or permanently express a peptide or protein hormone such as the ob gene product are valuable research tools. For example, they can be used to monitor the effects of decreasing amounts of leptin, or the effect of various exogenously supplied substances (such as hormones or putative leptin receptor agonists and antagonists) in an environment of decreasing leptin availability.

In addition to making animal models useful in studying various aspects of obesity, this invention is specifically directed to gene therapy for humans.

In accordance with this invention, an adenovirus or helper dependent adenovirus containing a transgenic leptin gene (human or murine) is administered to mice which are obese (ob/ob). Although the leptin gene (or a derivative) from any desired species may be used, in preferred embodiments, the gene which is from the same species as the host is used. These were compared with ob/ob mice which have received adenovirus containing only a marker gene (β-galactosidase), those which did not receive gene therapy but which did receive injections of recombinant leptin, and to untreated controls. Further controls used in some of the experiments are db/db mice (obese, but unresponsive to leptin injections due to a receptor defecit), and lean mice (wild-type phenotype, genotype Ob/ob or Ob/Ob).

RESULTS OF THE PILOT STUDY

EXAMPLE 3

Figure 2:
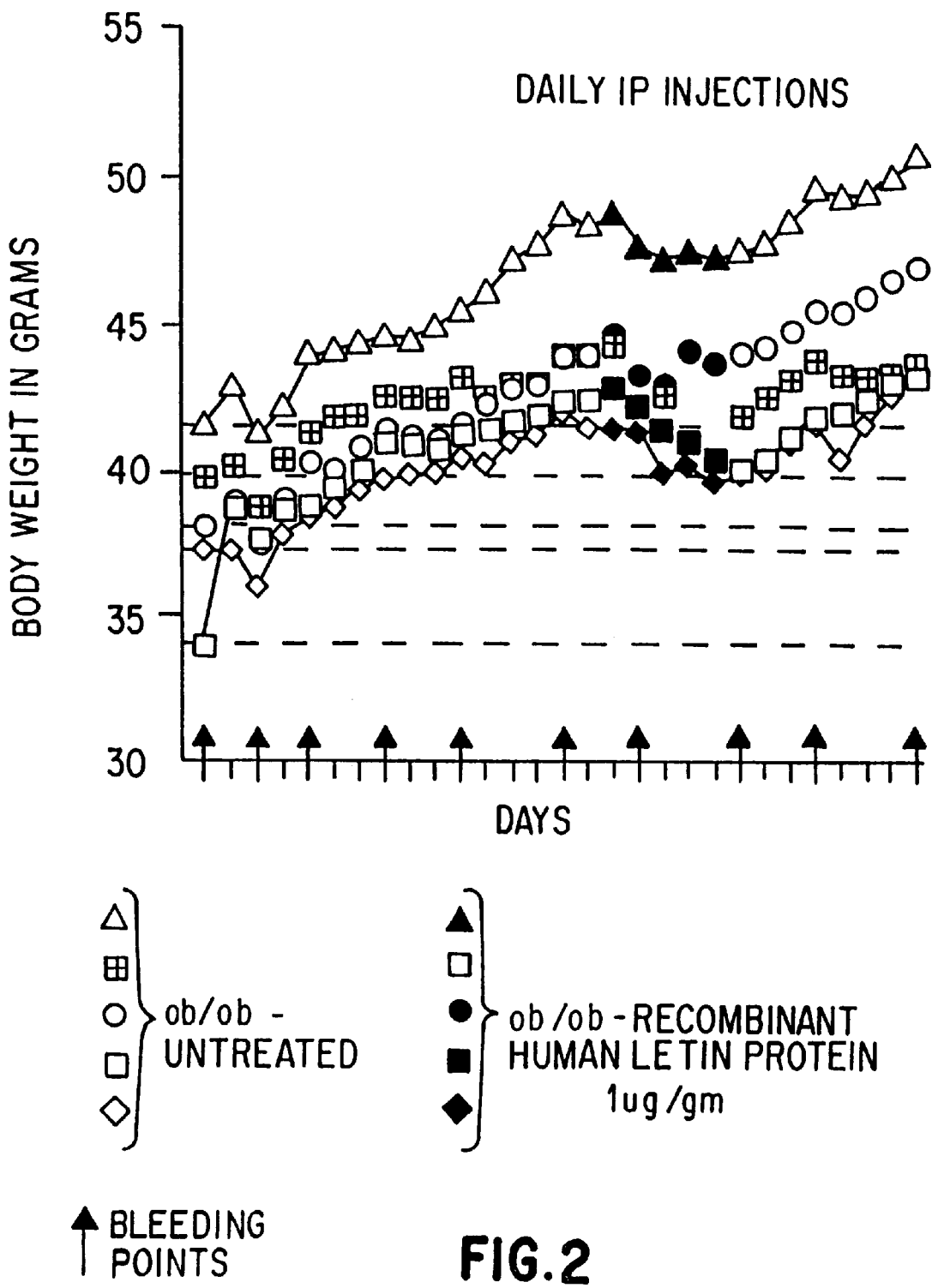
FIG. 2 is a graph showing the body weight changes of mice treated with recombinant human leptin protein as described in the Example 3 pilot study. Injections of human recombinant leptin were given daily IP, at 1 mg/gm body weight. Arrows indicate bleeding points.

Body-weight: FIG. 2 illustrates the body weight changes for the ob/ob mice of Example 3 ("pilot study") receiving 1 mg/gm body weight human recombinant leptin protein injections daily, compared to untreated controls. Animals receiving leptin were injected for five consecutive days, shown by the darkened symbols on the graph.

Figure 3:
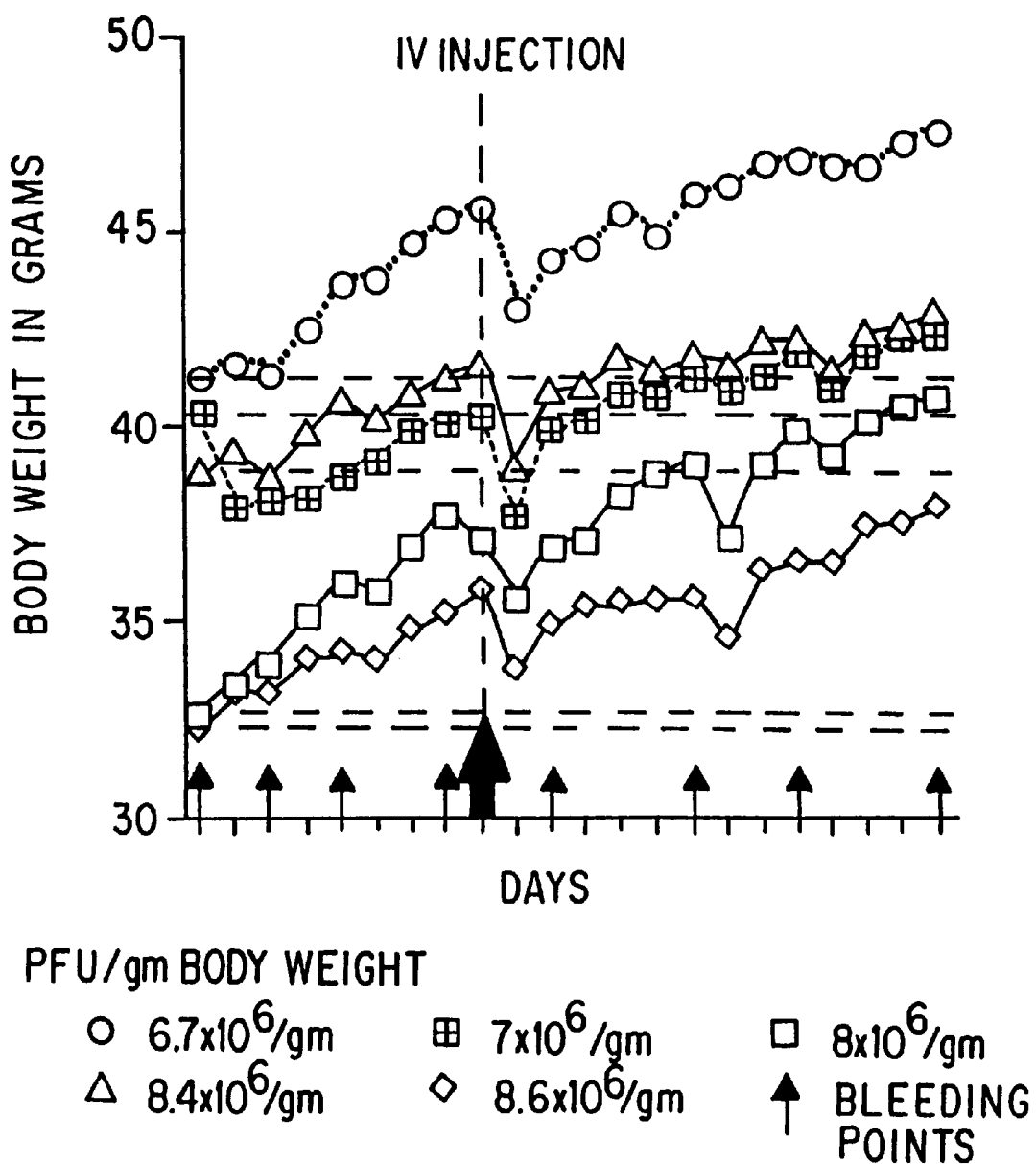
FIG. 3 is a graph showing body weight changes of mice of the pilot study treated with adenovirus carrying a reporter gene (βgalactosidase), used as a control.
Figure 4:
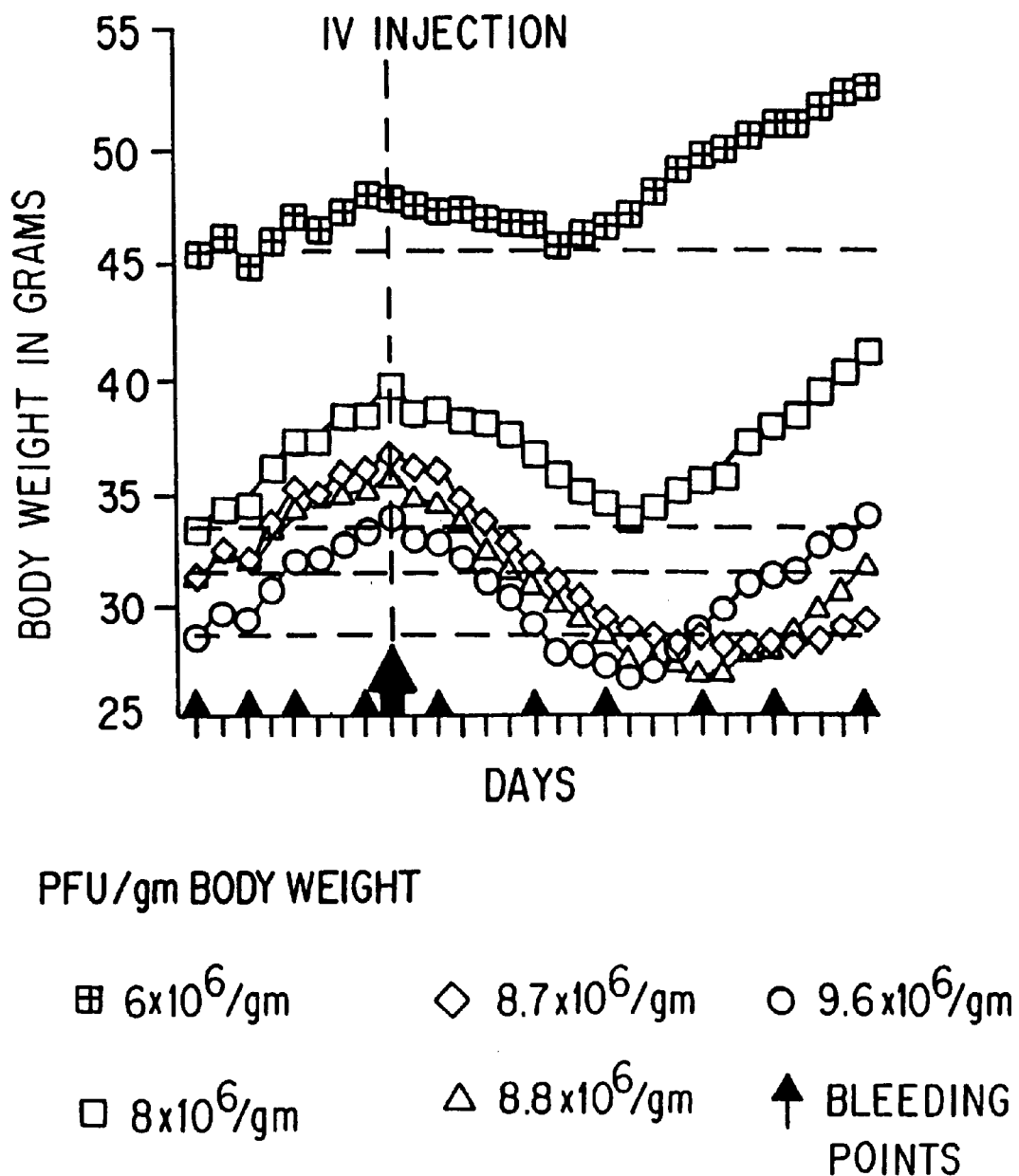
FIG. 4 is a graph showing body weight changes of mice of the pilot study treated with adenovirus carrying the human leptin gene.

All the animals receiving the leptin lost weight within 24 hours post-injection. All animals gained weight within 48 hours after the last IP injection. FIG. 3 illustrates the weight measured for these mice receiving various titers of an adenovirus carrying the reporter gene. All animals continued to gain weight post injection. FIG. 4 shows the results for the mice receiving an adenovirus carrying the leptin gene. As can be seen from the graph, all animals lost weight within 24 hours post injection. They continued to loose weight for 1–2 weeks post treatment. The injections were effective over a relatively large titer range, and a dose-effect was noted.

Figure 5:
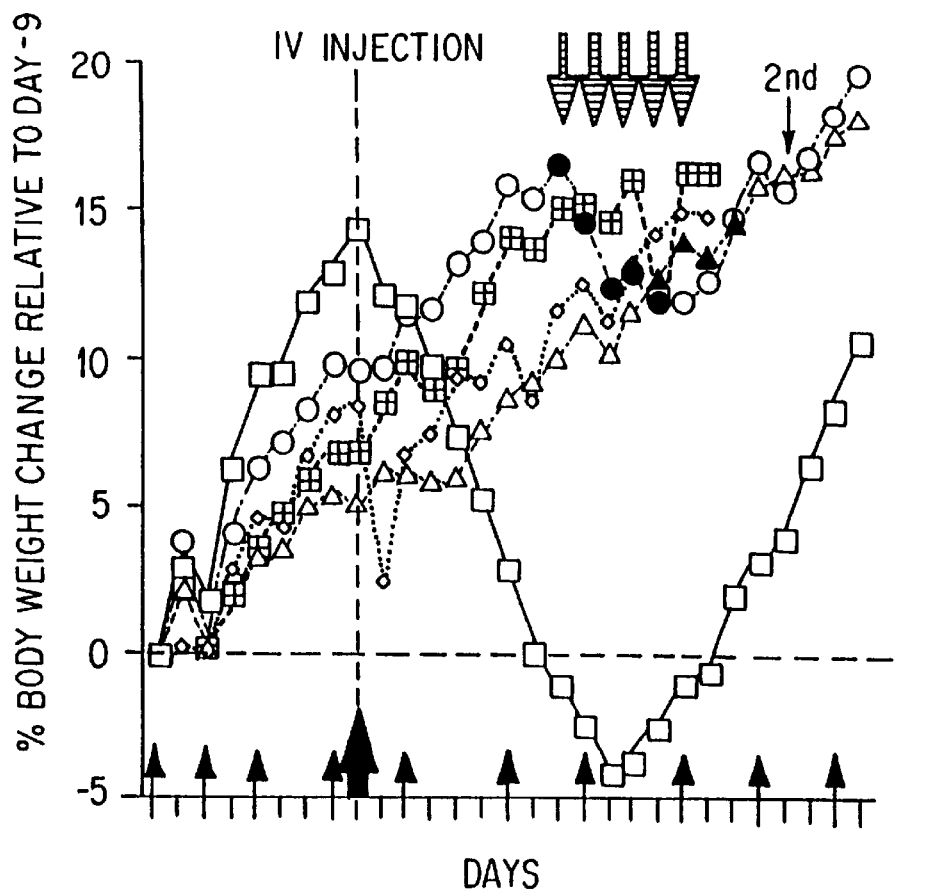
FIG. 5 is a graph showing the percent of body weight changes for all groups of mice of the pilot study.
Figure 5:
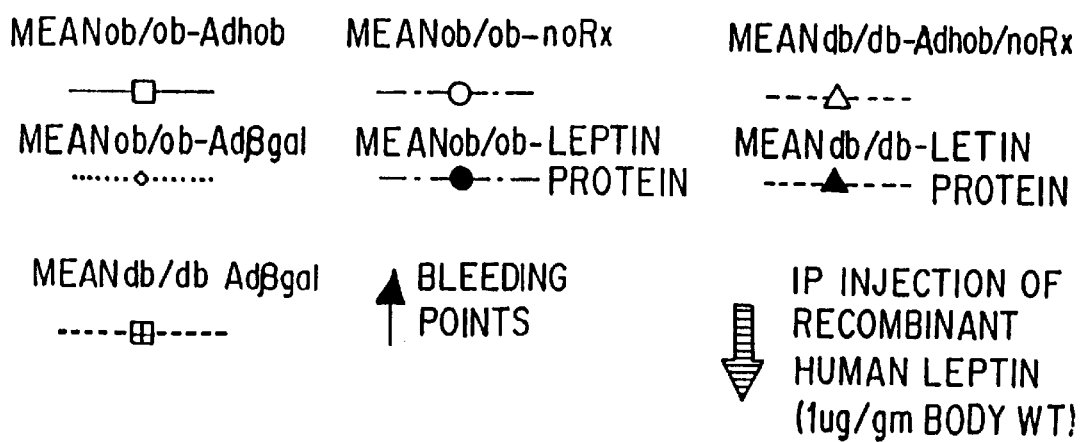

Along with absolute changes in weight, the percentage body weight change was calculated for all groups in the pilot study. In the animals treated with recombinant leptin injections, weight loss plateaued at day three, and from day 1–5 post treatment, a 4.7% loss in body weight was noted. For mice treated with the vector carrying the leptin gene, weight loss persisted over a 10–12 day period, and resulted in an 18.61% loss in body weight. Furthermore, over days 1–5 post treatment, a 9.17% loss in body weight was observed compared to only 4.7% loss in the recombinant leptih treated mice. This is illustrated in FIG. 5.

Leptin: The amount of human leptin in plasma was measured in the pilot study animals which received injections of human recombinant leptin and those which received the vector carrying the leptin gene. Those receiving the recombinant protein were noted to have leptin levels which were approximately 20-fold higher than the amount of leptin found in control (lean, wild type) animals; peak amounts of 399.8±40.91 ng/ml. Those receiving the leptin gene had levels of leptin in their plasma which was within the normal range found in a wild-type mouse (17.52±4.66 ng/ml). In both groups of animals of the pilot study, weight gain was synchronized with the fall of human leptin detected in the plasma. This is illustrated in FIG. 6.

Figure 7B:
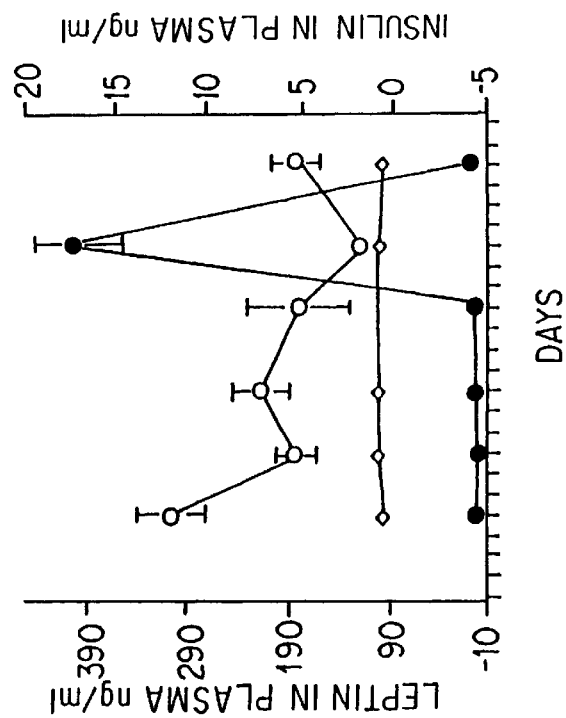
FIG. 7B (right graph) shows the amount of insulin and leptin in plasma of mice of the pilot study treated with recombinant human leptin injections.
Figure 7A:
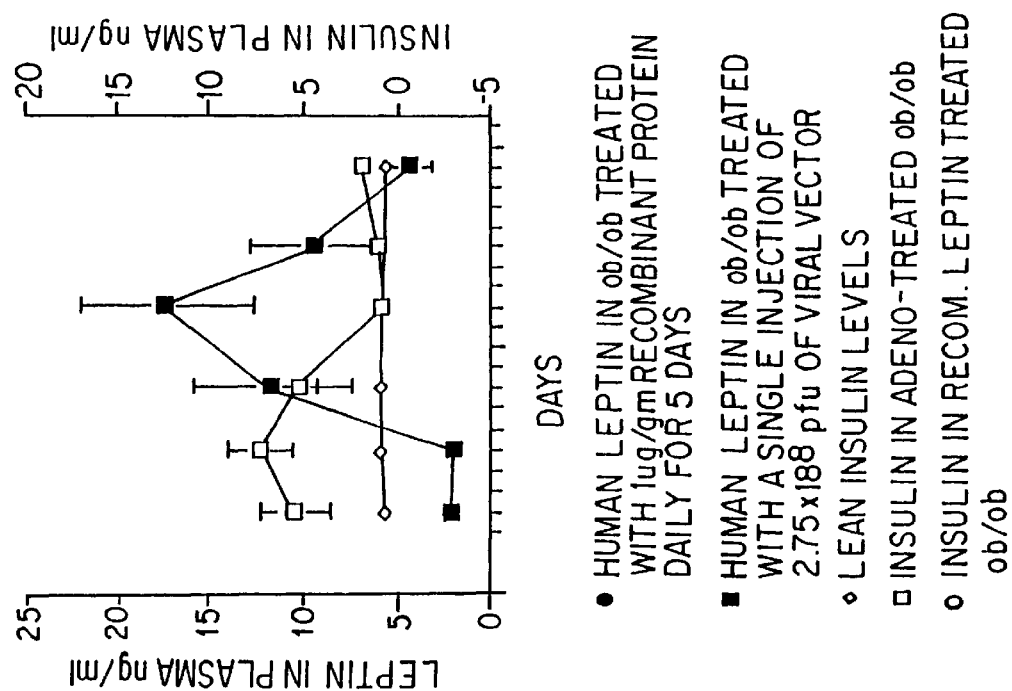
FIG. 7A (left graph) shows the amount of insulin and leptin in plasma of mice of the pilot study treated with adenovirus containing the leptin gene.

Insulin: The amount of insulin in the plasma was measured in the pilot study animals receiving recombinant protein and those which received the gene therapy. This is illustrated in FIG. 7. In both groups, insulin levels were observed to drop to those found in lean (wild-type) levels and was inversely correlated to leptin levels. In the mice receiving gene therapy, the low insulin levels were sustained for at least one week whereas in the recombinant leptin-treated mice, insulin levels increased to pre-treatment levels within 24 hours post injection.

Figure 8:
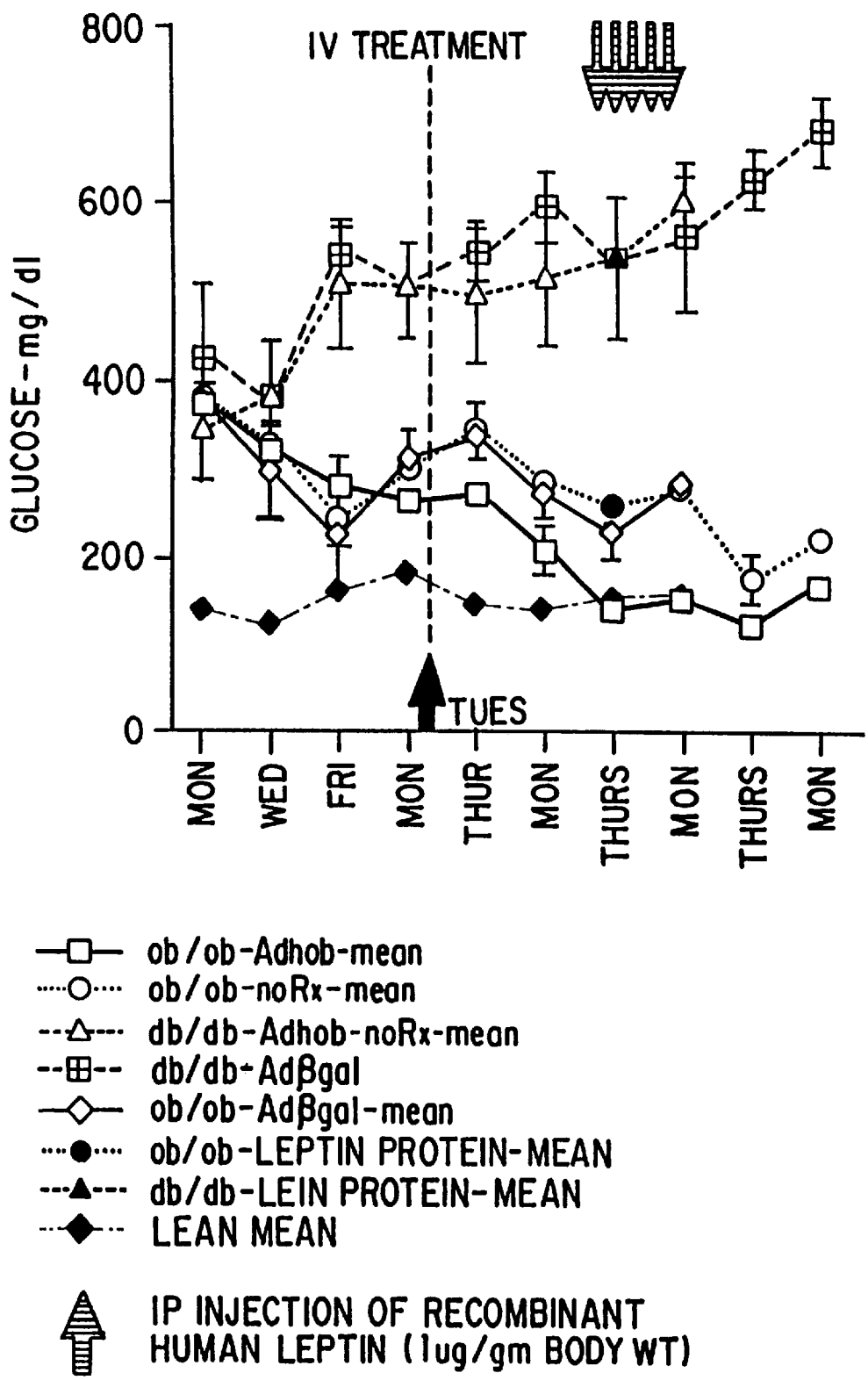
FIG. 8 shows glucose levels of the mice of the pilot study treated with either recombinant leptin, reporter gene or adenovirus containing the leptin gene.

Glucose: The levels of glucose in plasma was also measured in pilot study mice receiving recombinant leptin and those receiving the gene therapy treatment. In both of these groups, the glucose levels dropped within 6–9 days post treatment. The recombinant protein-treated mice did not achieve levels comparable to those found in lean, wild-type mice, and only sustained the lower level for less than one week. On the other hand, the mice which received the gene therapy had reductions in glucose levels to that of wild type lean mice, and they sustained this reduced level for at least two weeks. This is illustrated in FIG. 8.

RESULTS OF THE EXPANDED STUDY

An expanded study was also conducted, and is detailed in Example 5. This differed from the pilot study in that somewhat older animals were used, additional investigations were performed, and wild-type lean mice were also treated. The observations are set forth below.

Figure 9A:
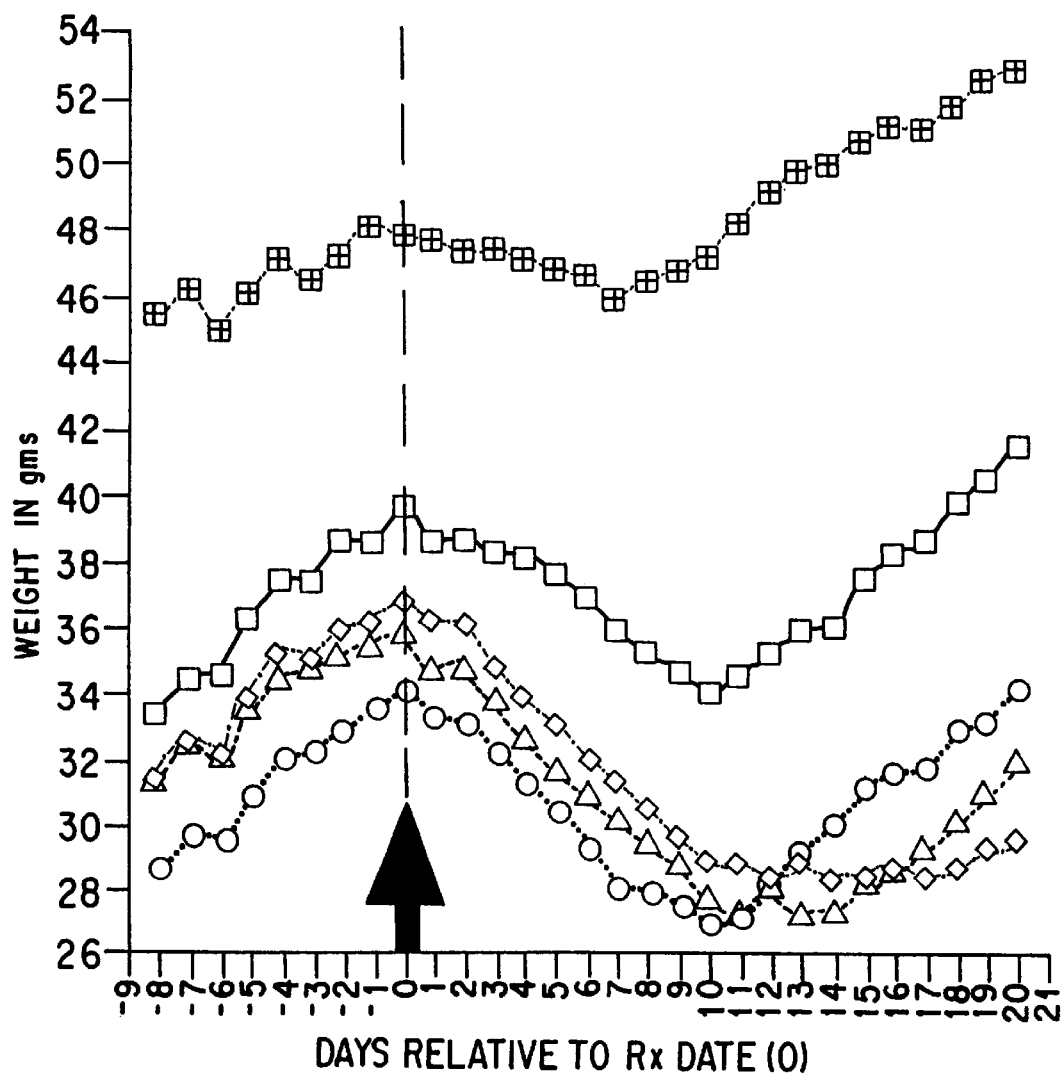
FIG. 9 compares body weight changes in the mice of the pilot study which received human leptin gene (FIG. 9A), with mice of the expanded study (Example 5) which received mouse leptin gene (FIG. 9B) and with mice of the expanded study which received human leptin gene (FIG. 9C).
Figure 9B:
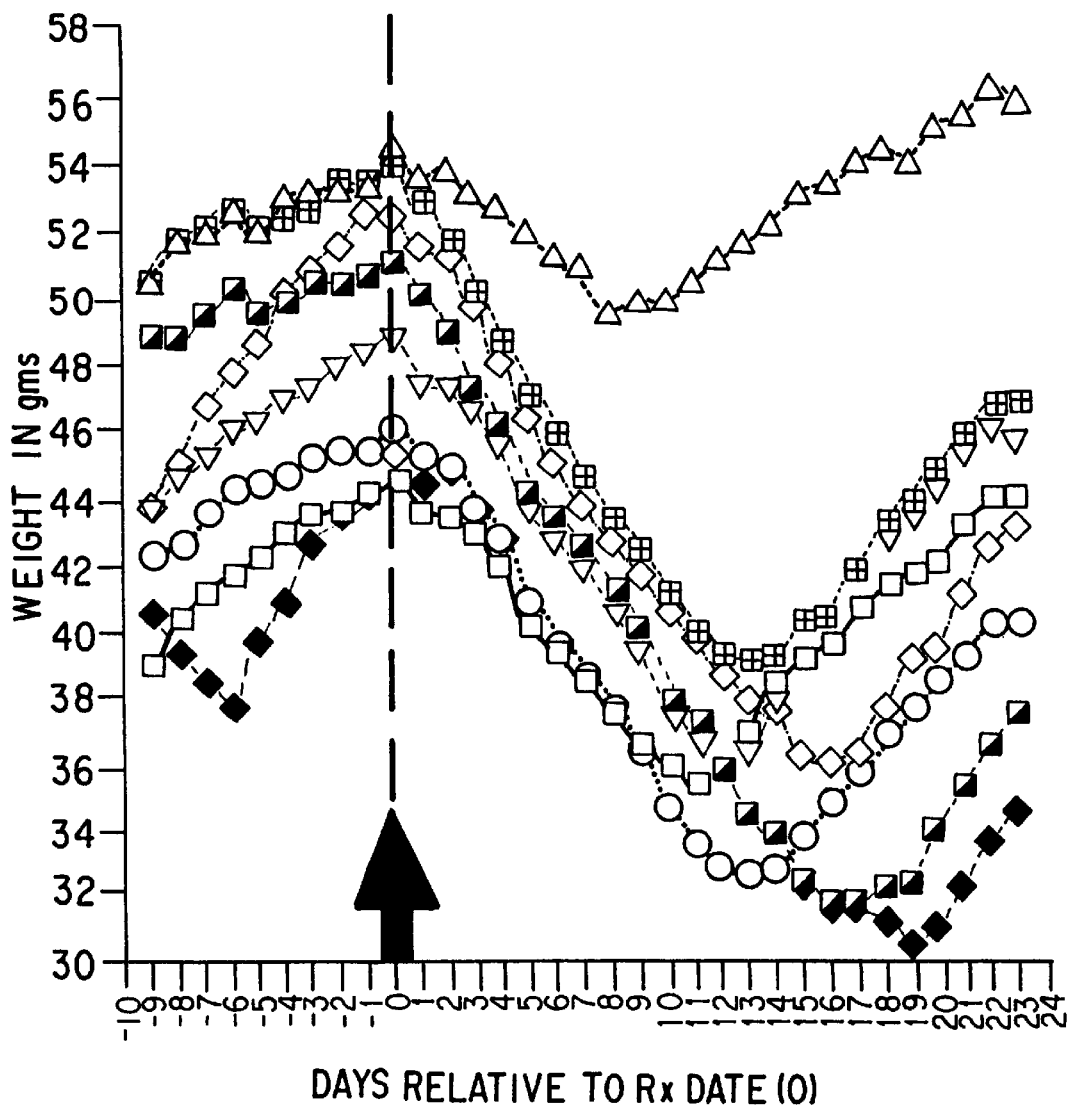
Figure 9C:
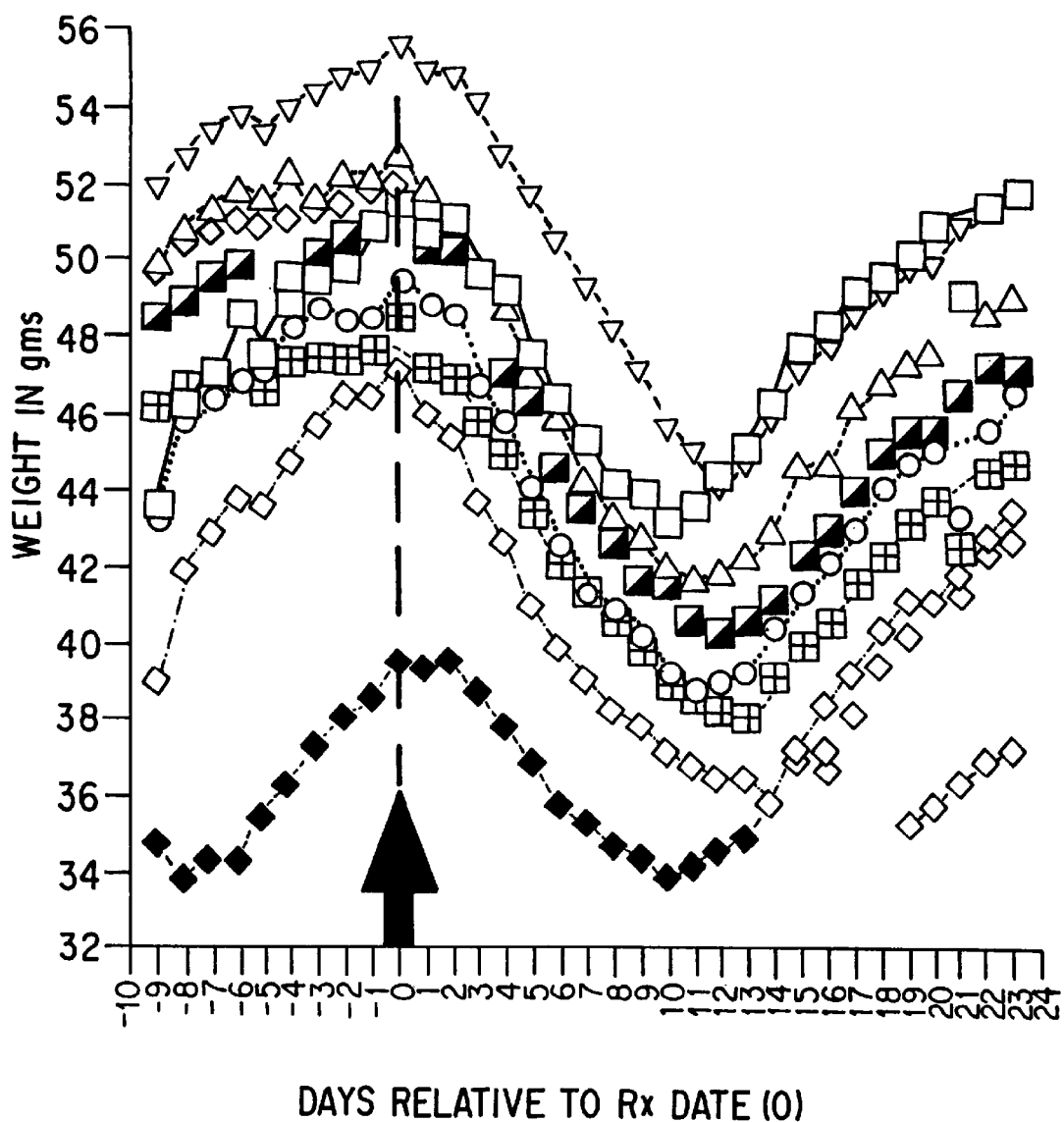
Figure 10A:
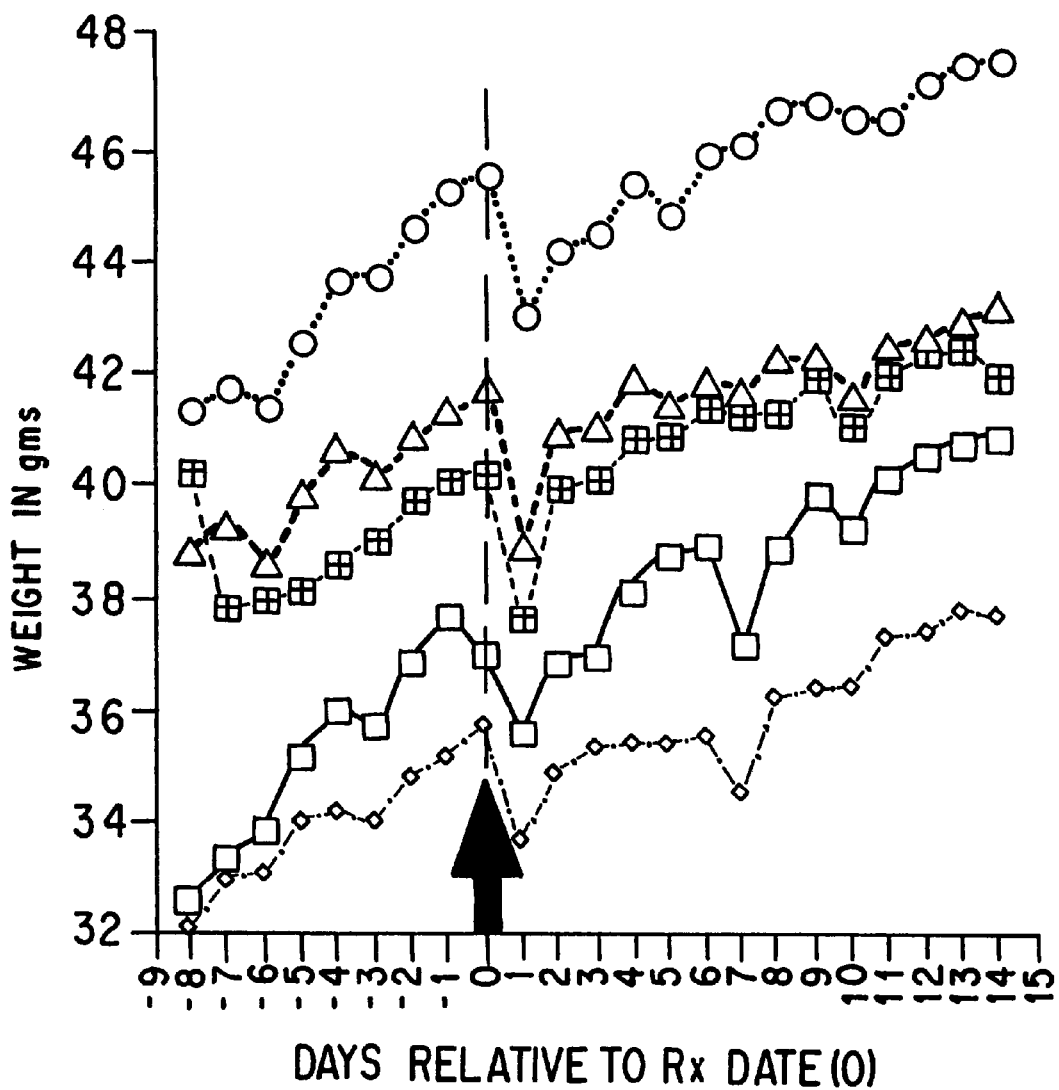
FIG. 10A is the pilot study mice.
Figure 10B:
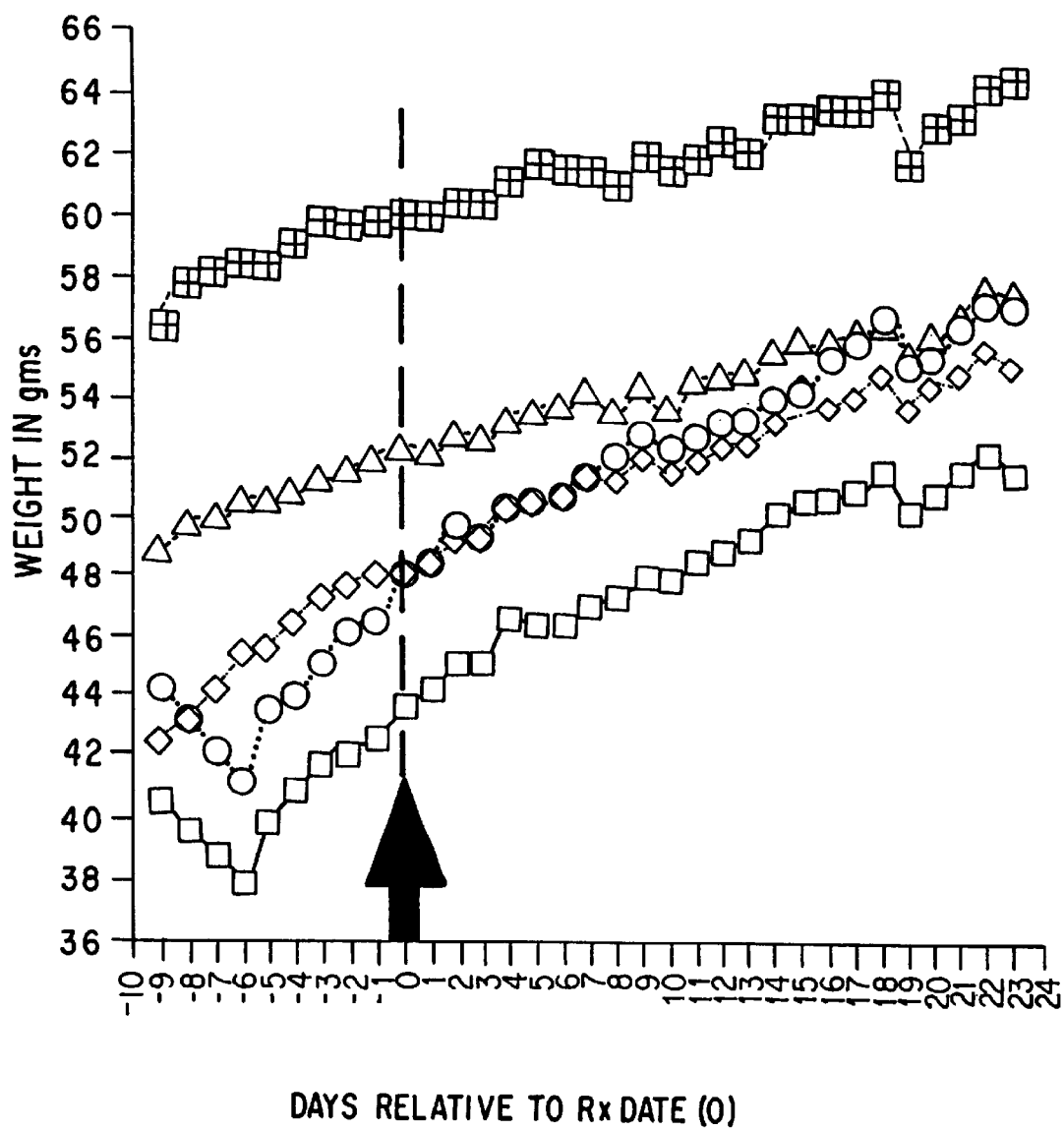
FIG. 10B shows the expanded study mice which received iv. injections of dialysis buffer.
Figure 10C:
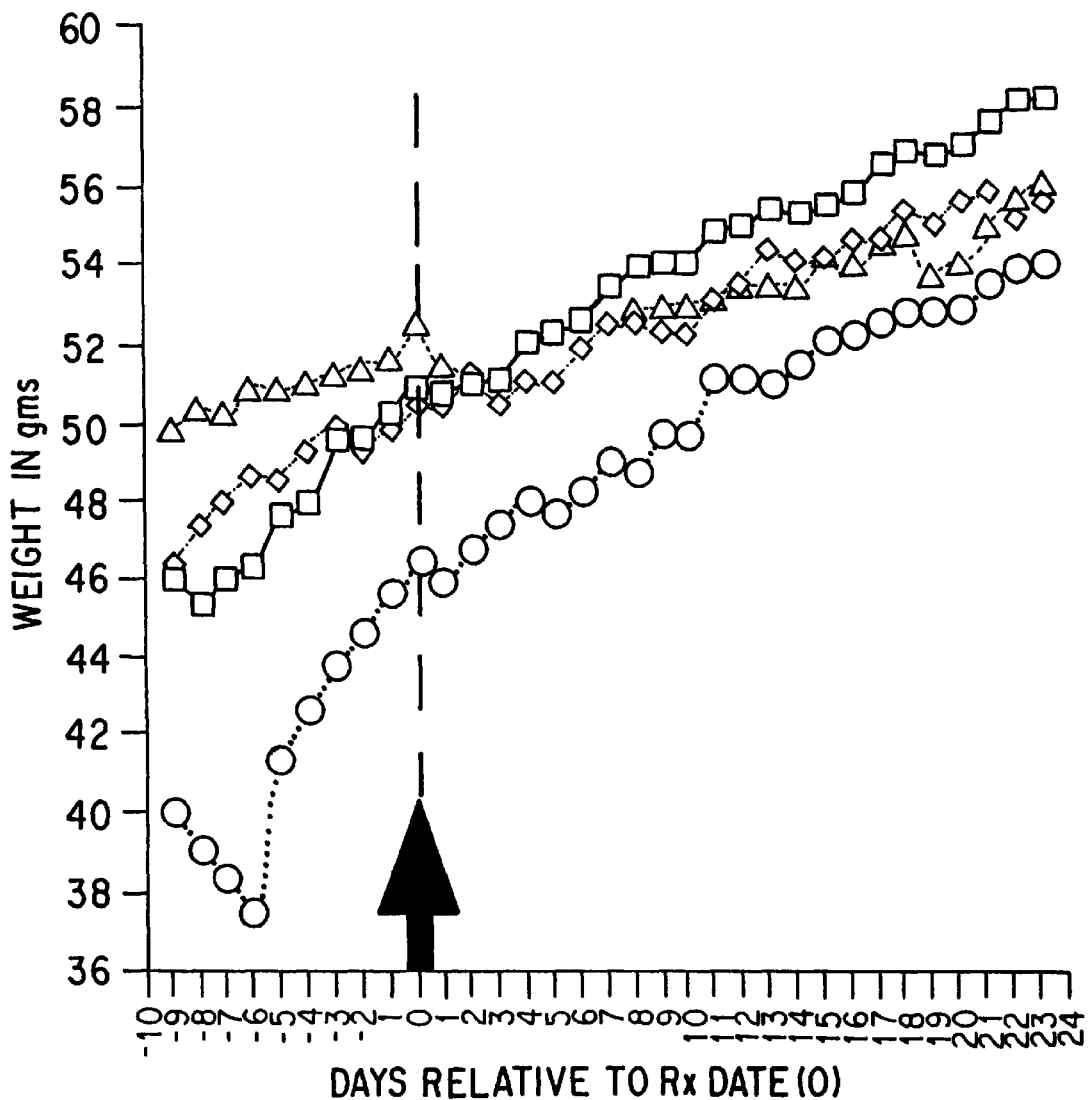
FIG. 10C shows the expanded study mice which received the control adenoviral injection. The arrowhead shows the first day that injections occurred. All controls gained weight.

Weight loss: The oblob mice which were treated with adenovirus carrying the human leptin gene lost weight, (18.61 % over a 10–12 day period) as did the mice in the pilot study, as is shown in FIG. 9. Weight loss occurred within 24 hours, with 9.17% loss from day 1–5 post treatment. Weight gain was restored within 10–20 days post-treatment. On the other hand, mice receiving control treatments continued to gain weight throughout the experiment, as did their counterparts in the pilot study, as shown in FIG. 10.

The ob/ob mice receiving iv injections of adenovirus carrying the mouse leptin gene lost more weight than did mice receiving iv injections of adenovirus carrying the human gene. The pattern of weight loss and time of weight gain were substantially the same as those receiving the human gene, however. This is shown in FIGS. 9B and 9C.

Figure 11A:
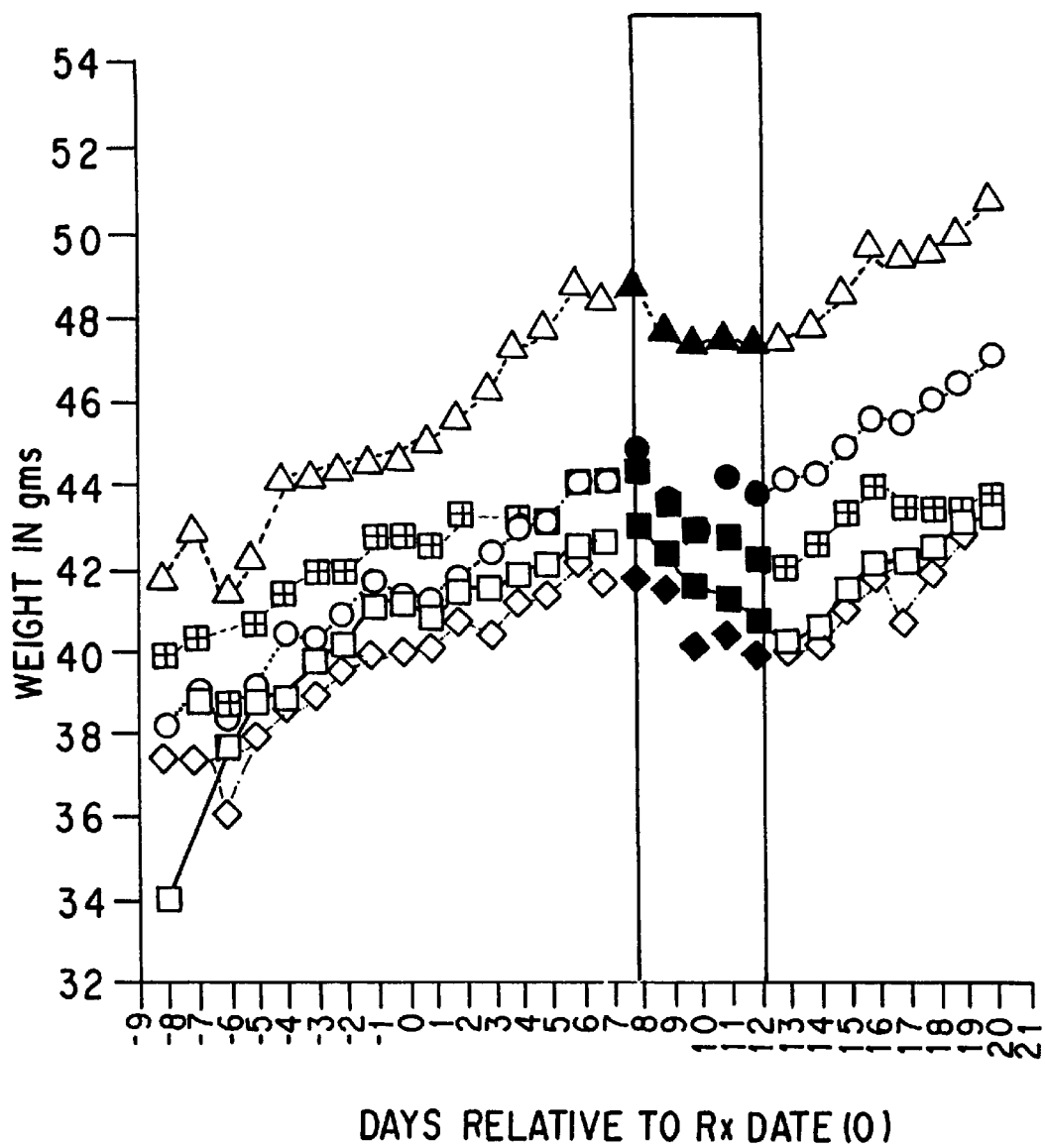
FIGS. 11A–C show the results of IP injections of human leptin.
Figure 11B:
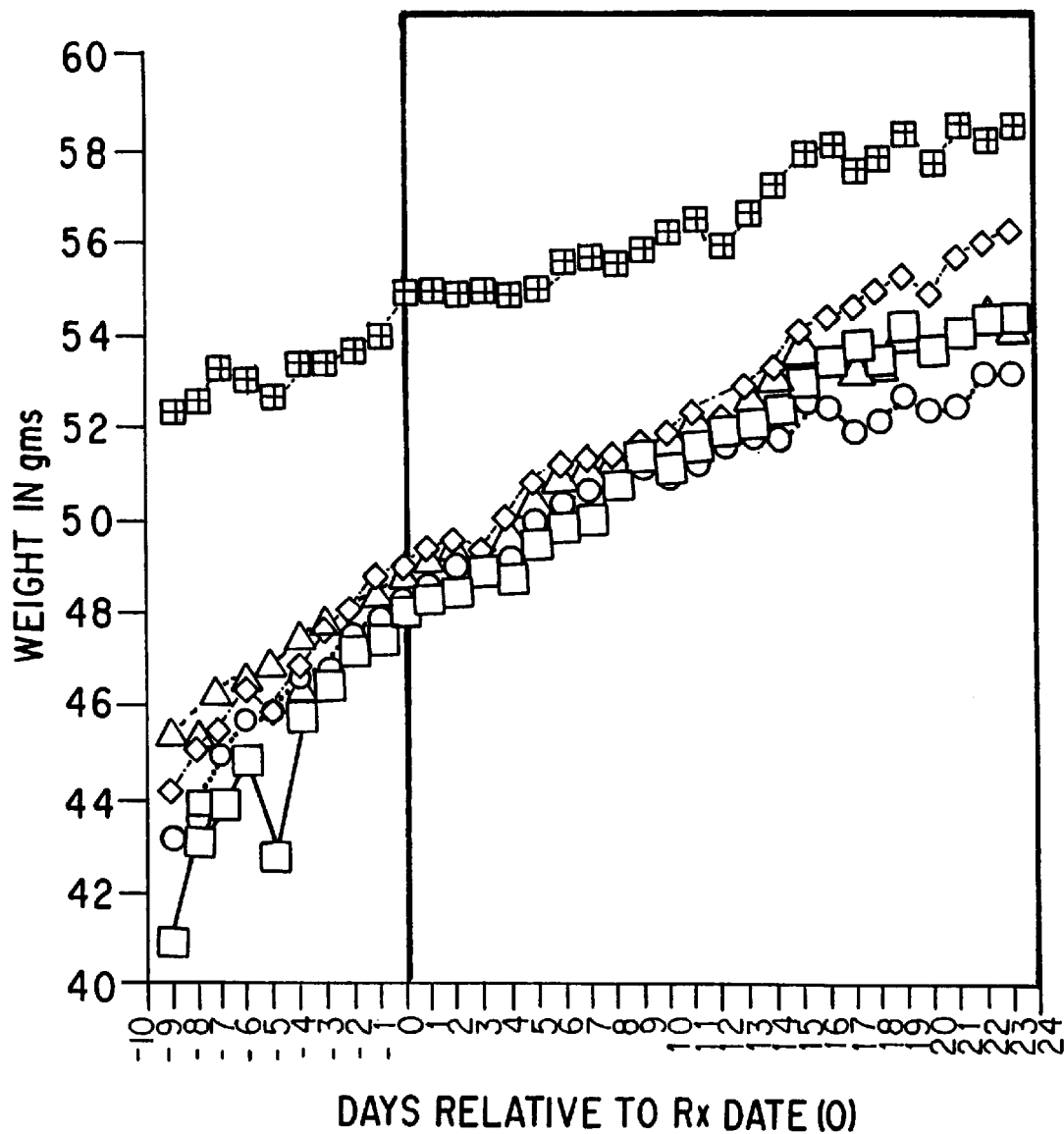
Figure 11C:
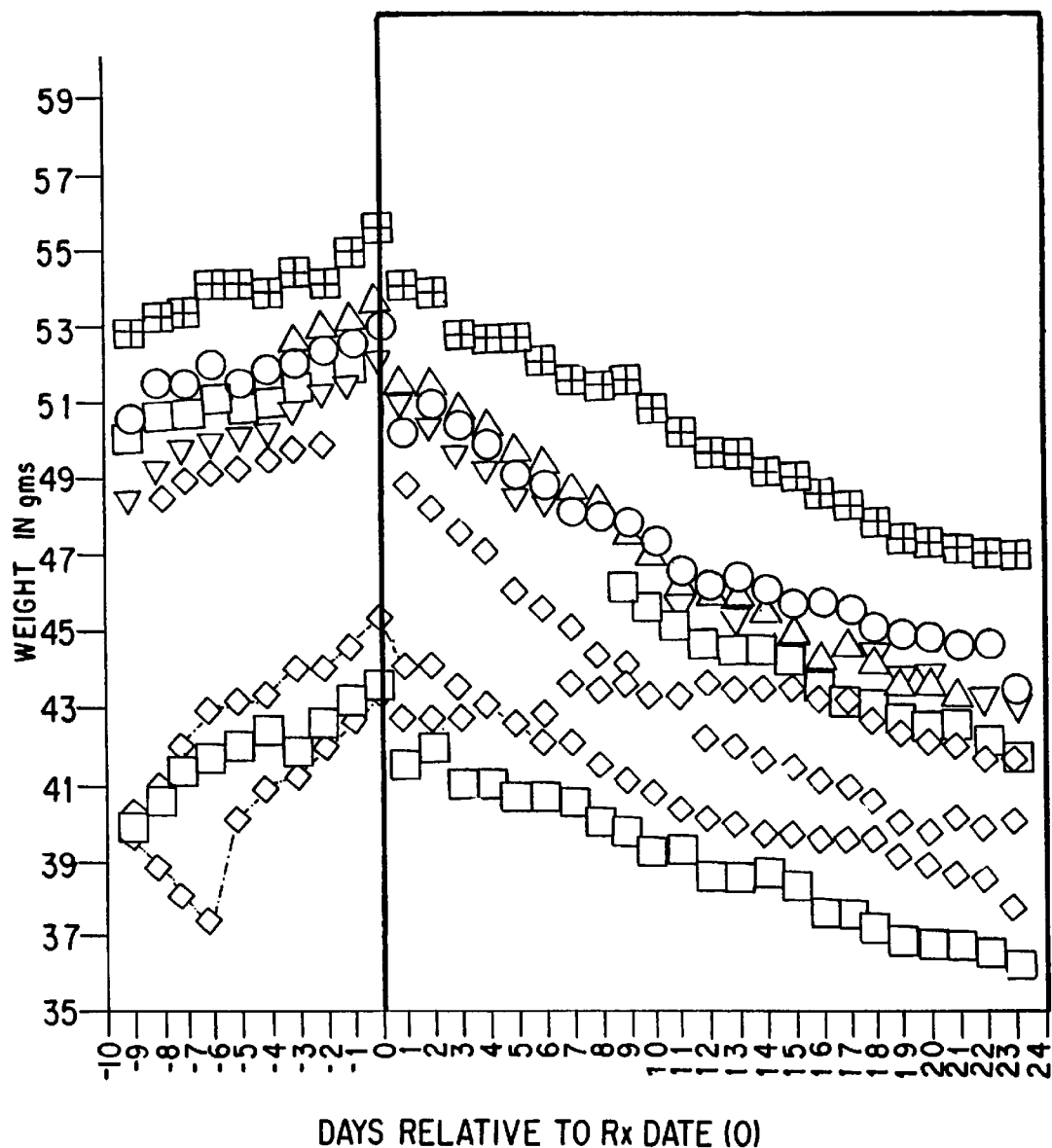

Mice receiving IP injections of recombinant leptin protein lost weight within 24 hours, and plateaued at day 3 of the daily injection, as illustrated in FIG. 11. After day 1–5 post-treatment, loss was 4.7%, significantly less than that of groups receiving gene therapy. Control animals gained weight throughout the experiment, as can be seen in FIGS. 11B and 11C.

Figure 12:
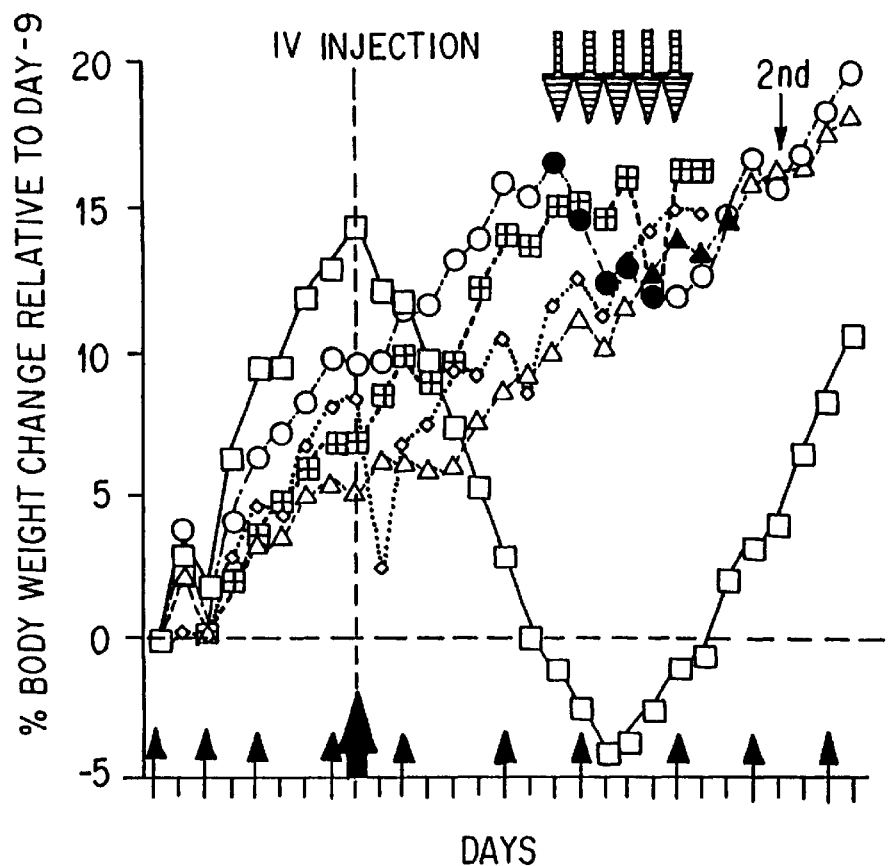
FIG. 12 is a graph summarizing percent body weight changes for all the treatment groups of the expanded study.

A summary of the percent of body weight changes is given in FIG. 12. The noteworthy points are as follows:

ob/ob mice which were treated with the reporter vector, and db/db mice which were treated with , β-gal, the ob gene vector or recombinant protein all continued to gain weight post-treatment.

ob/ob animals which were treated with adenovirus carrying human leptin gene or which were treated with recombinant leptin lost weight within 24 hours post injection.

In ob/ob mice treated with adenovirus containing a human leptin gene, the observed weight loss persisted over a 10–12 day period and resulted in an 18.61% loss in body weight. In day 1–5 post treatment, there was a 9.17% loss in body weight.

In ob/ob mice treated with recombinant leptin, weight loss plateaued at day 3 of the daily injection (1 mg/gm). In day 1–5 post treatment a 4.7% loss in body weight was observed.

Weight gain observed in the mice treated with the human leptin gene resumed after 10–12 days post treatment at a rate identical to that observed pre-treatment.

Figure 13:
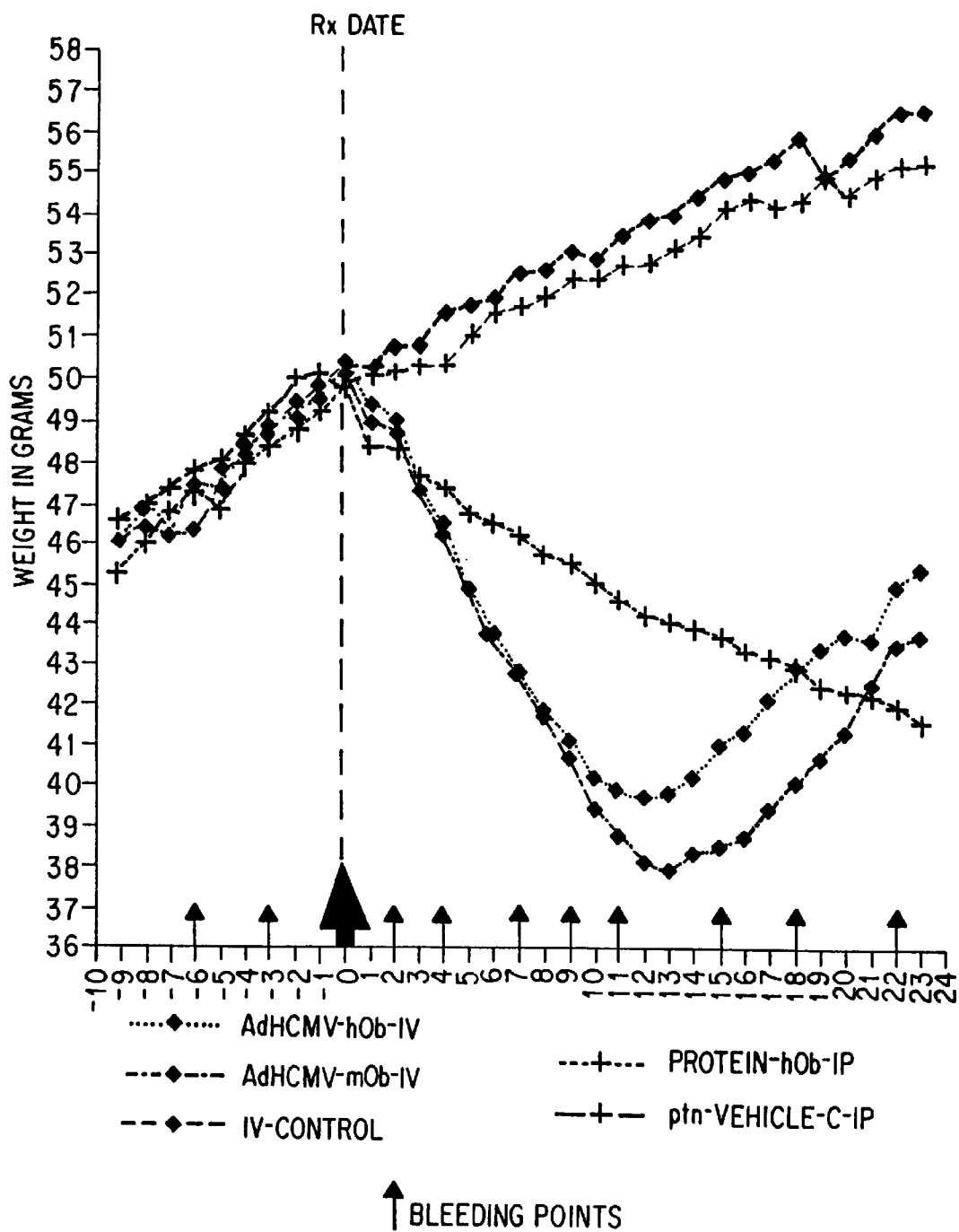
FIG. 13 is a graph summarizing the mean body weight changes for the ob/ob mice in the expanded study.

The summary of the mean changes in body weight of oblob mice are presented in FIG. 13. Table 1, below presents the percent weight change as calculated over various time periods post treatment.

TABLE 1

| % Weight Change Post Treatment | Days 1–5 | Day 8 | Day 12 |
| --- | --- | --- | --- |
| iv. leptin gene | −10.27 | −16.52 | −22.2 |
| iv. control | +3.25 | +4.46 | +7.1 |
| IP leptin protein | −6.46 | −8.58 | −11.62 |
| IP control | +3.41 | +4.33 | +5.9 |

It was also found that there was a greater response when the adenovirus carried the mouse leptin gene than when the human leptin gene. Both of these treatments had a greater response that the IP injection of leptin protein.

Administration of IP leptin led to a response similar to that seen in the pilot study. A sharp drop in weight in the first three days was observed which was substantially identical to that observed for the gene-treated animals. This was followed by a moderation in weight reduction in the IP protein treated animals, and a bifurcation in weight reduction slopes for both treatments.

As was seen in the pilot study, the adenoviral-mediated effect was transient, and weight gain was observed at day 11–12 post treatment for the iv. injected animals and day 8 post treatment for the IM injected animals. While not wishing to be bound by theory, it appears that this is due to an immune response to the adenovirus and or adenoviral genes, and not due to an immune response to the leptin produced.

Figure 14B:
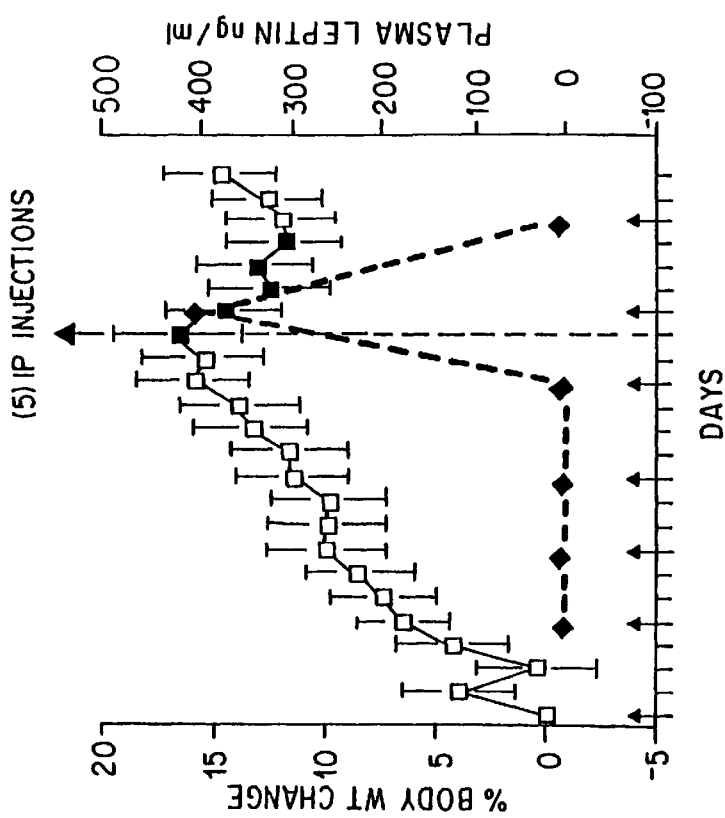
FIGS. 14A–B summarize the levels of human leptin found in the plasma of mice in the expanded study.
Figure 14A:
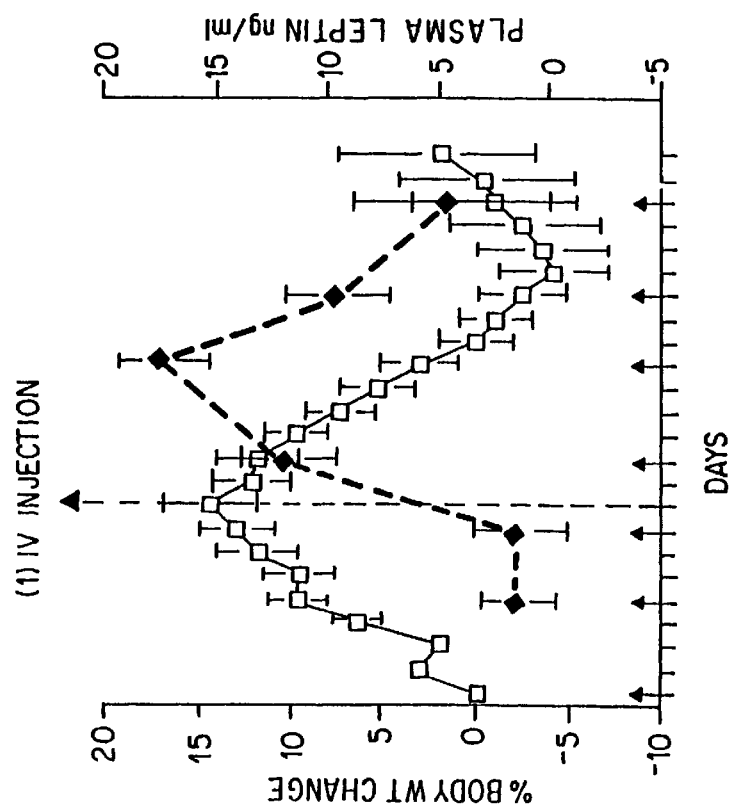
Figure 15A:
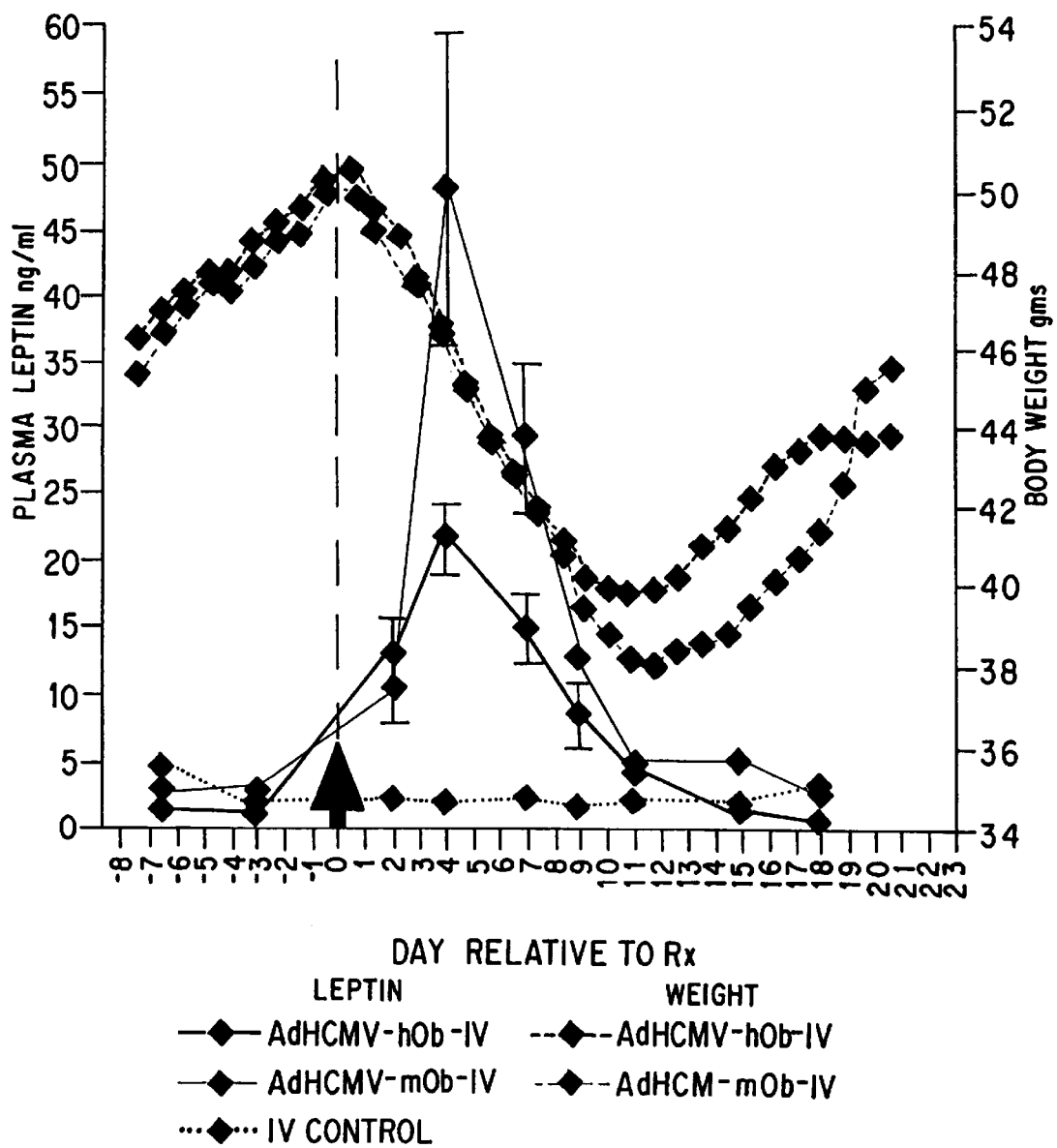
FIGS. 15A–B summarizes findings relating to the injection of recombinant leptin in the expanded study.

Leptin levels: Levels of leptin in blood plasma were studied in each of the mice groups, and is illustrated in FIG. 14. Those which were treated with the adenovirus carrying the human leptin gene (FIG. 14A) had levels which were within the normal range found in wild-type mice (averaging 12.5 ng/ml). In the group treated with recombinant protein (FIG. 14B), levels of human leptin exceeded wild-type by about 20-fold; for mouse leptin, concentration exceeded wild type by about 10-fold (FIG. 15A). Weight gain was observed to be synchronized with the fall of leptin levels in plasma.

Figure 15B:
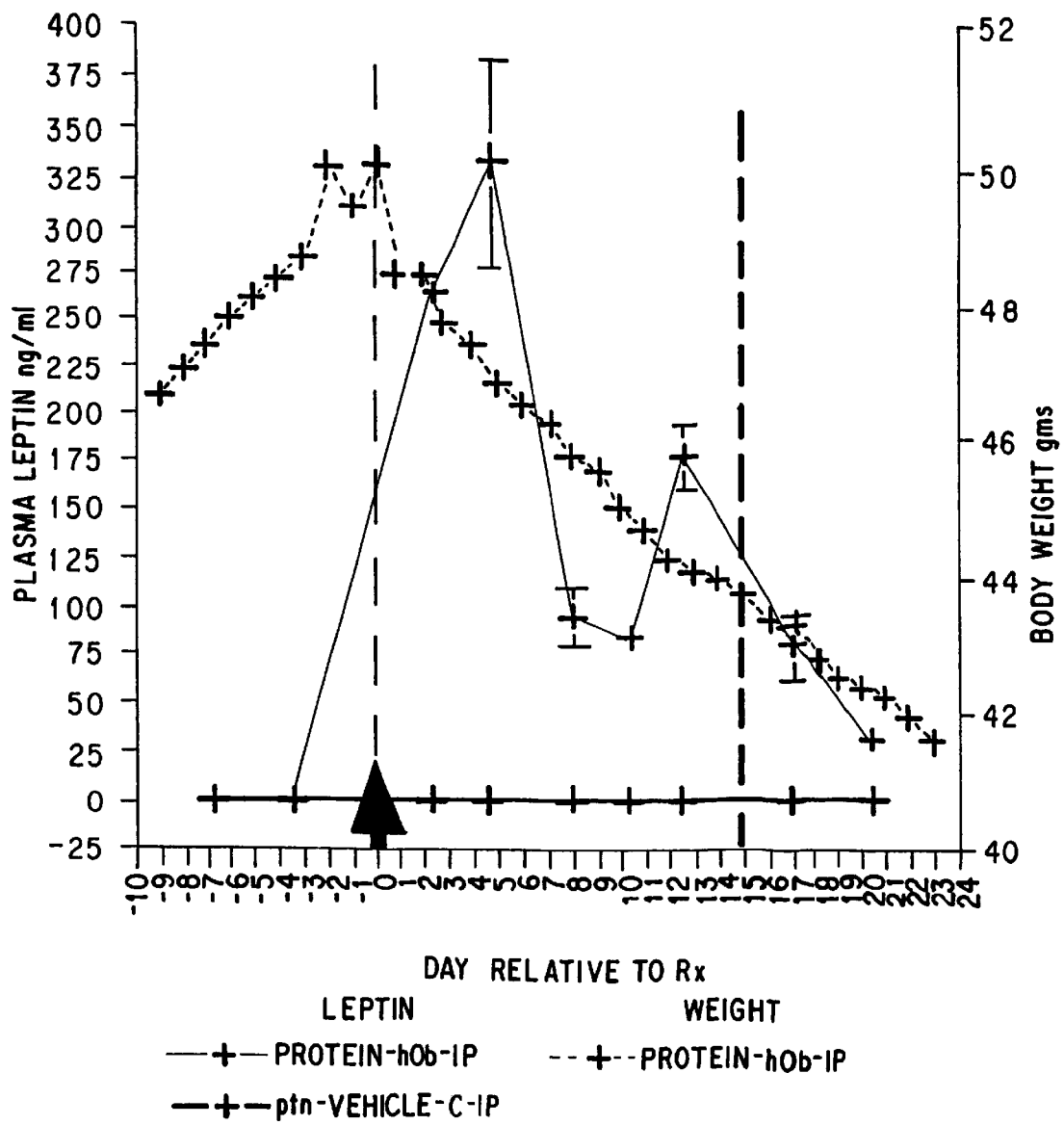

Recombinant Leptin injections: In the expanded study, leptin IP injections were continued daily over a longer time. Results were similar to those in the pilot study, however, and a summarized in FIG. 15. The weight loss associated with the adenovirus treatment at any point prior to day 10–12 was about twofold greater than that observed with the leptin IP treatment. Peak plasma concentration of leptin was 20- and 10-fold higher in leptin IP treated groups than in the groups treated with adenovirus carrying the human and mouse genes, respectively. The uninterrupted daily protein injections continued to be associated with weight loss to at least day 24.

Figure 16:
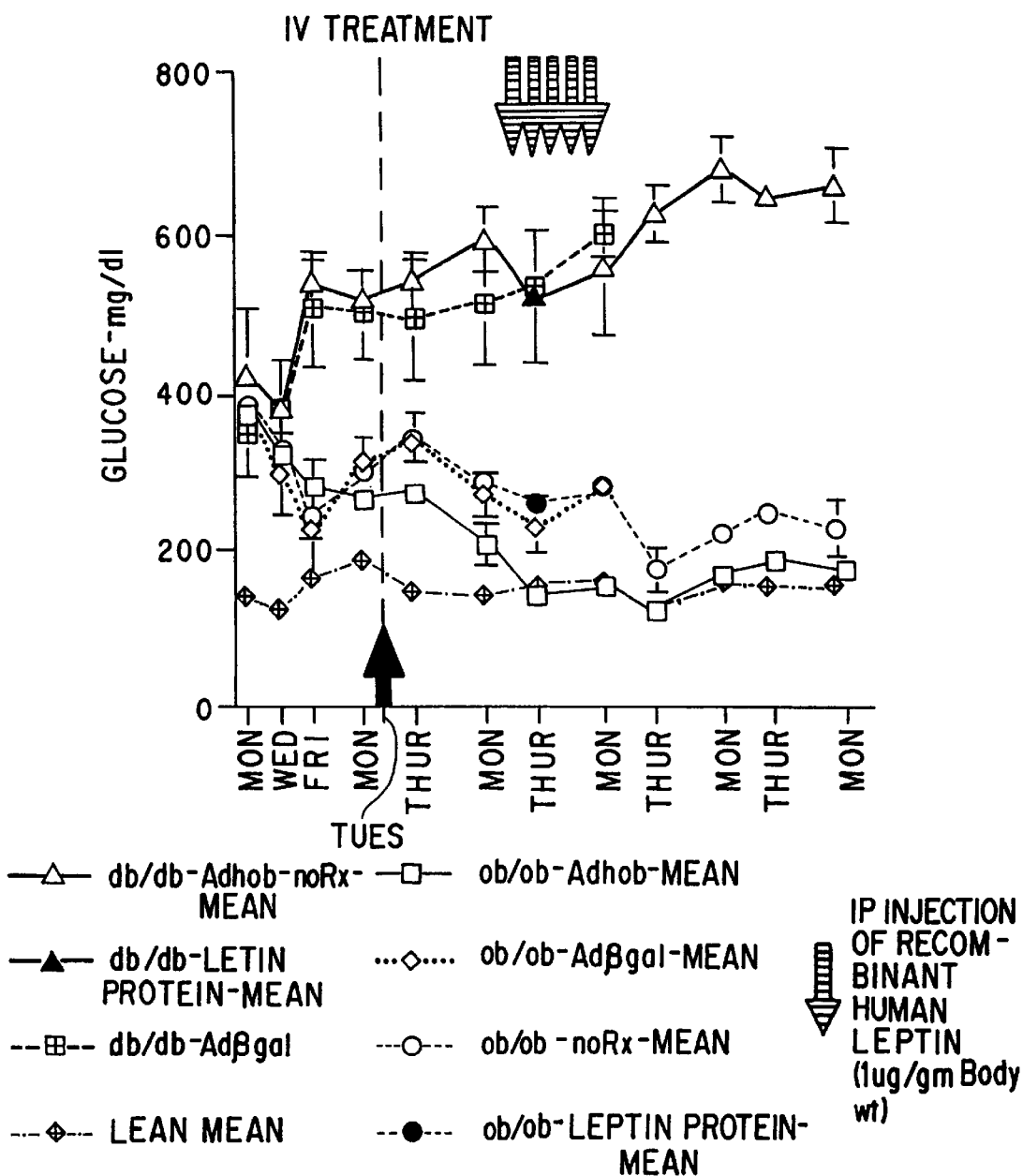
FIG. 16 is a graph illustrating glucose levels of animals in the expanded study.
Figure 17A:
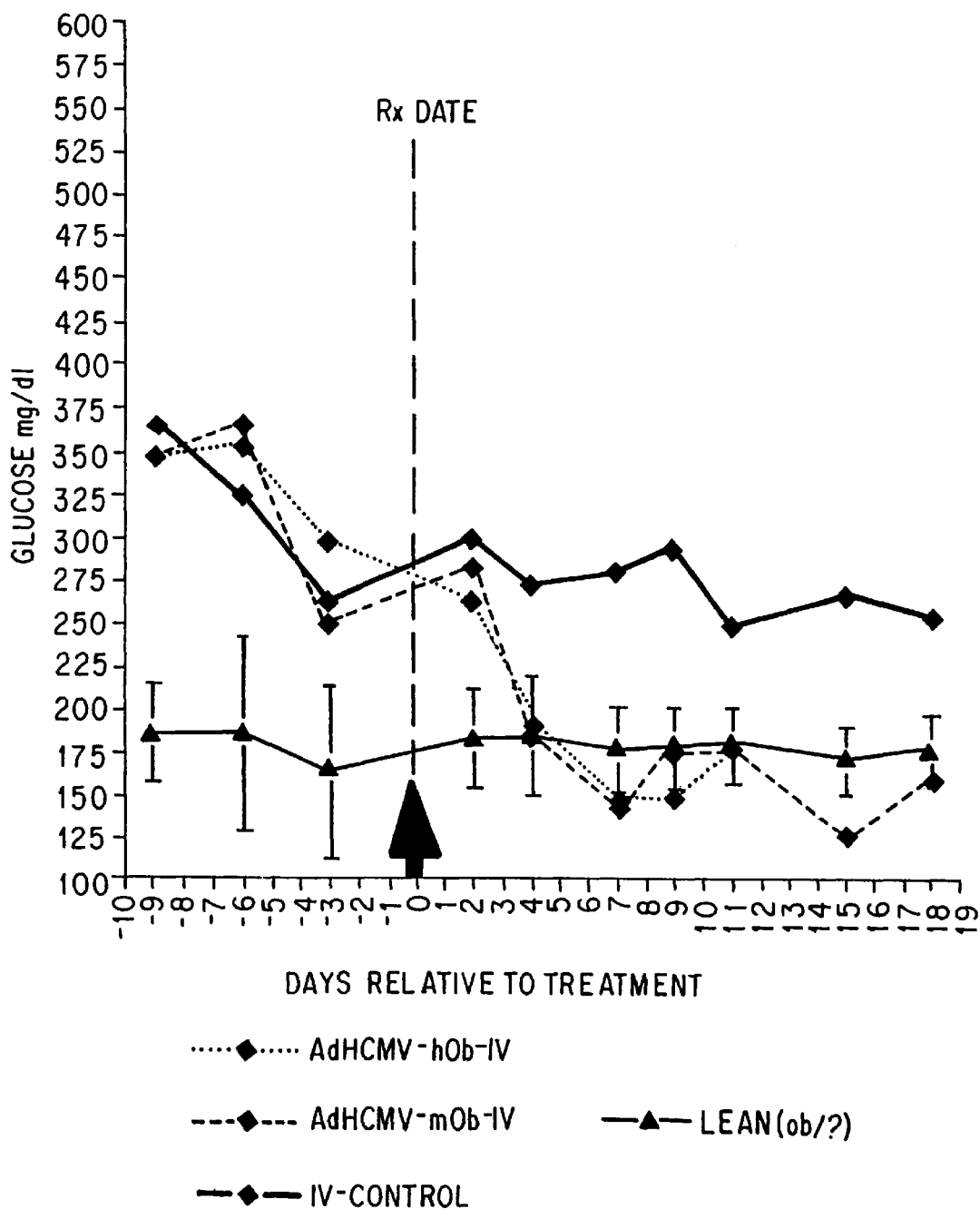
FIG. 17A shows glucose levels in adenovirus-treated mice in the expanded study and FIG. 17B shows the same in mice receiving protein injections.
Figure 17B:
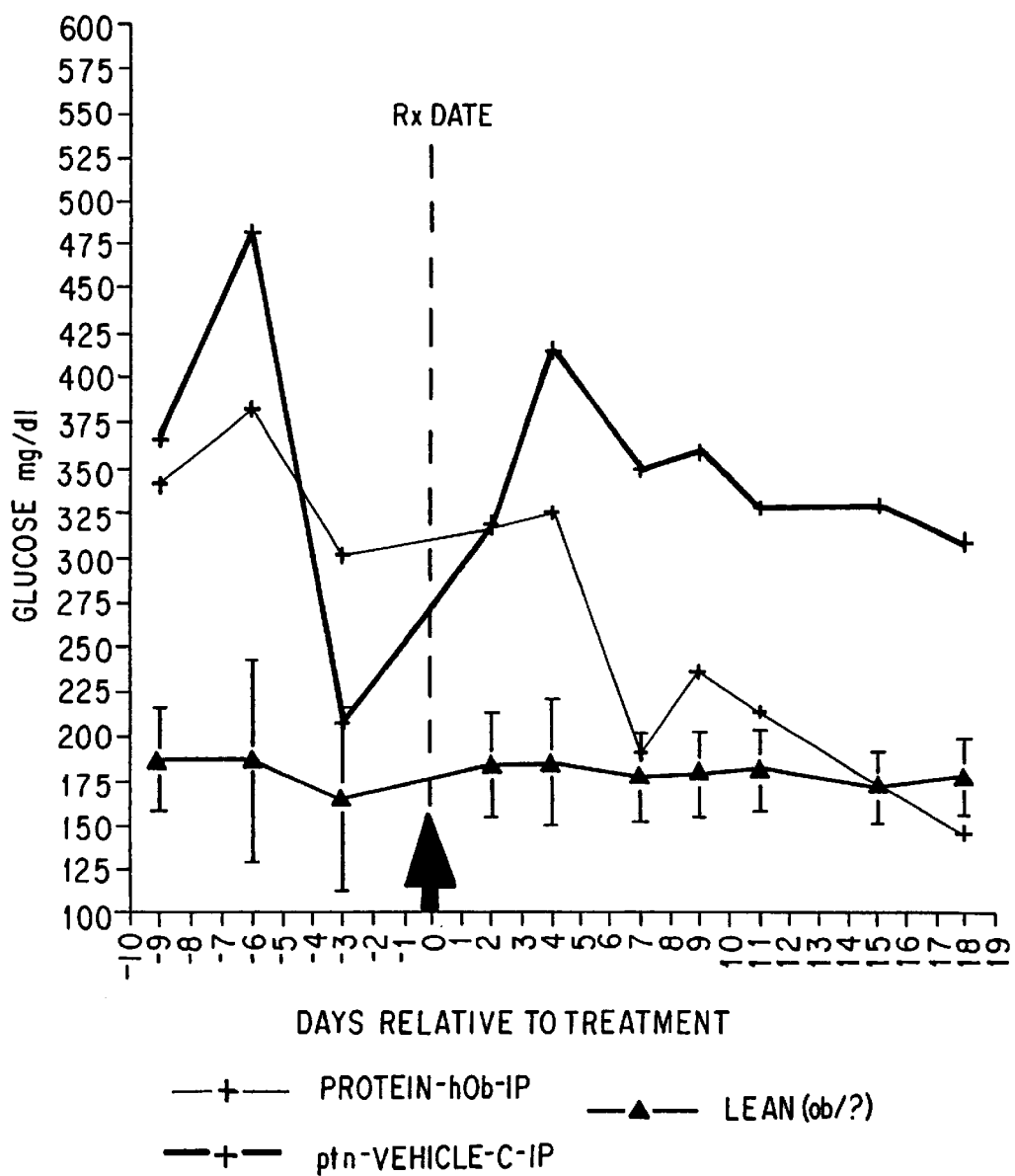

Glucose levels: The glucose levels dropped within 6–9 days post-treatment in mice receiving adenovirus carrying the leptin gene and receiving recombinant injected leptin. (See FIGS. 16, 17A and 17B). No change in glucose levels were observed in any control treated mice. The only treated group whose glucose levels reached that of normal (lean) mice were the mice receiving adenovirus carrying the human leptin gene, and the normal glucose levels was sustained for at least two weeks. Mice receiving recombinant leptin injections sustained reduced glucose levels for less than one week.

Figure 18:
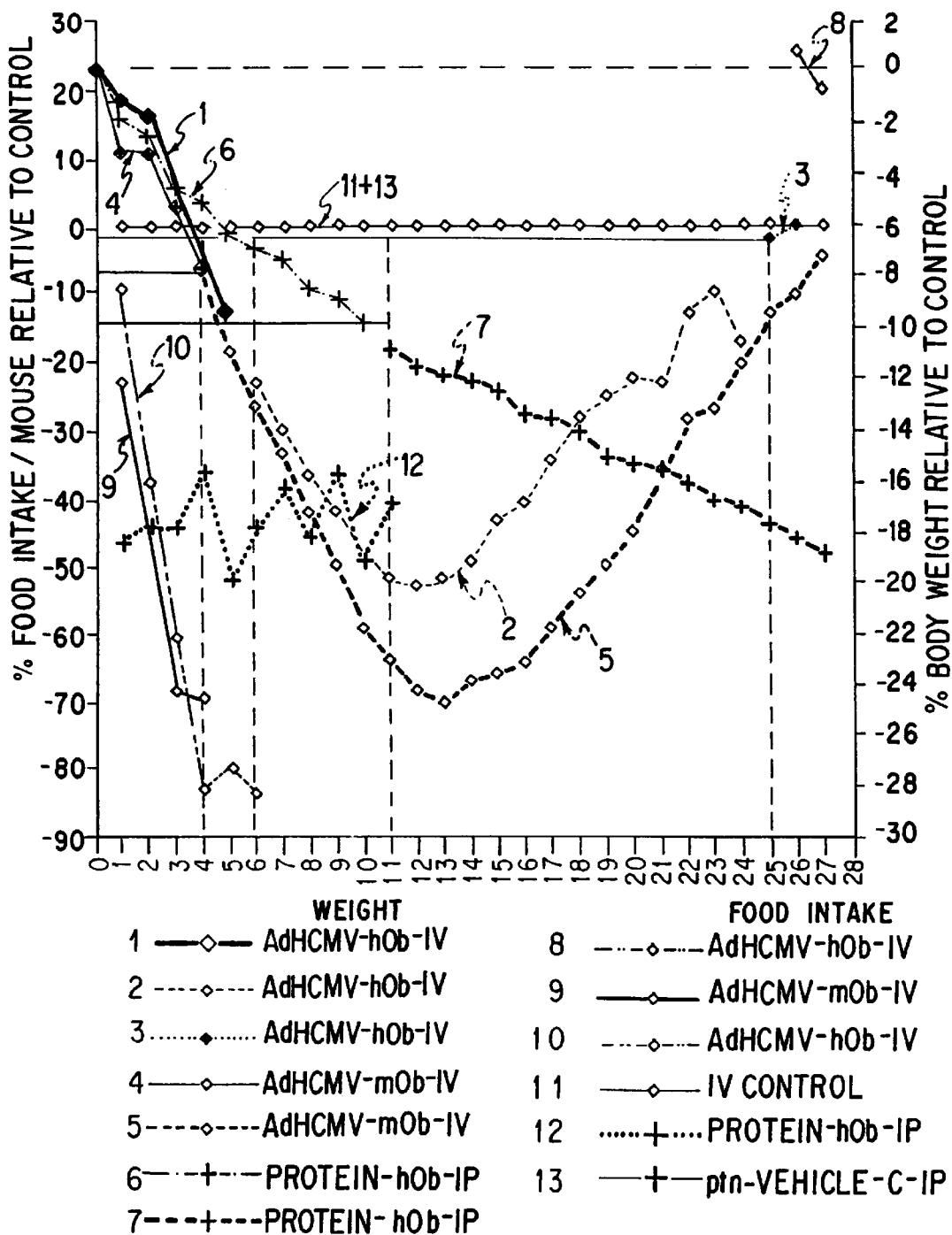
FIG. 18 shows food intake in relation to weight loss for the expanded study.

Food intake: An attempt was made to measure food intake, and is shown in FIG. 18. Accurate measurements in the group receiving adenovirus carrying a leptin gene and in the group receiving human recombinant leptin was not possible after about one week, as the animals became hyperactive and spilled food out of their containers. In the group receiving adenovirus carrying the human leptin gene, food suppression was 76.6% ±6.75, whereas in the group receiving recombinant human leptin injections, suppression was 43.8%±4.8.

Figure 19:
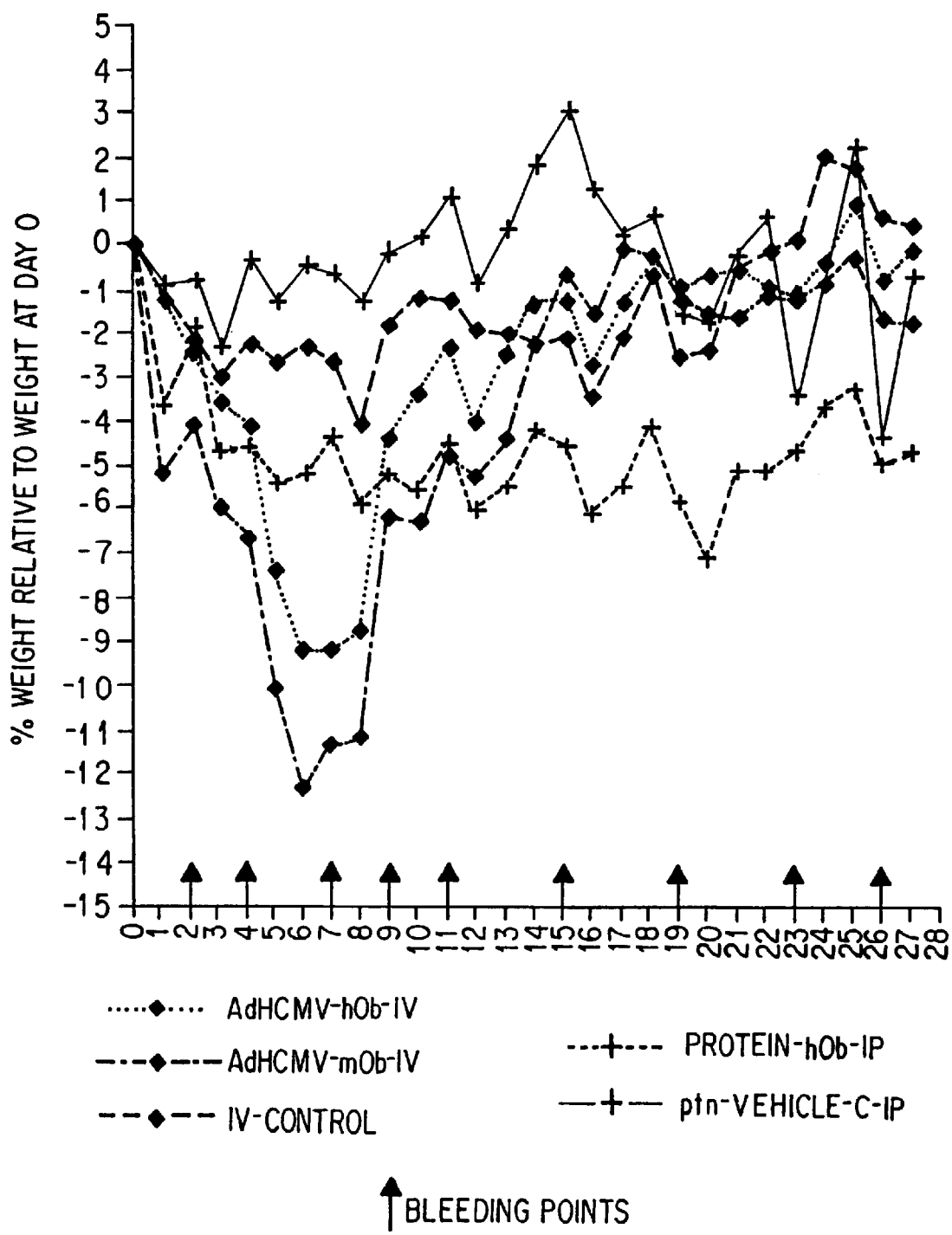
FIG. 19 shows body weight changes in treated lean mice relative to day 0 for the expanded study.

Comparisons with lean mice: Various treatments were tried on lean, "normal" mice whose genotype was (Ob/?). The changes in body weight are shown in FIG. 19. Those receiving adenovirus with the mouse leptin gene had a greater loss than those receiving the human gene, and this was a greater loss than those receiving the recombinant leptin protein IP. The control mice, those receiving IM injections and plasmid vectors showed no response.

In the lean mice receiving IP leptin treatment, a sharp drop in weight was observed during the first three days, which was substantially identical to that observed in the ob/ob mice receiving the same treatment. In the lean mice, however, it was followed by a moderation in weight reductions, and then a plateau.

In general, the gene therapy treatment response of the lean mice resembled that of the ob/ob mice in that the effect was transient. The lean mice the transient duration of treatment was shorter than that of the ob/ob mice (6 days for lean; 10–12 days for ob/ob).

Table 2 presents the percent weight change in lean mice:

TABLE 2

| Treatment | Baseline | Day 1–5 | Day 6 | Day 23 |
| --- | --- | --- | --- | --- |
| Adenovirus (IV) | 22.1 ± 1.2 | −8.76 | −10.78 | −1.19 |
| Control (IV) | 21.6 ± 2.1 | −2.71 | −2.34 | +0.14 |
| Protein (IP) | 21.7 ± 1.7 | −5.45 | −5.22 | −4.66 |
| Control (IP) | 21.6 ± 1.9 | −1.29 | −0.46 | −3.42 |

Figure 20:
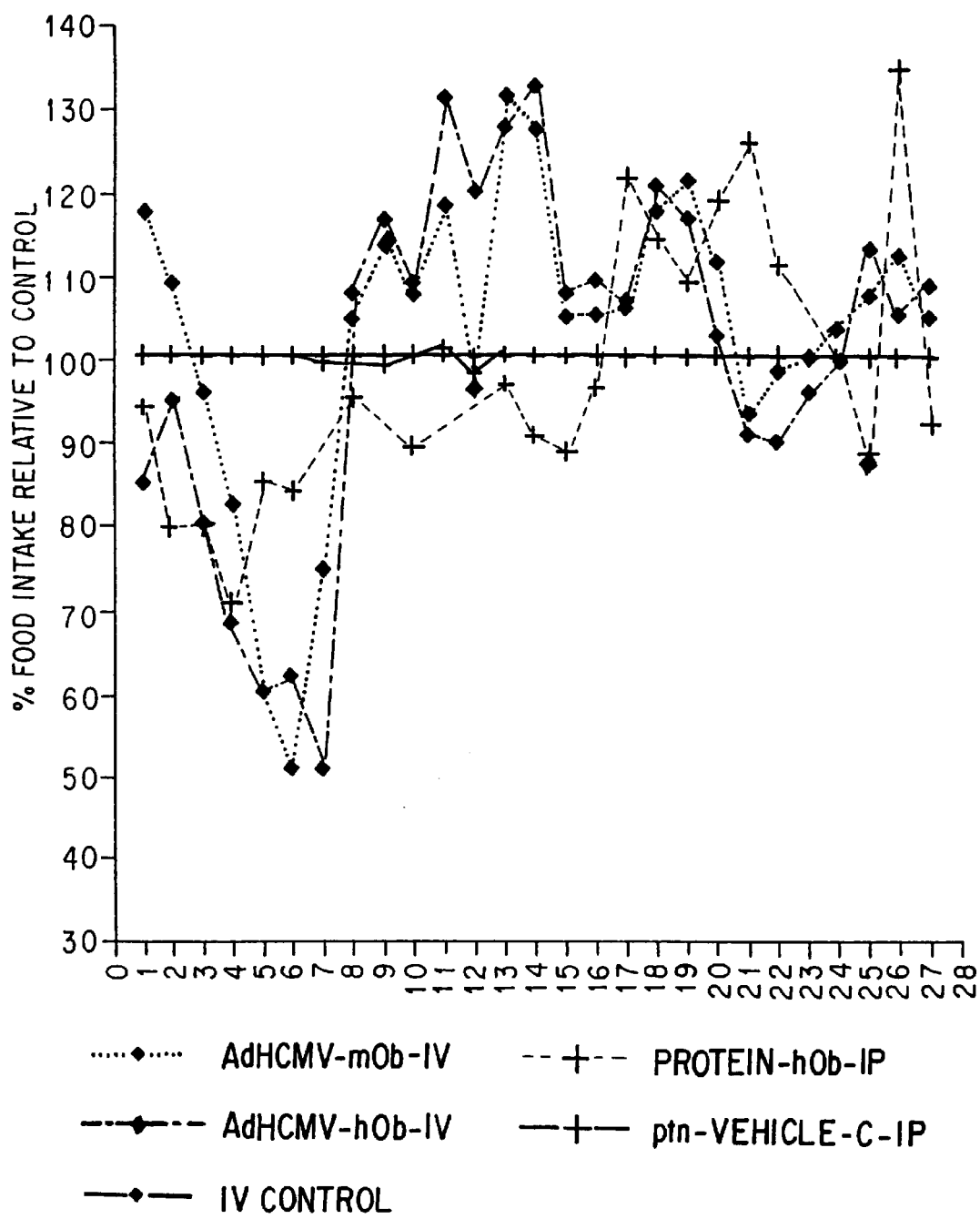
FIG. 20 shows the food intake relative to control for mice treated in the expanded study with adenovirus containing leptin or recombinant leptin.

Food intake for treated mice relative to controls was measured and is presented in FIG. 20. In adenovirus-treated mice, food intake was suppressed by about 50%. In recombinant protein treated mice, food intake was suppressed by about 30%.

Figure 21A:
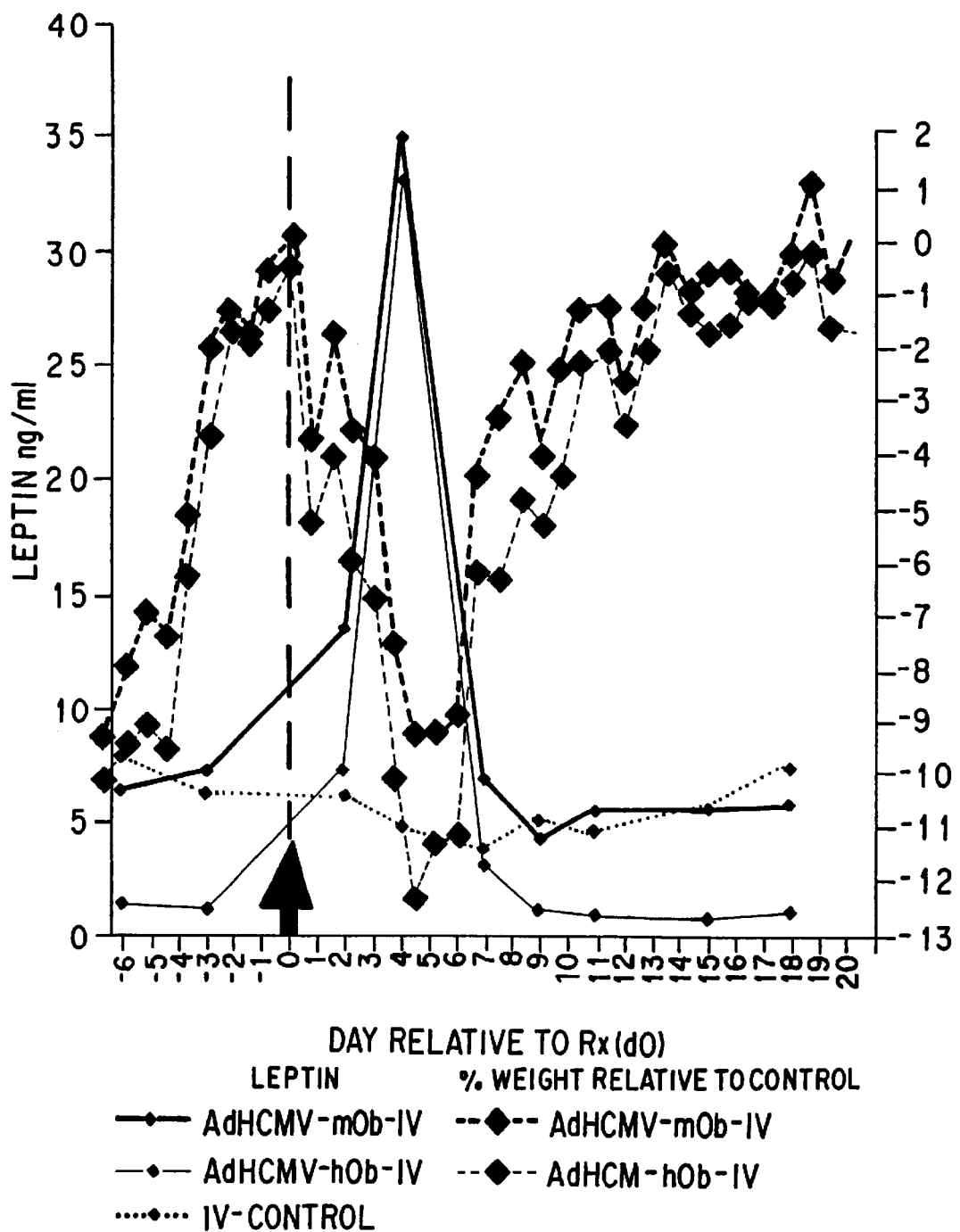
FIG. 21A shows leptin levels and weight changes of lean mice treated in the expanded study with adenovirus carrying leptin genes.
Figure 21B:
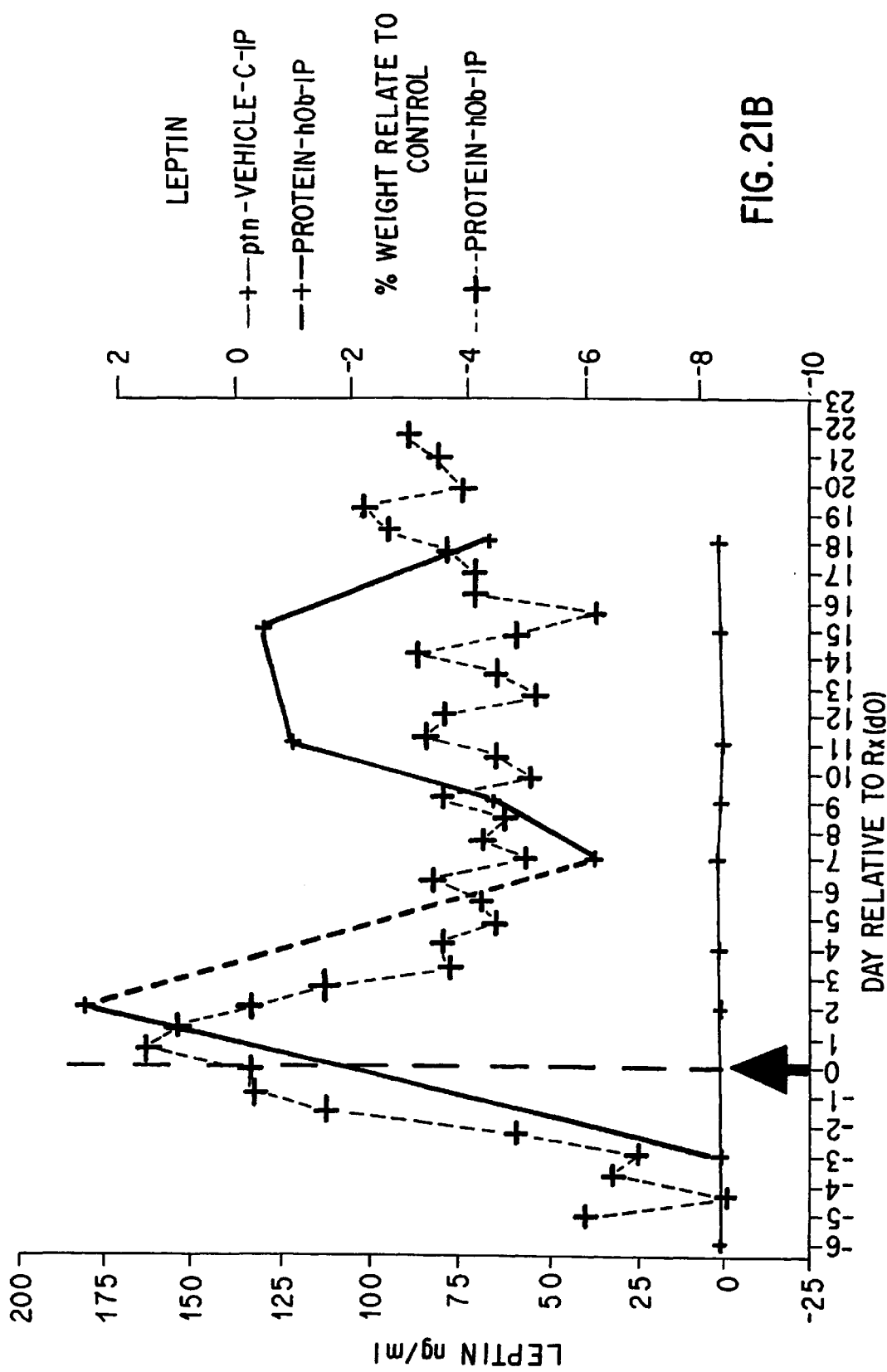
FIG. 21B shows leptin levels and weight for lean mice receiving recombinant leptin IP.
Figure 22:
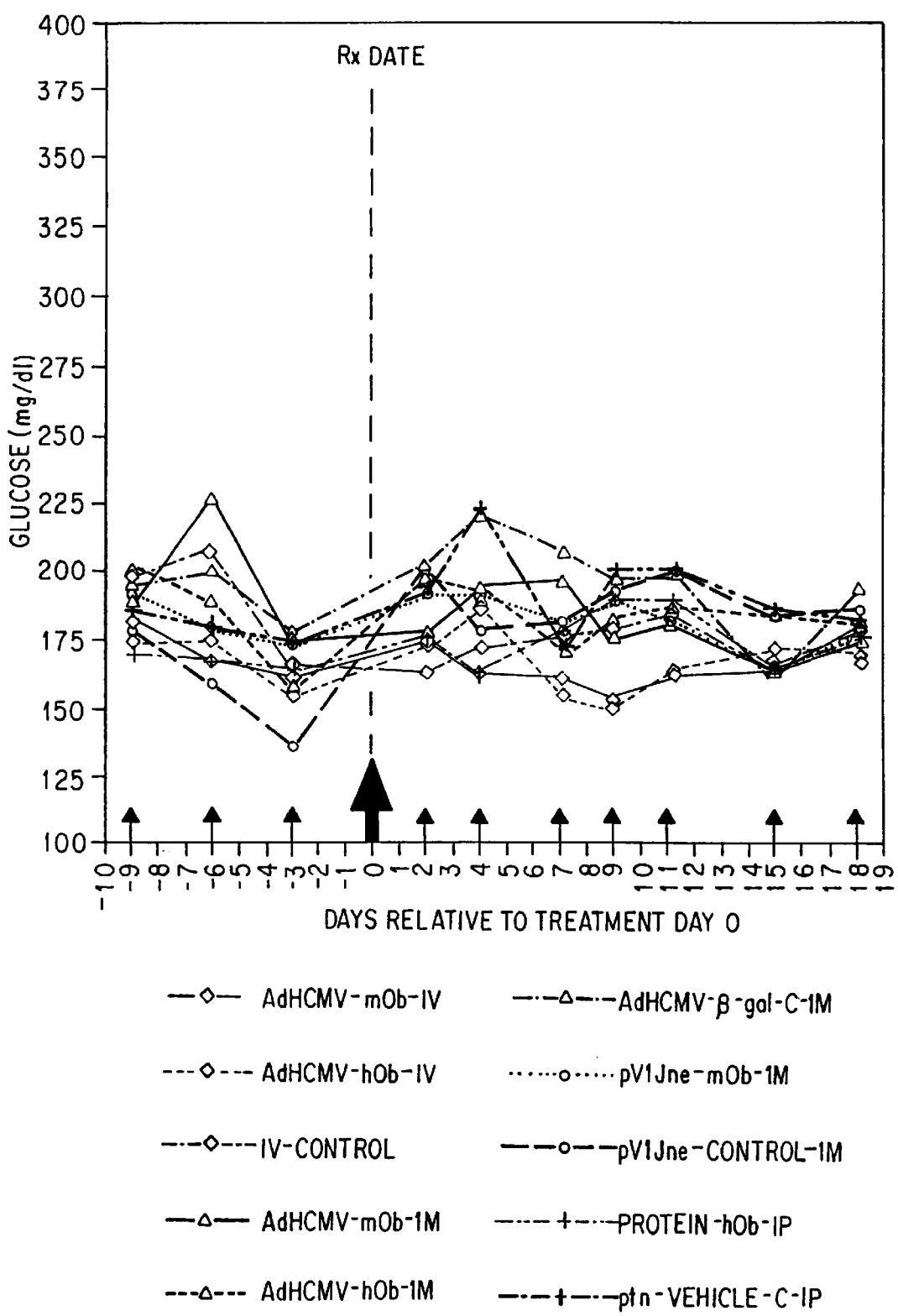
FIG. 22 shows glucose levels in lean (Ob/?) mice in the expanded study.

Leptin levels were also measured in the treated lean mice and are shown in FIGS. 21A (for mice receiving leptin gene) and 21B (for mice receiving recombinant leptin EP). Glucose levels in lean mice undergoing the treatments were measured and are shown in FIG. 22.

Figure 23A:
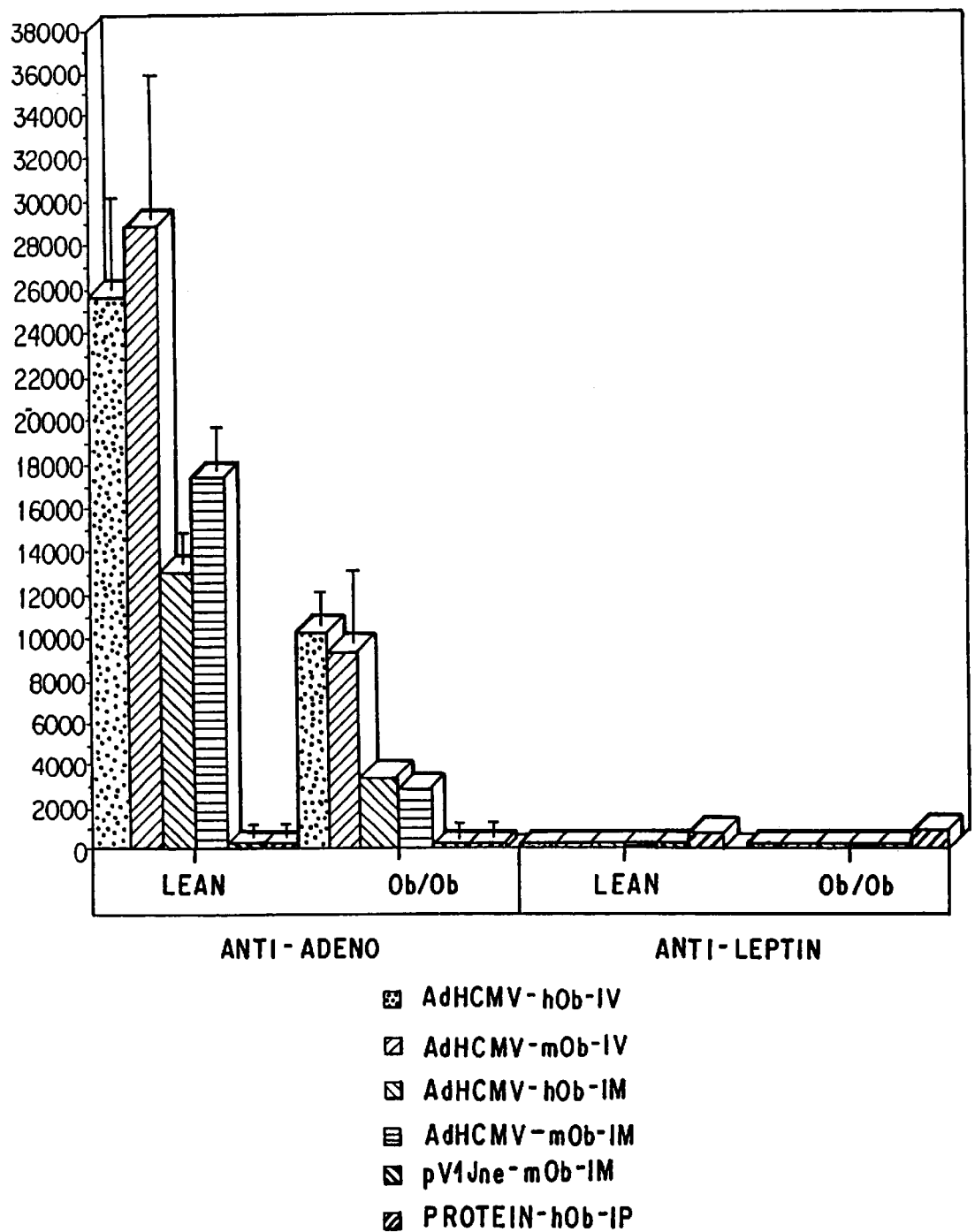
FIG. 23 shows anti-adenovirus antibody levels and anti-leptin antibody levels measured after day 15 in the expanded study.
Figure 23B:
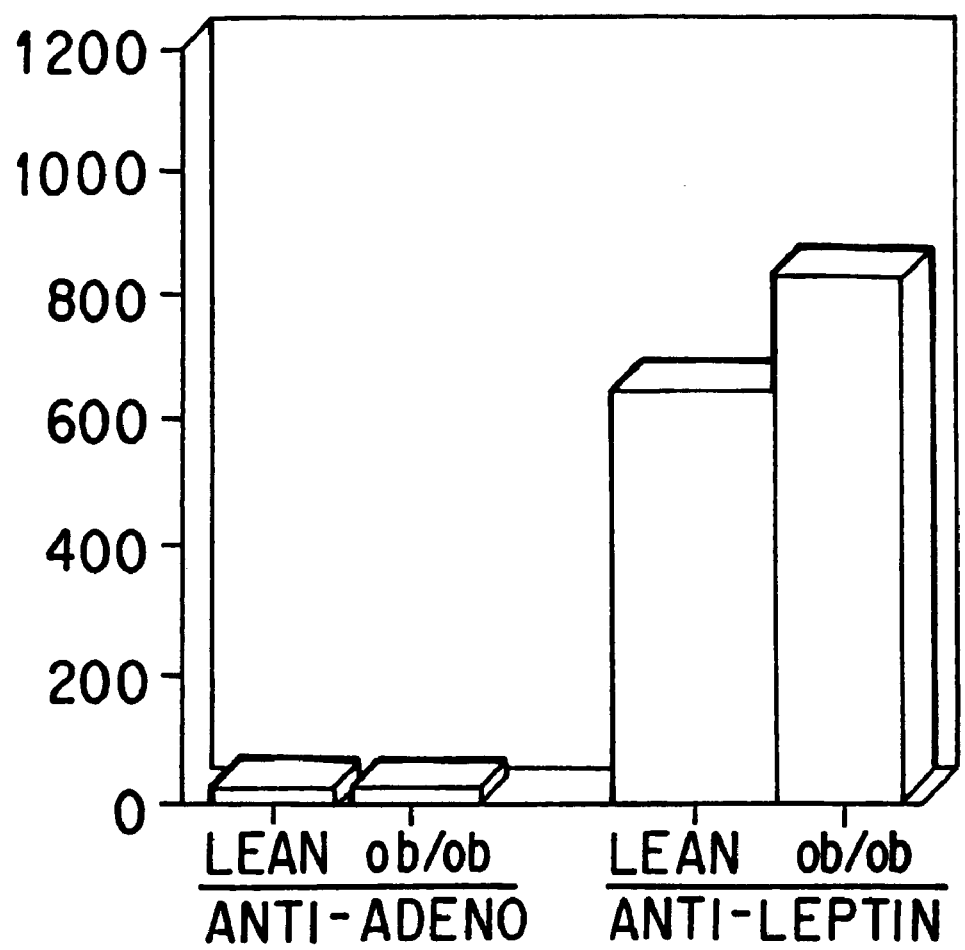
Figure 24:
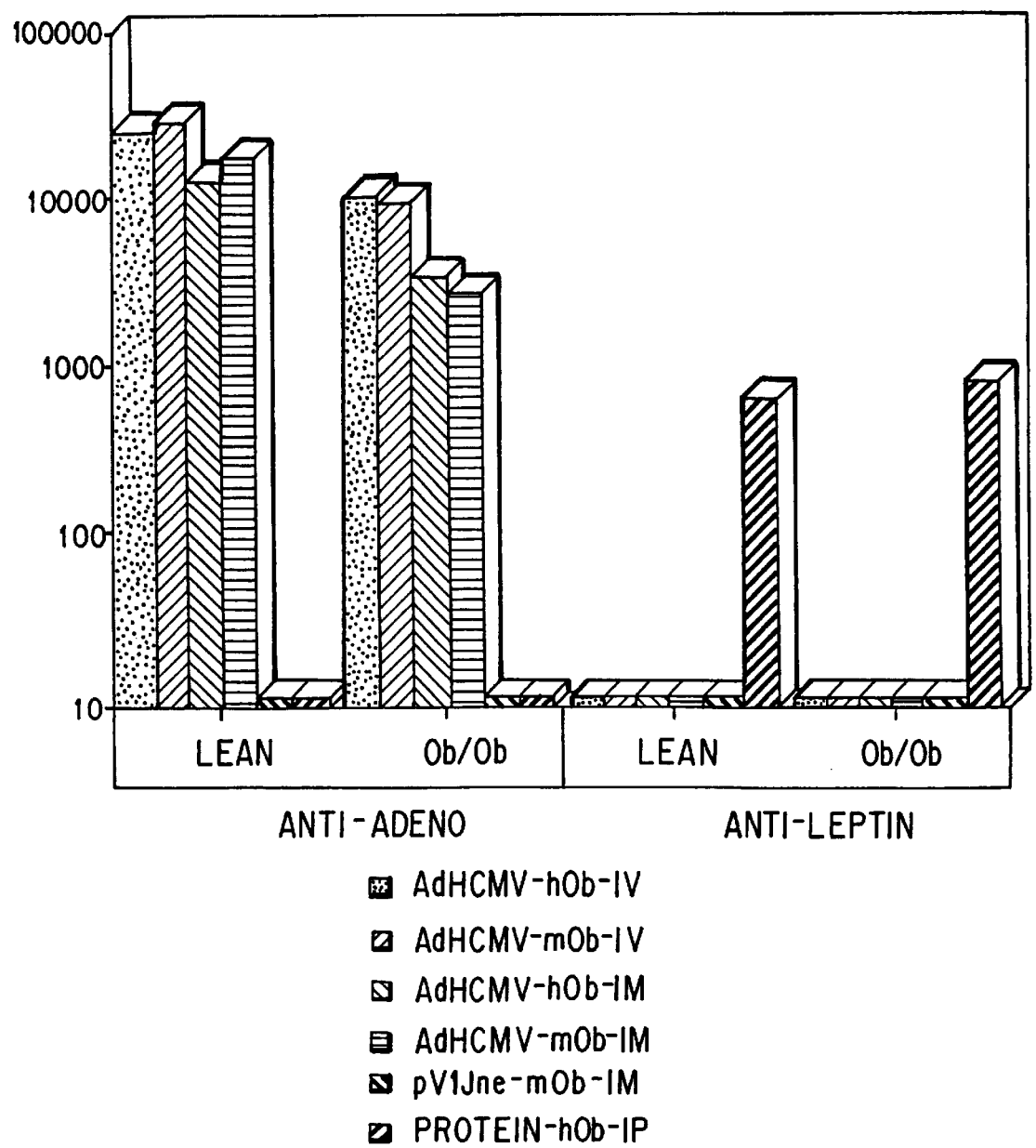
FIG. 24 shows anti-adenovirus antibody levels and anti-leptin antibody levels measured after day 15 in the expanded study.

Anti-leptin antibody levels and anti-adenovirus antibody levels were measured and are shown in FIGS. 23 and 24. Based on these responses, it is concluded that the transient expression of the leptin genes was due to an immune response to the viral proteins which were produced by the viral vector. Use of a vector which does not allow any viral proteins to be produced would result in no antibodies being produced, and a permanent, rather than transient expression of the leptin genes.

HELPER-DEPENDENT VIRAL CONSTRUCT STUDIES

In this next study (Example 6) animals received the helper dependent virus expressing mouse leptin (HD-leptin).

Mice were treated with a single tail vein administration of $1-2 \times 10^{11}$ particles of either HD-leptin, adenovirus carrying the leptin gene (Ad-leptin) or control virus.

Figure 26A:
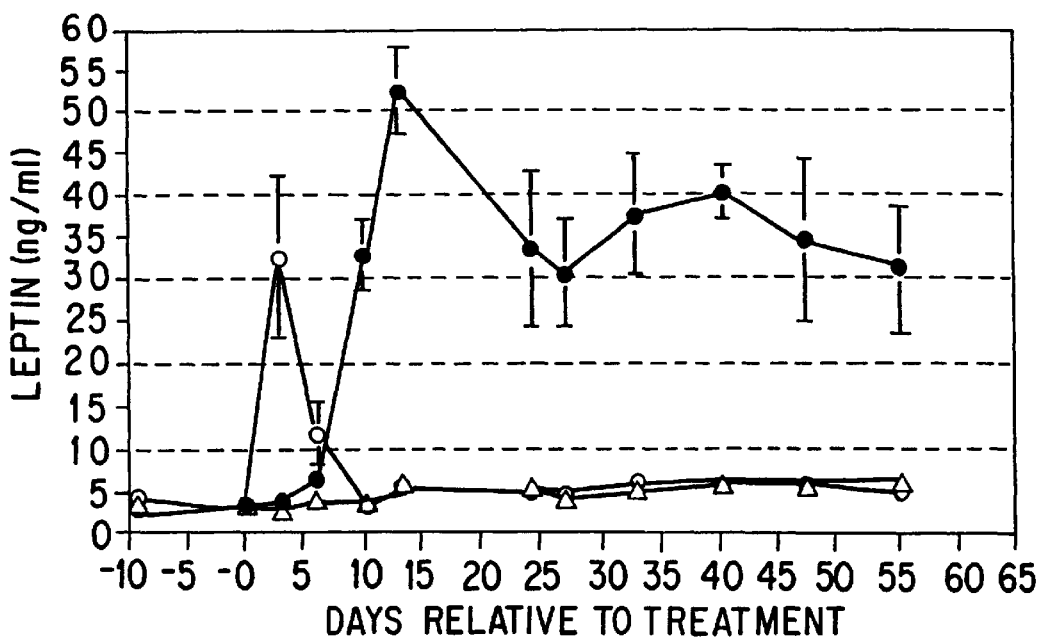
FIG. 26A shows serum leptin levels collected 2–3 times weekly (mean ±SEM).
Figure 26B:
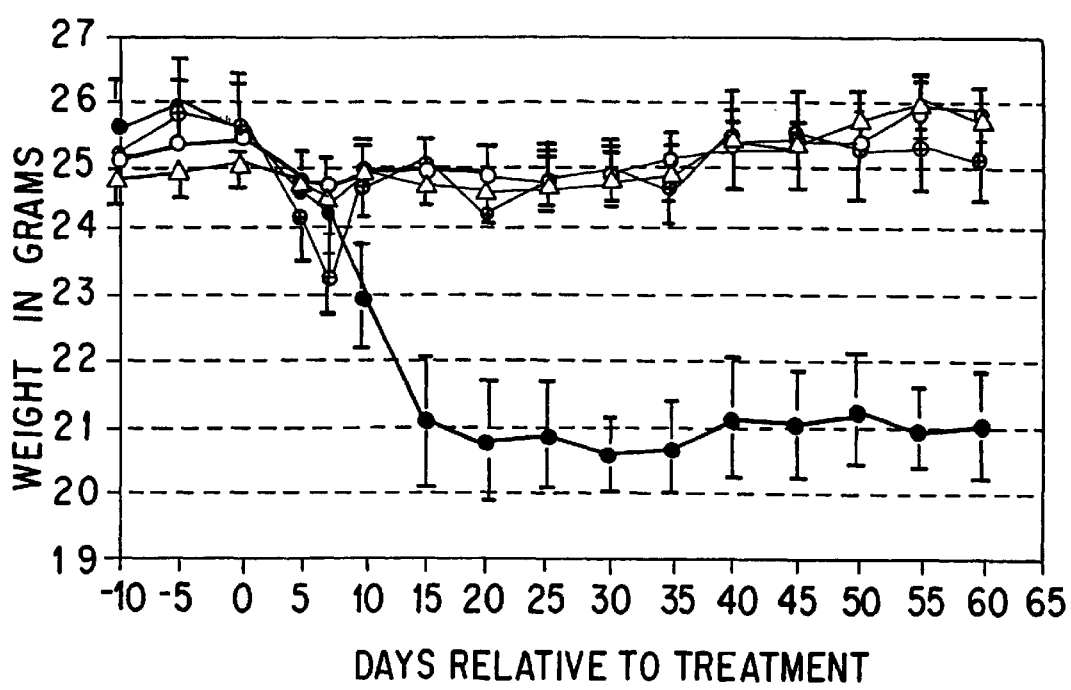
FIG. 26B shows weight (mean±SEM) measured daily.
Figure 26C:
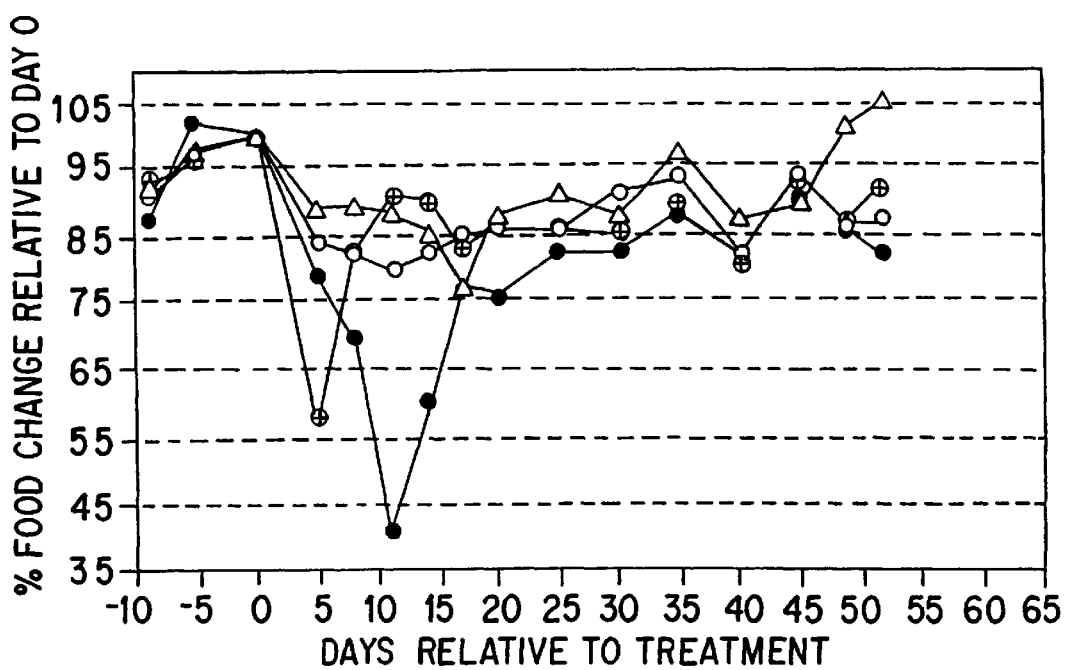
FIG. 26C shows food intake measured daily.
Figure 26E:
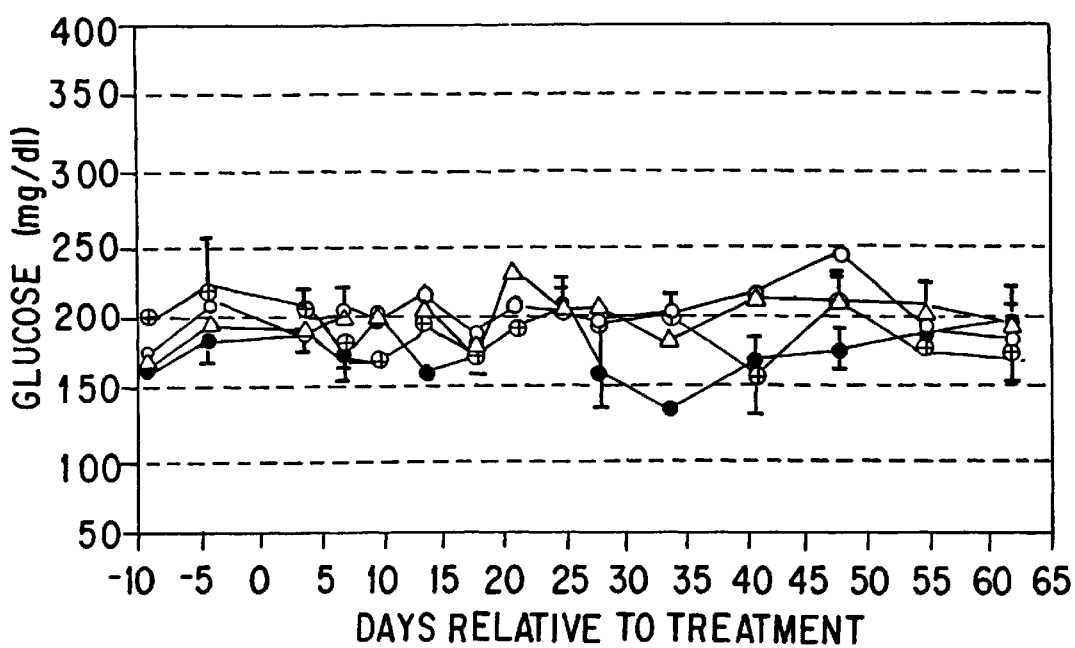
FIG. 26E is serum glucose measured in all animal groups (mean±SEM).
Figure 26D:
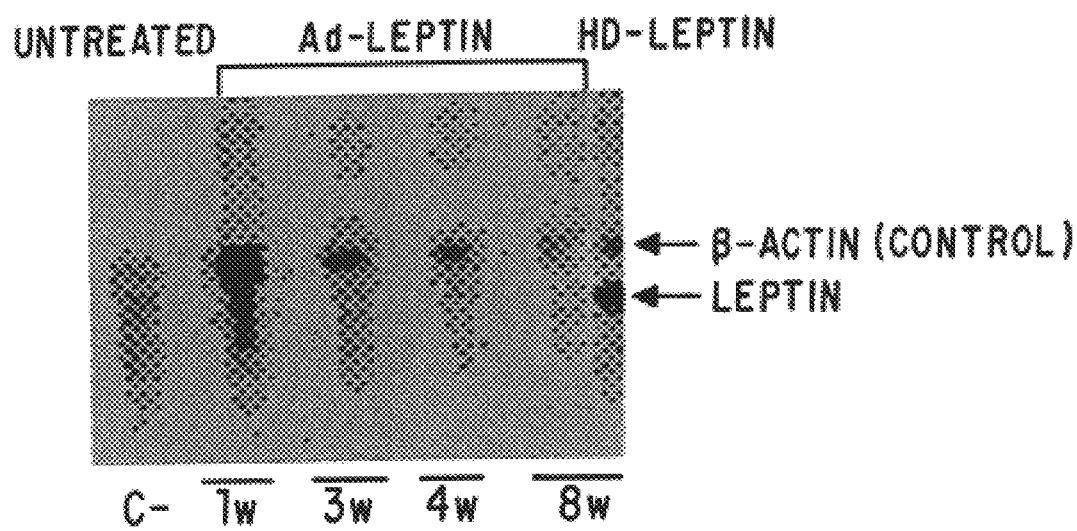
FIG. 26D is a Northern Blot of RNA extracted from liver of Ad-leptin at 2, 4, and 8 weeks.
Figure 26F:
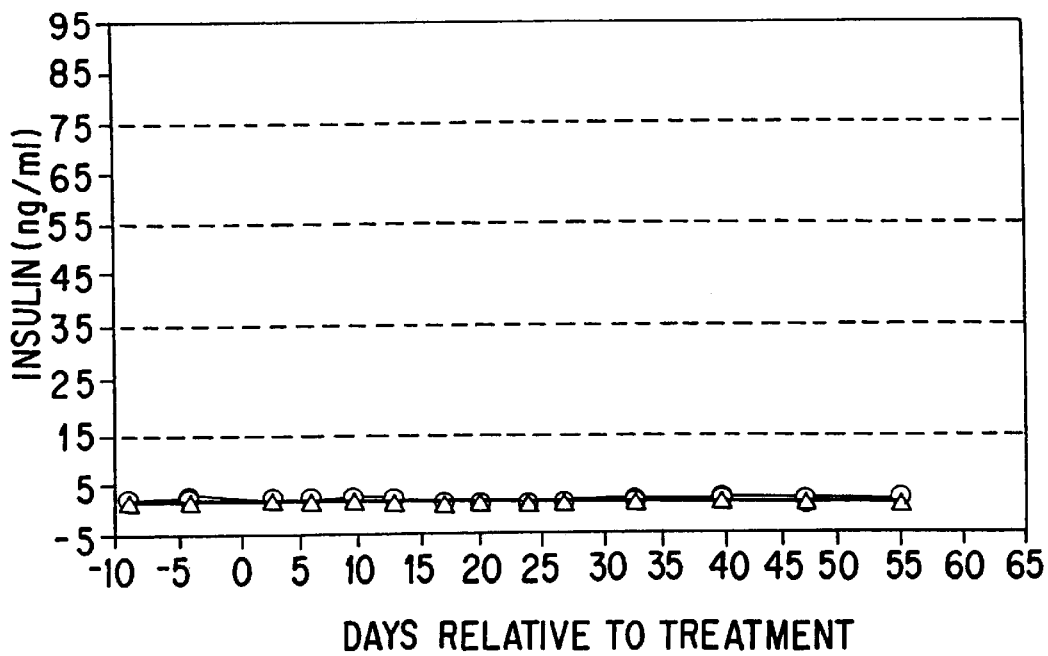
FIG. 26F is insulin levels measured in all animal groups (mean ±SEM).

In the lean mice, treatment with Ad-leptin resulted in a transient increase in serum leptin levels and weight loss for only 7–10 days (FIGS. 26A and 26B). In contrast, treatment with HD-leptin resulted in persistent high serum leptin levels (6–10 fold over background) and approximately a 20% weight loss for at least 2 months. Weight loss in HD-leptin treated mice was associated with satiety that persisted over a longer period (2–3 weeks) as opposed to those treated with Ad-leptin (5–7 days) (FIG. 26C). These effects can be correlated with the duration of gene expression obtained with these two vector types. Gene expression mediated by. Ad-leptin was found to be very transient by northern blot analysis of total liver RNA, whereas that mediated by HD-leptin persisted for at least 8 weeks (FIG. 26D). No changes in serum glucose or insulin levels were detected through out the study in the treated lean mice (FIGS. 26E and 26F).

Figure 27A:
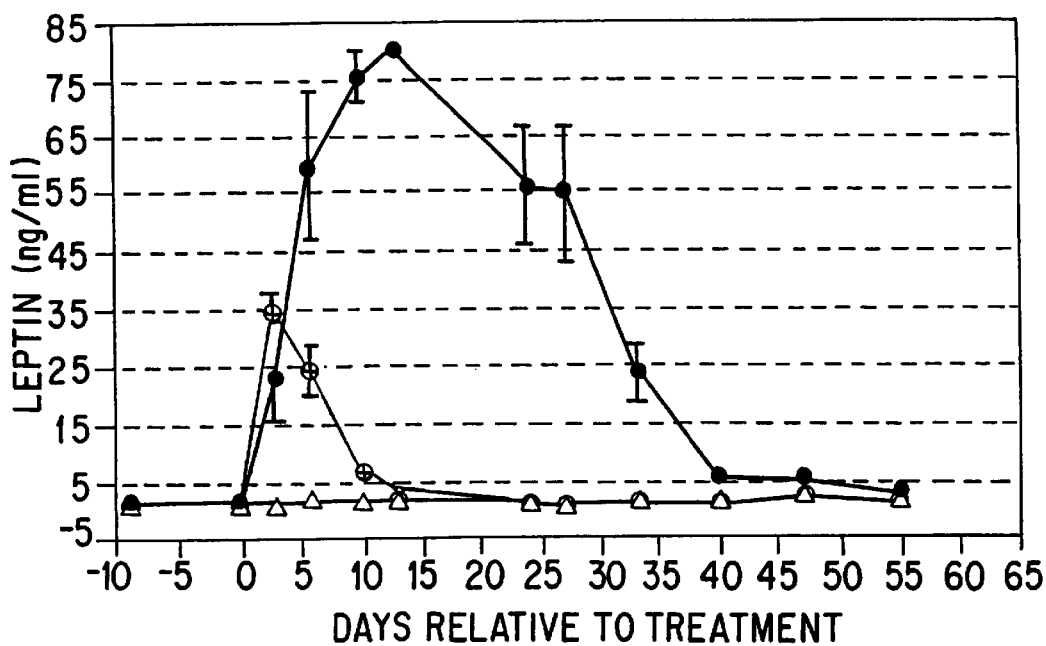
FIG. 27A shows serum leptin levels collected 2–3 times weekly (mean±SEM).
Figure 27B:
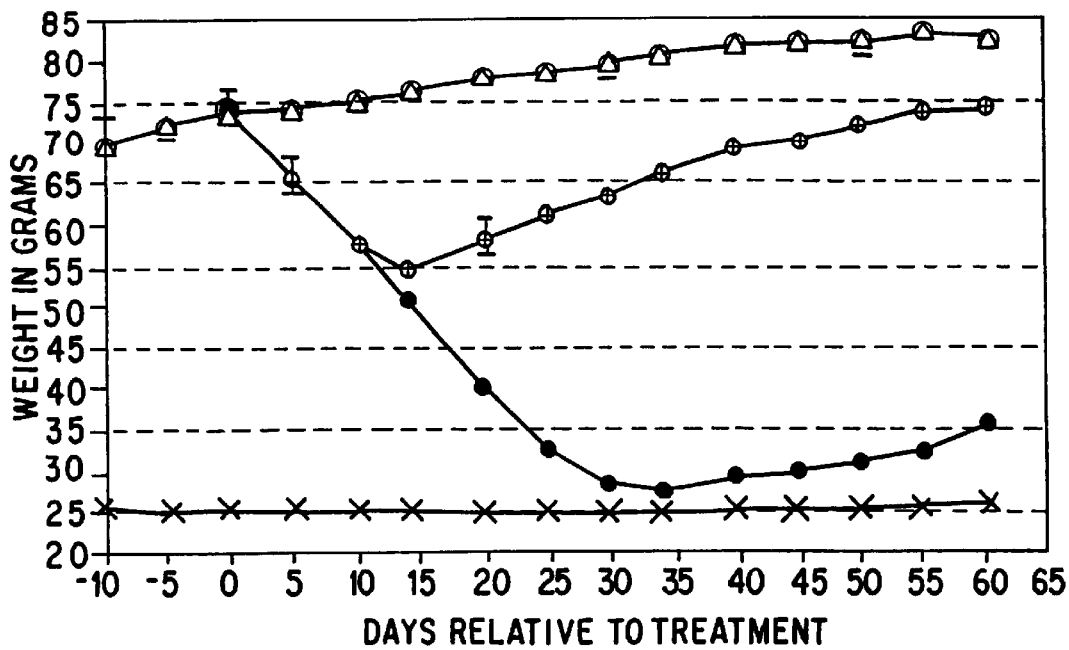
FIG. 27B shows weight (mean±SEM) measured daily.
Figure 27C:
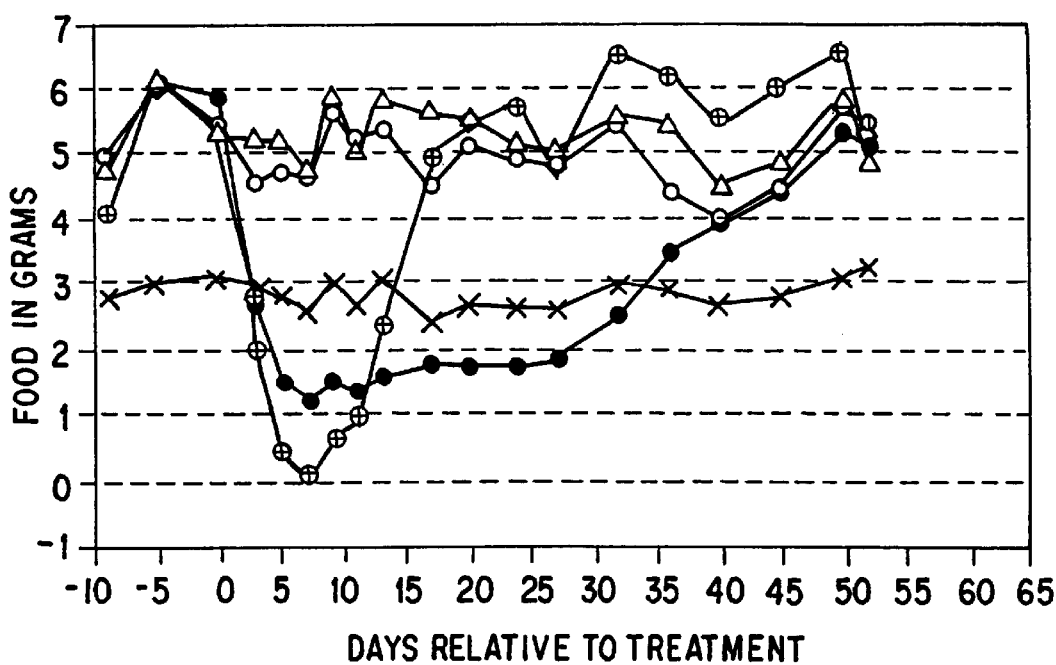
FIG. 27C shows food intake measured daily.
Figure 27D:
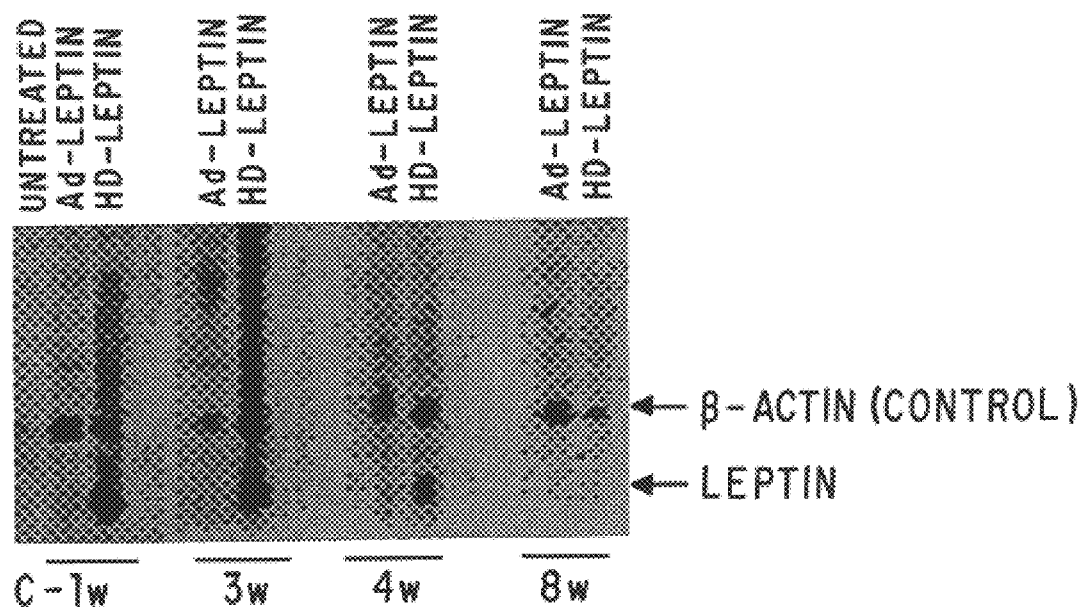
FIG. 27D is a Northern Blot of RNA extracted from liver of Ad-leptin and HD-leptin at 1, 2, 4, and 8 weeks.

The HD-leptin was also found to be more effective in obese (ob/ob) mice than the Ad-leptin vector used in the previous-described pilot and extended studies. In the oblob mice treated with Ad-leptin, serum levels of leptin increased only transiently during the first 1–4 days of treatment after which the levels declined and returned to baseline within 10 days post injection (FIG. 27A). These increased leptin levels resulted in transient body weight loss of only approximately 25% and mice began gaining weight within 2 weeks of treatment (FIG. 27B). In contrast, in the oblob HD-leptin treated mice, increasing serum leptin levels were observed up to approximately 15 days post-treatment, after which the levels gradually dropped to baseline over the subsequent 25 days. The initial rise in leptin levels correlated with rapid weight reduction resulting in greater than 60% weight loss (reaching normal lean weight) within one month. Weight loss was maintained for a period of 6–7 weeks post treatment. As leptin levels dropped to baseline a gradual increase in body weight was observed. Satiety was observed in association with increased leptin levels, and parallel to other findings food suppression was sustained for a longer period (approximately 1 month) compared to the short transient effect induced by Ad-leptin (approximately 10 days) (FIG. 27C).

Leptin specific antibodies were detected in sera of Ad-leptin and HD-leptin oblob treated mice, and it was essential to determine whether the drop observed in serum leptin levels was due to interference of the antibodies with the ELISA assay utilized to measure leptin or if the drop was due to loss of gene expression. Leptin gene expression was examined by total RNA northern blot analysis, in Ad-leptin ob/ob treated mice expression was transient and RNA levels were beyond the sensitivity level of detection at 1 week post treatment, where as in HD-leptin treated mice gene expression was detected up to 4 weeks post- injection but was undetectable at 8 weeks (FIG. 27C).

Figure 27E:
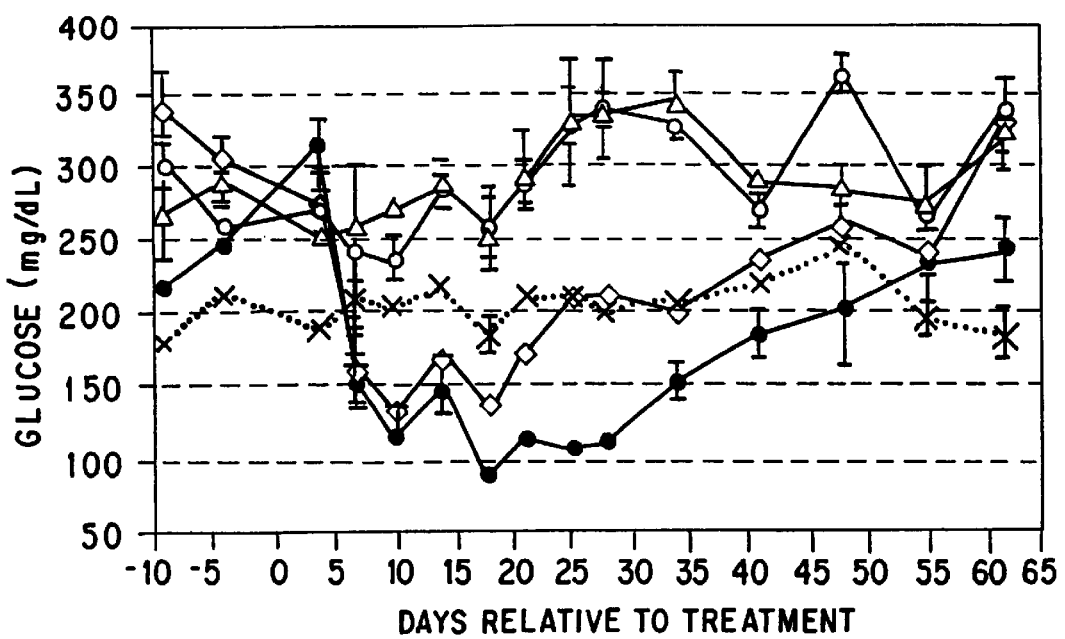
FIG. 27E is serum glucose measured in all animal groups (mean±SEM).
Figure 27F:
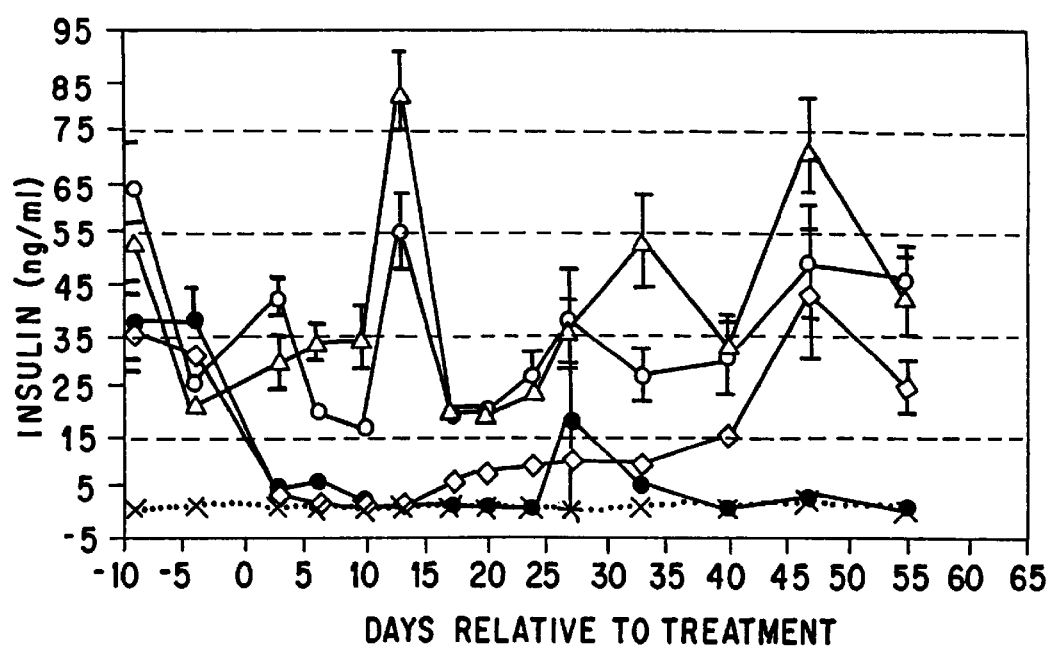
FIG. 27F is insulin levels measured in all animal groups (mean±SEM).
Figure 28:
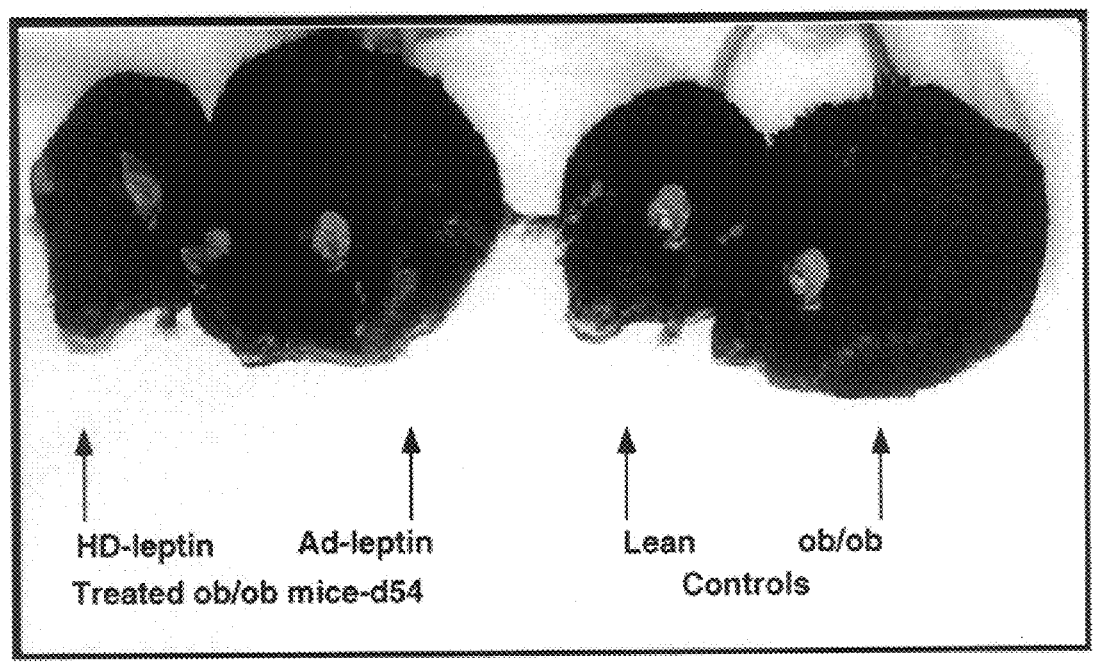
FIG. 28 shows phenotypic correction of HD-leptin treated ob/ob mice. From left to right, representative ob/ob mouse treated with HD-leptin at day 54 post treatment next to a littermate treated with Ad-leptin 54 days post treatment. Lean control mouse and untreated ob/ob mouse are provided for comparison.

Serum glucose and insulin levels dropped during the first 1–2 weeks post-treatment to normal lean values in both HD-leptin and Ad-leptin treated mice, and similar to all other findings effects of HD-leptin treatment were sustained for longer periods (FIGS. 27E and 27F. The subsequent increase in glucose and insulin levels in both vector treatments correlated with the drop observed in serum leptin levels. The overall HD-leptin mediated prolonged effect was also reflected in the accompanying phenotypic correction which was sustained for a duration that exceeded what was observed in litter mates treated with Ad-leptin (6–7 versus 2–3 weeks).

Preliminary analysis of liver histopathology in HD-leptin and Ad-leptin treated mice revealed differences in the extent and duration of cellular infiltrate. Moderate lymphoid inflammation was present in mice one week after injection with HD-leptin in contrast to moderate, acute inflammation characterized mainly by the presence of neutrophils in the Ad-leptin treated mice. At two weeks, hepatic inflammation in HD-leptin treated mice was essentially indistinguishable from controls; whereas, in the Ad-leptin treated mice the immune response was not resolved and moderate lymphoid inflammation was seen. The initial inflammatory response in the HD-leptin treated mice may be a consequence of the contaminating (<1:100 ) AdLC8cluc helper virus used in the production of HD-leptin vector. The resolution of the initial inflammation observed in the HD-leptin treated mice was associated with an initial drop in leptin levels followed by a stable persistent level of expressed leptin in lean mice and a prolonged period of continued gene expression in the ob/ob treated mice. In this study all adeno-related treatments (HD-leptin, Ad-leptin and Ad-β-gal) were associated with the generation of neutralizing antibodies, and secondary intravenous administrations were ineffective.

This study clearly illustrates that HD vectors achieved longer gene expression than what was observed by the first generation Ad-vector. The differences observed between the effects of HD-leptin and Ad-leptin on treated mice is directly related to the elimination of the Ad protein coding DNA sequences since the expression cassette containing the promoter (HCMV) and transgene (leptin) used in both vectors was identical. It has been shown that transgene immunogenicity plays a central role in loss of gene expression, which may explain the transient effect of HD-leptin seen in the ob/ob and not in the lean mice.

The leptin model used in these studies provided an excellent tool and was invaluable with regards to the specificity and sensitivity of the numerous parameters used to indirectly and directly follow relative changes in gene expression. While not wishing to be bound by theory, the differences between the longevity of expression mediated by the HD deleted vector and the transient effect observed by others, may reflect differences in the size of the recombinant virus used as it pertains to its stability and efficient packaging which have been characterized. Further, stuffer DNA may play a role in improving stability of gene expression. The HD-vector system of this invention thus reflects a significant advance over previous Ad vectors with regards to vector capacity and reduced immunogenicity in relation to viral protein expression, they have and thus wide application in gene therapy.

Thus another aspect of this invention is a method of permanently expressing a transgenic peptide or protein hormone gene in vivo by administering the gene to a mammal using a helper dependent adenoviral vector, wherein the mammal also endogenously expresses a non-transgenic version of the peptide or protein hormone gene. While not wishing to be bound by theory, it appears that the results for the ob/ob mice and the wild-type mice can be explained as follows. In the ob/ob mice, antibodies against leptin were observed, whereas in wild-type, no anti-leptin antibodies were formed. Thus in animals whose immunological system has experience with leptin, the transgenic leptin and endogenously produced leptin were immunologically indistinguishable. However in animals which do not endogenously produce leptin, the immunological system treats transgenic leptin as if it were a foreign protein, and mounts an antibody attack.

These findings, however have positive implications for the use of leptin (or other hormones) in gene therapy for humans. Human obesity is generally not the result of a double recessive mutation in which no leptin is produced. However in some obese patients, the amount of leptin produced is abnormally low. For these patients gene therapy with a helper dependent adenovirus carrying a leptin gene would provide a way of permanently correcting the leptin level.

Likewise then, the helper-dependent adenovirus system can be use to permanently deliver other protein or peptide hormone genes to a human patient, provided that patient endogenously expresses that hormone (even at a low level). This gene therapy can be used to raise protein or peptide hormone levels from below normal to a normal range. Examples include: insulin, calcitonin, erythropoietin, growth hormone, interferons, interleukin 2, hemophilia factors, VEGF, GMCSF, and alpha 1 anti-trypsin.

The following non-limiting Examples are presented to better illustrate the invention.

EXAMPLE 1

Cloning and Expression of Leptin

Two PCR cDNA amplification fragments were obtained from Jefferson University (generated by cloning both variants from a Clontech phage human hypothalamic library): one coding for the human leptin and one for the human leptin variant with glutamine, (Zhang et al., 1994, Nature 372:425; Considine et al., 1995 J. Clin. Invest. 95:2986). Both PCR fragments were amplified for cloning purposes. Two primers were designed and ordered from GIBCO BRL Custom Primers: Forward primer: ATG CAT TGG GGA ACC CTG TG (SEQ.ID.NO: 1)

Reverse primer: TCA GCA CCC AGG GCT GAG GT (SEQ.ID.NO:2)

The primers were used to re-amplify the cDNA as follows: 2 µl each primer (0.3 µ/µl stock), 2 µl dNTP (10 µM, Pharmacia), 10 µl 10 X PCR Buffer (Buffer 2 from Expand Long Template PCR System Kit, Boehringer Mannheim), 2 µl Taq polymerase (Perkin Elmer), 3 µl template DNA and 18 µl water. PCR cycling conditions were as follows: Mixture was incubated at 94° C. initially (without the addition of the Taq enzyme) for 1–2 minute, Taq was then added to each tube and the cycling program was initiated, 20 cycles of 94° C. for 30 seconds, 45° C. for 45 seconds and 72° C. for 1 minute. At the end of the 20 rounds of amplification the samples were incubated at 72° C. for 7 minutes. The expected fragment size in each case (human leptin—hOb, and human leptin with glutamine-hObGLN) was 501 and 504, respectively. The PCR amplified fragments were cloned into pCR-Script. SK(+) plasmid (Stratagene) and several selected bacterial colonies were grown, plasmids extracted and sequenced to verify correct sequence of both cloned.

Inserts were then used for generating recombinant adenoviral shuttle vectors. The adenoviral vectors used in this study are essentially the same as those described in Morsey et al., 1993 J. Clin. Invest. 92: 1580–86, which is hereby incorporated by reference, except for the leptin gene insert. The pdefElsplCMV-BGHpA adenoviral shuttle vector, obtained from Baylor College of Medicine was used for the cloning of the two inserts (hOb and hObGLN) Similarly mOb cDNA (Zhang et al., 1994 Nature 372:425) was inserted into 5 pdelElsplCMV-BGHpA. All three shuttles (pdelElsplCMV-mOb-BGHpA, pdelE I sp1 CMV-hOb-BGHpA and pdelE I sp ICMV-hObGLN-BGHpA) were tested for leptin expression by western blot analysis.

EXAMPLE 2

The three shuttle vectors from the previous example are used in rescue replication of the deficient El deleted adenoviral vectors. 293 cells, commercially available from Microbix, passage 27–30 were set up one day ahead of transfection in 60 mm dishes, and were about 70–80% confluent at the time of use.

Plates were made containing one of the shuttle plasmids and pJMI7; pFG140 (purchased from Microbix Biosystems Inc.) was used as a positive control for the efficiency of transfection. Plaques were identified, and plugged out of the agarose overlay using a sterile glass Pasteur pipette. Each plugged plaque was resuspended in 100–500 µl of PBS (with calcium and magnesium) in 10% glycerol, frozen at –80° C. and thawed (1–3 times). The thawed plaque was then used to infect a 90% confluent 6 cm plate of 293 cells to expand the isolated virus. 5–8 days post infection, cytopathic effects (CPE) were apparent on the cells (cells rounded up and started to detach and float in media). Cells were collected by scraping and tested for leptin expression by western analysis and for DNA restriction pattern by Hind mH digestion of extracted DNA and ethiduim bromide stained gel analysis. One of the positive plaques identified based on leptin secretion and correct DNA restriction pattern was selected and used for a second plaque purification followed by a similar procedure of expansion and analysis. After the second plaque purification, the virus was propagated on a large scale. Cesium banding and titration was used to purify and quantitate.

The resulting titered viral stocks (Ad-HCMV-mOb-BGH$^{PA}$, Ad-HCMV-hOb-BGH$^{PA}$ and Ad-HCMV-hOb GLN-BGH$^{PA}$) were stored at –80° C. until use.

EXAMPLE 3

Pilot Study

Baseline determinations

Three groups of 8 week old mice were used: ob/ob, db/db, and lean (wild type, controls). All groups of mice were fed milled Purina Chow 5008 starting from day of arrival or day after arrival. Food consumption was also measured. After approximately 4 days on milled chow, the mice were weighed and bled for determination of plasma levels of glucose and insulin. Injections were started 8 days after the initiation of base line measurements but before injections, mice were weighed and blood samples were obtained from all study mice for determination of plasma glucose and insulin. Leptin level in plasma were also measured.

Mice were housed 5 per cage and fed milled Purina Chow 5008 in feed cups with lids. 24 hour food consumption was measured at the same time each day. Only after food consumption was equilibrated to a fairly constant level, usually 20–25 grams chow/5 mice-day, was virus injected.

On the day of injection but before injection, food consumption, body weight, and a baseline blood sample were taken in the morning from a snipped end of tail. Blood was collected into heparinized capillary tube (total volume approximately 70–100 µl). Hematocrit was measured, and plasma was collected.

Mice were injected as follows: A. ob/ob mouse groups: iv injections. 5 mice/group Group 1 received 2.75×10$^8$ / gm wt of AdHCMV-hob-BGH$^{PA}$ (in 500 µl dialysis buffer) in the tail vein. Group 2 received 2.75×10$^8$ gm wt of AdHCMV-Ogal reporter (in 500 µl dialysis buffer) in tail vein. Group 3 received 500 ml dialysis buffer in tail vein. Group 4 received 1 mg/kg wt active leptin daily IP injections for 5 days. B. db/db mouse groups: iv injections. 5 mice/group Group 1 received 2.75×10$^8$ gm wt of AdHCMV-hob-BGH$^{PA}$ (in 500 µl dialysis buffer) in the tail vein. Group 2 received 2.75×10$^8$ gm wt of AdHCMV-Ogal reporter (in 500 µl dialysis buffer) in tail vein. Group 3 received 1 mg/kg wt active leptin daily IP injections for 5 days. C. Lean control mouse group: one cage of 5 mice as measure of lean parameters No injections.

EXAMPLE 4

Leptin Receptor

Adenovirus vectors are made similarly to those described in Examples 2–3, except that the leptin receptor gene replaces the leptin gene. Mice which are db/db are used in place of the ob/ob mice. Results for the db/db mice are similar to those observed with the ob/ob mice reported herein. After injection, glucose levels fall, insulin levels fall and the mice loose weight. No effect is observed in control mice and in ob/ob mice injected with vector carrying a leptin receptor gene.

EXAMPLE 5

Repeat and Expanded Study

Procedures followed were similar to those given in Example 3, with the following changes. Mice were older (12 weeks at the start of the experiment vs. 8 weeks) and were larger at the start of the experiment (approximately 50 grams vs. approximately 35 grams). In addition, further treatments were given, as shown below. Mice in the ob/ob group were treated as follows:

| Group Number | n = | treatment | description of treatment |
|---|---|---|---|
| #1 | 10 | AdHCMV-hob-BGH$^{pA}$ | $1.5 \times 10^9$ pfu/mouse (in 450 µl dialysis buffer in the tail vein. |
| #2 | 10 | AdHCMV-mob-BGH$^{pA}$ | same as #1 |
| #3 | 5 | dialysis buffer control | same as #1 |
| #4 | 5 | Ad control β-gal expression | same as #1 |
| #5 | 10 | hOB protein | daily (1 mg/kg initial wt in 200 µl) IP injections of active hOb for the length of the study |
| #6 | 5 | vehicle control | 200 µl protein suspension buffer |
| #7 | 10 | AdHCMV-hob-BGH$^{pA}$ | IM $1.5 \times 10^9$ pfu (distributed equally on both quadriceps muscles, 60 µl vol). |
| #8 | 10 | AdHCMV-mob-BGH$^{pA}$ | same as #7 |
| #9 | 5 | Ad control β-gal expression | same as #7 |

In addition, lean mice (genotype Obi?) were also treated in ie same way as the ob/ob mice above.

| Lean Group Number | n = | treatment | description of treatment |
|---|---|---|---|
| #1 | 10 | AdHCMV-hob-BGH$^{pA}$ | $1.5 \times 10^9$ pfu/mouse (in 450 µl dialysis buffer in the tail vein. |
| #2 | 10 | AdHCMV-mob-BGH$^{pA}$ | same as #1 |
| #3 | 5 | dialysis buffer control | same as #1 |
| #4 | 5 | Ad control β-gal expression | same as #1 |
| #5 | 10 | hOB protein | daily (1 mg/kg initial wt in 200 µl) IP injections of active hOb for the length of the study |
| #6 | 5 | vehicle control | 200 µl protein suspension buffer |
| #7 | 10 | AdHCMV-hob-BGH$^{pA}$ | IM $1.5 \times 10^9$ pfu (distributed equally on both quadriceps muscles, 60 µl vol). |
| #8 | 10 | AdHCMV-mob-BGH$^{pA}$ | same as #7 |
| #9 | 5 | Ad control β-gal expression | same as #7 |

Prior to treatment, the lean mice (Obi? genotype) had the following baseline body weight statistics:

| Treatment | n | mean | median | sd | min | max |
|---|---|---|---|---|---|---|
| AdHCMV-hOB (IV) | 8 | 22.1 | 22.5 | 1.2 | 20.3 | 23.4 |
| AdHCMV-mOb (IV) | 10 | 21.9 | 21.8 | 1.5 | 19.2 | 24.3 |
| Dialysis control (IV) | 5 | 21.9 | 22.3 | 1.2 | 19.9 | 23.2 |
| AdHCMV-β-gal-C (IM) | 5 | 21.5 | 21.3 | 2.4 | 18.2 | 23.9 |
| protein-hob (IP) | 10 | 21.7 | 21.7 | 1.7 | 19.1 | 24.2 |
| protein-vehicle C (IP) | 5 | 21.6 | 20.7 | 1.9 | 19.7 | 24.1 |

The following table compares the maximum response observed in ob/ob and lean mice from day 0 to day 23

| Treatment | ob/ob median change, (% change) | Ob/? median change, (% change) |
|---|---|---|
| AdHCMV-mOB (IV) | −14.2 (−28.4%) | −2.9 (−13.2%) |
| AdHCMV-hOB (IV) | −11.1 (−21.3%) | −2.1 (−9.4%) |
| protein hOB (IP) | −8.9 (−17.3%) | −1.5 (−6.9%) |
| Controls | −0.4 to 0.1 (−0.7% to 0.2%) | −1.4 to −0.4 (−5.5% to −2.0%) |

EXAMPLE 6

Helper-Dependent Constructs

Construction of plasmid pSTK was as follows using standard techniques, known to those of ordinary skill in the art. Bluescript KSII (Stratagene) DNA was cleaved with EcoRV. A double-stranded oligodeoxynucleotide with the restriction sites AscI-AvrII-FseI-PacI was generated by annealing the single-stranded oligodeoxynucleotides #17302 and #17303: #17320:5'-GGC GCG CCC CTA GGG0GCC GGC CTT AAT TAA -3'(SEQ.ID.NO:3) #17303: 5'-TTA ATT AAGOGCC GGC CCC TAG GGG CGC GCC-3'(SEQ.ID.NO:4) The oligodeoxynucleotide was inserted into the EcoRV side of Bluescript KSII using T4 DNA ligase (NEB). The resulting plasmid was called STK2. STK2 was cleaved with BstXI and the BstXI site was made blunt ended using T4-DNA Polymerase (Pharmacia). A double-stranded deoxyoligonucleotide with the restriction sites SwaI-PmeI-SNaBI was generated by annealing the single-stranded oligodeoxynucleotides #17300 and #17301: #17300:5'- ATT TAA ATG CCC GCC CGT TTA AAC TAC GTA -3'(SEQ.ID.NO:5). #17301: 5'- TAC GTA GTT TAA ACG GGC GGG CAT TTA AAT-3'(SEQ.ID.NO:6) The oligodeoxynucleotide was inserted into the blunt-ended BstXI site using T4-DNA ligase. The resulting plasmid was called STK3.

The left terminus of Adenovirus type 5 was amplified by PCR using oligodeoxynucleotides #23531 and #23532. #23531: 5'-AGC TTT GTT TAA ACA TCA TCA ATA ATA TAC CTT ATT TTG - 3'(SEQ.ID.NO:7), where the bolded area is a PmeI restriction site and the underlined is Adenovirus type 5 base pairs 1–26. #23531: 5'- CGA TAA GCT TGA TAT CAA AAC GCC AAC TTT GAC CC-3' (SEQ.ID.NO:8) where the bolded areas are a HindIll restriction site, the italic are an EcoRV site, and the underlined is Adenovirus type 5 base pairs 440421.

The resulting PCR product was cleaved with PmeI and Hindli. STK3 was cleaved with PmeI and Hindli and the Pme/HindIII cleaved PCR product described above was inserted into the PmeI and HindIII sites of STK3 using T4-DNA ligase. The resulting plasmid was called STK31.

The right terminus of Adenovirus type 5 was amplified by PCR using oligodeoxynucleotides #23531 supra, and #24147: #24147: 5'-CGA TAA GCT TGA TAT CAC TCC GCC CTA AAA CCT ACG -3'(SEQ.ID.NO:9), wherein the bolded area is a HindIll restriction site, the italic is an EcoRV site, an the underlined area is Adenovirus type 5 base pairs 35818–35837. The resulting PCR product was cleaved with PmeI and HindlU.

STK3 was cleaved with PmeI and HindIR and the PmeI/HindU! cleaved PCR product described above was inserted using T4-DNA ligase. The resulting plasmid was called STK3–23531/24147.

STK31 was cleaved with EcoOI09. The EcoOI09I site was made blunt-ended using the Klenow fragment of DNA Polymerase I (Pharmacia). Plasmid STK3–23531/24147 was cleaved with SnaBI and EcoRV. The resulting SnaBI-EcoRV fragment containing the right terminus of Adenovirus type 5 was inserted into the EcoOI09I site of STK3 1. The resulting plasmid was called STK42.

A cosmid containing part of the hypoxanthine guanine phosphoribosyltransferase (HPRT) gene (U72D8) was cleaved with EclXI and PmeI. EciXI cleaves at bp 1799 and PmeI at bp 17853 of the sequences which is deposited in the GenBank database (Locus: Human HPRT gene [HUMHPRTB]; gb:humhprtb). STK3 was cleaved with PmeI and EciXI. The 16054 bp EclXI/PmeI HPRT fragment from the HPRT gene containing cosmid was inserted into the PmeI and EcIXI sites of STK3. The resulting plasmid was called STK55.

STK42 was cleaved with HincII. STK55 was cleaved with PmeI and SalI. The SalI site was made blunt-ended using the Klenow fragment of DNA Polymerase I. The resulting fragment that contained the 16054 bp EcIXI/PmeI HPRT fragment was inserted into the HincII site of STK42. The resulting plasmid was called STK68.

STK68 was cleaved with AscI. AscI was made blunt ended using the Klenow fragment of DNA Polymerase I. The cosmid C346 (Andersson et al. 1995 DNA Seq. 5: 219–223, which is hereby incorporated by reference) was cleaved with HindIII and the ends were made blunt-ended using the Klenow fragment of DNA Polymerase I. HindIII cleaves at bp 12421 and 21484 of the sequence that is deposited in the GenBank database (Locus: HUMDXS455A; gb:L31948). The 9063 bp HindEil fragment of C346 was inserted into the AscI site of STY,68. The resulting plasmid was designated pSTK120.

After cloning of the leptin expression cassettes described previously into pSTKI20, 10 µg of the recombinant constructs were digested with PmeI enzyme, and 5 µg of digested DNA was transfected into 293-cre4 cells monolayer/well in a 6 well plate using Lipofectamine (GIBCO) following the manufacturers instructions. 24 hours post-transfection, the cells were infected with approximately $5 \times 10^5$ plaque forming units (pfu) of helper virus AdLC8clucl. Cells were collected after cytopathic effect (CPE) was observed, which took approximately A3–5 days. Lysate was used to infect 6 cm plates of 293-cre4 monolayers& Plates were infected with 1 ml lysate and 1 ml media (MEM-α supplemented with 10% serum 1 X pen/strep, 1 X L-glutamine and sodium bicarbonate), followed 24 hours later with 0.1–1 X 106 pfu of the helper virus. After CPE (approximately 4–5 days), lysate was collected and used to infect 10 cm plates of 293-cre4 cells, the same process was followed, infection in 10 cm plates used 2 ml lysate, 8 ml media and 1–5×106 helper virus (added 24 hours post lysate infection). CPE collection was followed and lysate was used to infect 15 cm plates of 293-cre4 cells (approximately 1×107 cells). 5 ml cells plus 15 ml media was used with 0.1–1 ×107 pfu helper was added 24 hours post-lysate collection. After CPE collected lysate was used to infect twenty 15 cm plates of 293 cre4 cells, this step (passage 5) is the first passage used for cesium banding and virus purification.

Cesium banding and virus purification was identical to the. process used to purify the first generation virus. Supernatant from passage 5 was also used to further propagate the virus. Occasionally two cesium bands were observed, the lower band was the helper dependent virus. Virus was dialyzed and as was the case with the first generation, titered on regular 293 cells to determine the level of contaminating helper viruses which are capable of plaque formation.

Figure 25B:
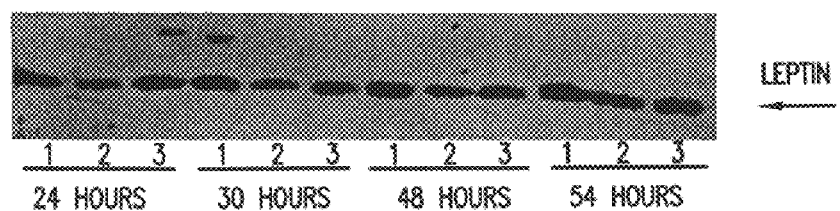
FIG. 25B illustrates detection of leptin protein expression mediated by the HD-leptin virus in vitro using a Western blot with polyclonal antibodies. Details are provided in Example 6.

The helper dependent virus is not capable of forming plaques; therefore to estimate levels of rescued virus, optical density (OD) readings were made. It is estimated that the infective particles are approximately 10 to 100-fold lower that the estimated particle number measured by optical density. Also, comparisons between the viral vectors described in Examples 1–5 and the helper dependent leptin gene expression were used to estimate particle number. Yield was approximately $8 \times 10^{12}$ particles ($2 \times 10^{12}$/ml). For semi-quantitation of infectious particles, COS cells were infected with 10 µl of HD-leptin or with Ad-leptin at a moi of 10 or 15. Cells were washed 30 minutes post-infection and serum-free media was added. 100 R1 aliquots of media were collected from infected plates at 24, 30, 48 and 54 hours post-treatment, and compared by western blot analysis for leptin protein levels, using a polyclonal anti-leptin antibody (Santa Cruz Biotech) (See FIG. 25B). Leptin was detected as a single band at approximately 16 kD. The HD-leptin mediated expression was equivalent to the 15 moi infected plates, and based on the pfu titer of Ad-leptin, the estimated titer was approximately $1–2 \times 10^{10}$ ImI with a particle to infectious unit ratio of approximately 1:100.

EXAMPLE 7

Ob/ob (C57BL/J6-ob/ob) and litter mates, homozygous normal lean mice, age and sex matched (females) were purchased from Jackson Laboratories (Bar Harbor, Me.) for the use in this study. Animals were free of all common murine pathogens. Eight to twelve weeks old mice (oblob approximately 70 gm and lean approximately 28 gm) were re-distributed based on equal representation of weight and caged in groups of 5 on day 0, immediately preceding treatment. After 30 a series of baseline blood samples were obtained by tail incision from conscious mice, animals were divided into 4 groups and treated by tail vein injection of a single 100 µl aliquot of $1–2 \times 10^{11}$ particles of HD-leptin, Ad-leptin, Ad-(3gal (control) or dialysis buffer (control).

Body weight and food intake were measured daily and blood was collected 2–3 times weekly, pre- and post-treatment. Animals were killed by carbon dioxide inhalation and organs removed for immunohistochemistry and RNA analysis. All animals used in this study were maintained in accordance with the "Guide for the Care Use of Laboratory Animals"(DHHS Publication No.(NIH) 85–23, revised 1996). The protocol was approved by the Institutional Animal Care and Use Committee, Merck Research Laboratories, West Point, Pa.

Blood samples were obtained by tail incision, and collection into heparinized microhematocrit tubes (VWR) every 2–3 days during the course of the study. Tubes were centrifuged at 13,700 g for 2 minutes and hematocrit values were monitored. Plasma was collected for measurement of glucose and leptin levels. Glucose levels were measured using the Kodak Ektachem DT slides (Eastman Kodak Co.). Leptin and insulin levels were measured by an RIA assay performed by Linco Research, Inc.

What is claimed is:

1. A helper dependent adenoviral vector comprising the following contiguous sequences in the order given:
   (a) a first segment of adenovirus DNA, said first segment comprising a left adenoviral inverted terminal repeat (ITR) sequence, a viral origin of replication, and an adenoviral packaging signal;
   (b) a first segment of exogenous stuffer DNA which comprises a segment of human hypoxanthine-guanine phosphoribosyltransferase (HPRT) gene;
   (c) a transgene construct;
   (d) a second segment of exogenous stuffer DNA which comprises a segment of C346 cosmid; and
   (e) a second segment of adenovirus DNA, said second segment comprising a right ITR sequence;
   wherein the transgene and exogenous stuffer DNA components combined constitute at least 28kb and the vector is devoid of adenoviral protein-coding sequences.

2. A vector in accordance with claim 1 wherein the first segment of stuffer exogenous DNA is comprises a segment of intronil oypoxanthine-guanine phosphoribosyltrans ferase (HPRT) gene comprising a matrix association region.

3. A vector according to claim 1 wherein the adenovirus DNA comprises adenovirus type 5 DNA.

4. A vector according to claim 3 wherein the first segment of adenovirus DNA comprises nucleotides 1–440 of adenovirus type 5 DNA.

5. A vector according to claim 4 wherein the second segment of adenovirus DNA comprises nucleotides 35818–35935 of adenovirus type 5 DNA.

6. A vector according to claim 1 which is pSTK120.

7. An isolated mammalian cell comprising a vector according to claim 1.

* * * * *

UNITED STATES PATENT AND TRADEMARK OFFICE
CERTIFICATE OF CORRECTION

PATENT NO. : 6,630,346 B1
DATED : October 7, 2003
INVENTOR(S) : Manal Morsey et al.

It is certified that error appears in the above-identified patent and that said Letters Patent is hereby corrected as shown below:

<u>Title page,</u>
Item [75], Inventors, please replace "Stephan Kochanek, Ulm (DE)" with -- Stefan Kochanek, Ulm (DE) --.

<u>Column 24,</u>
Lines 62-65, please replace
"2. A vector in accordance with claim 1 wherein the first segment of stuffer exogenous DNA is comprises a segment of intronil oypoxanthine-guanine phosphoribosyltransferase (HPRT) gene comprising a matrix association region." with
-- 2. A vector in accordance with claim 1 wherein the first segment of exogenous stuffer DNA comprises a segment of intronic hypoxanthine-guanine phosphoribosyltransferase (HPRT) gene comprising a matrix association region. --

Signed and Sealed this

Tenth Day of February, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,630,346 B1
DATED : October 7, 2003
INVENTOR(S) : Manal Morsey et al.

It is certified that error appears in the above-identified patent and that said Letters Patent is hereby corrected as shown below:

Title page,
Item [75], Inventors, please replace "Stephan Kochanek, Ulm (DE)" with -- Stefan Kochanek, Ulm (DE) --
Item [73], Assignee, please replace "Merck & Co., Inc., Rahway, NJ (US)" with -- Merck & Co., Inc., Rahway, NJ (US); Baylor College of Medicine, Houston, TX (US). --

Column 24,
Lines 62-65, please replace:

"2. A vector in accordance with claim 1 wherein the first segment of stuffer exogenous DNA is comprises a segment of intronil oypoxanthine-guanine phosphoribosyltransferase (HPRT) gene comprising a matrix association region." with
-- 2. A vector in accordance with claim 1 wherein the first segment of exogenous stuffer DNA comprises a segment of intronic hypoxanthine-guanine phosphoribosyltransferase (HPRT) gene comprising a matrix association region. --

Signed and Sealed this

Eleventh Day of May, 2004

JON W. DUDAS
*Acting Director of the United States Patent and Trademark Office*